United States Patent
Eaton et al.

(10) Patent No.: US 10,550,438 B2
(45) Date of Patent: Feb. 4, 2020

(54) METHODS AND COMPOSITIONS FOR DETECTING BACTERIAL NUCLEIC ACID

(71) Applicant: GEN-PROBE INCORPORATED, San Diego, CA (US)

(72) Inventors: Barbara Lynn Eaton, San Diego, CA (US); Damon Kittredge Getman, Poway, CA (US); Traci Pawlowski, Carlsbad, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 15/557,912

(22) PCT Filed: Mar. 16, 2016

(86) PCT No.: PCT/US2016/022628
§ 371 (c)(1),
(2) Date: Sep. 13, 2017

(87) PCT Pub. No.: WO2016/149357
PCT Pub. Date: Sep. 22, 2016

(65) Prior Publication Data
US 2018/0291430 A1 Oct. 11, 2018

Related U.S. Application Data

(60) Provisional application No. 62/133,881, filed on Mar. 16, 2015, provisional application No. 62/168,405, filed on May 29, 2015, provisional application No. 62/168,688, filed on May 29, 2015.

(51) Int. Cl.
*C12Q 1/68* (2018.01)
*C12Q 1/689* (2018.01)

(52) U.S. Cl.
CPC ........ *C12Q 1/689* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 7,625,704 B2 | 12/2009 | Fredricks et al. | |
| 7,829,079 B2 | 11/2010 | Reid et al. | |
| 9,200,331 B2 | 12/2015 | Johnson et al. | |
| 9,657,352 B2* | 5/2017 | Getman | C12Q 1/689 |
| 2003/0050470 A1* | 3/2003 | An | C07H 21/00 536/24.3 |
| 2010/0075306 A1 | 3/2010 | Bretelle et al. | |
| 2011/0053802 A1 | 3/2011 | Forney et al. | |
| 2011/0151462 A1 | 6/2011 | Tynan et al. | |
| 2012/0264126 A1* | 10/2012 | Johnson | C12Q 1/689 435/6.11 |
| 2013/0288988 A1 | 10/2013 | Cartwright et al. | |
| 2013/0316922 A1 | 11/2013 | Balashov et al. | |
| 2014/0065617 A1* | 3/2014 | Getman | C12Q 1/689 435/6.11 |
| 2014/0302500 A1* | 10/2014 | Getman | C12Q 1/689 435/6.11 |

FOREIGN PATENT DOCUMENTS

WO 2013036928 A1 3/2013

OTHER PUBLICATIONS

GenBank Accession No. NR_025087.1, Lactobacillus jensenii strain ATCC 25258 16S ribosomal RNA gene, partial sequence (submitted Mar. 2000, retrieved on Oct. 23, 2018 from the Internet: https://www.ncbi.nlm.nih.gov/nuccore/NR_025087). (Year: 2000).*
GenBank Accession No. NR_041800.1, Lactobacillus crispatus strain ATCC 33820 16S ribosomal RNA gene, partial sequence (submitted Apr. 2000, retrieved on Oct. 23, 2018 from the Internet: https://www.ncbi.nlm.nih.gov/nuccore/NR_041800). (Year: 2000).*
Genbank Accession No. NR_044694.2, Gardnerella vaginalis strain 594 16S ribosomal RNA, partial sequence, submitted Aug. 2011, retrieved on Oct. 23, 2018 from the Internet: https://www.ncbi.nlm.nih.gov/nuccore/NR_044694). (Year: 2011).*
Genbank Accession No. AY738656.1, Uncultured *Eggerthella* sp. clone 123-f2 68 16S ribosomal RNA gene, partial sequence, submitted Aug. 2004, retrieved on Oct. 23, 2018 from the Internet: https://www.ncbi.nlm.nih.gov/nuccore/AY738656). (Year: 2004).*
Zariffard MR, Saifuddin M, Sha BE, Spear GT. Detection of bacterial vaginosis-related organisms by real-time PCR for Lactobacilli, Gardnerella vaginalis and Mycoplasma hominis. FEMS Immunol Med Microbiol. Dec. 13, 2002; 34(4):277-81. (Year: 2002).*
Balashov SV, Mordechai E, Adelson ME, Sobel JD, Gygax SE. Multiplex quantitative polymerase chain reaction assay for the identification and quantitation of major vaginal lactobacilli. Diagn Microbiol Infect Dis. Apr. 2014; 78(4):321-7. Epub Jan. 18, 2014. (Year: 2014).*
Obata-Yasuoka M, Ba-Thein W, Hamada H, Hayashi H. A multiplex polymerase chain reaction-based diagnostic method for bacterial vaginosis. Obstet Gynecol. Oct. 2002; 100(4):759-64. (Year: 2002).*
Shipitsyna E, Roos A, Datcu R, Hallén A, Fredlund H, Jensen JS, Engstrand L, Unemo M. Composition of the vaginal microbiota in women of reproductive age—sensitive and specific molecular diagnosis of bacterial vaginosis is possible? PLoS One. Apr. 9, 2013; 8(4):e60670: pp. 1-10. (Year: 2013).*
Shipitsyna et al. (Apr. 2013) Supporting Information-Table S1: PLoS One., 8(4):e60670: p. 1. (Year: 2013).*

(Continued)

*Primary Examiner* — Gary Benzion
*Assistant Examiner* — Olayinka A Oyeyemi
(74) *Attorney, Agent, or Firm* — Nicholas V. Sherbina; Jeffrey E. Landes

(57) ABSTRACT

Disclosed are methods for diagnosing Bacterial Vaginosis in a subject comprising performing an assay for the detection of any one or more of *Lactobacillus* sp., *Gardneralla vaginalis*, and *Eggerthella* sp. in a subject sample. Also disclosed are methods and compositions for detecting *Lactobacillus* sp., *Gardneralla vaginalis*, and/or *Eggerthella* nucleic acid in a sample.

11 Claims, 5 Drawing Sheets

Specification includes a Sequence Listing.

(56) References Cited

OTHER PUBLICATIONS

Chelliserrykattil et al., Development of a quantitative real-time transcription-mediated amplification assay for Simultaneous Detection of Multiple Nucleic Acid Analytes, J Mol. Diagn. 2009, 11, 680. (Year: 2009).*
GenBank Accession No. DQ975648, Uncultured *Lactobacillus* sp. clone W2_min_064 16S ribosomal RNA gene, partial sequence (submitted Aug. 2006, retrieved on Feb. 26, 2019 from the Internet: https://www.ncbi.nlm.nih.gov/nuccore/DQ975648). (Year: 2007).*
SantaLucia Jr, John. Physical principles and visual-OMP software for optimal PCR design. PCR Primer Design. Humana Press, 2007: pp. 3-33. (Year: 2007).*
EPO Communication pursuant to Rule 164(1) EPC, Supplemental Partial European Search Report, European Application No. 16765647.9, dated Jul. 9, 2018.
Ling et al., "Associations between Vaginal Pathogenic Community and Bacterial Vaginosis in Chinese Reproductive-Age Women," Plos One, 2013, 8(10): e76589. doi:10.1371/journal.pone.0076589, USA.
Pepin et al., "The Complex Vaginal Flora of West African Women with Bacterial Vaginosis," 2011, 6:9. e25082. https://doi.org/10.1371/journal.pone.0025082, USA.
EPO European Extended Search Report, European Application No. 16765647.9, dated Oct. 16, 2018.
Rantakokko-Jalava et al., "Direct Amplification of rRNA Genes in Diagnosis of Bacterial Infections," Journal of Clinical Microbiology, 2000, vol. 38, No. 1, pp. 32-29.
Ravel et al., "Translating the vaginal microbiome: gaps and challenges," Ravel and Brotman Genome Medicine, 2016, vol. 8, No. 35, pp. 1-3.
Biagi et al., "Quantitative variations in the vaginal bacterial population associated with asymptomatic infections: a real-time polymerase chain reaction study," Eur J Clin Microbiol Infect Dis, 2009, 28:281-285.
Dactu et al., "Vaginal microbiome in women from Greenland assessed by microscopy and quantitative PCR," BMC Infectious Diseases, 2013, 13:1-14.
De Backer et al., "Quantitative determination by real-time PCR of four vaginal *Lactobacillus* species, Gardnerella vaginalis and Atopobium vaginae indicates an inverse relationship between L. gasseri and L. iners," BMC Microbiology, 2007, 7:6-13.
Delaney et al., "Nugent Score Related to Vaginal Culture in Pregnant Women," The American College of Obstetricians and Gynecologists, 2001, vol. 98, No. 1, pp. 79-84.
Dols et al., "Microarray-based identification of clinically relevant vaginal bacteria in relation to bacterial vaginosis," American Journal of Obstetrics & Gynecology, 2011, 204:305.e1-7.
Fredricks et al., "Targeted PCR for Detection of Vaginal Bacteria Associated with Bacterial Vaginosis," Journal of Clinical Microbiology, 2007, vol. 45, No. 10, p. 3270-3276.
Hummelen et al., "Deep Sequencing of the Vaginal Microbiota of Women with HIV," PLoS ONE, 2010, vol. 5 , No. 8, pp. e12078.
Ling et al., "Molecular analysis of the diversity of vaginal microbiota associated with bacterial vaginosis," BMC Genomics, 2010, 11:488, pp. 2-16.
Ling et al., "Diversity of Cervicovaginal Microbiota Associated with Female Lower Genital Tract Infections," Microb Ecol, 2011, No. 61, pp. 704-714.
Mastromarino et al., "Charaterization and selection of vaginal Lactobacillus strains for the preparation of vaginal tablets," Journal of Applied Microbiology, 2002, vol. 93, No. 5, pp. 884-893.
Schwiertz et al., "Throwing the dice for the diagnosis of vaginal complaints?," Annals of Clinical Microbiology and Antimicrobials, 2006, vol. 5, No. 4, pp. 1-7.
Shipitsyna et al., "Composition of the Vaginal Microbiota in Women of Reproductive Age—Sensitive and Specific Molecular Diagnosis of Bacterial Vaginosis Is Possible?," 2013, vol. 8, No. 4, pp. e60670.
Speksnijder et al., "O3-S6.01 Improved diagnostics of bacterial vaginosis with molecular techniques," Sex Transm Infect, 2011, vol. 87, Suppl 1, pp. A81.
Spiegel, "Bacterial Vaginosis," Clinical Microbiology Reviews, 1991, vol. 4, No. 4, pp. 485-502.
Srinivasan et al., "Bacterial Communities in Women with Bacterial Vaginosis: High Resolution Phylogenetic Analyses Reveal Relationships of Microbiota to Clinical Criteria," PLoS ONE, 2012, vol. 7, No. 6, pp. e37818.
Srinivasan et al., "More Than Meets the Eye: Associations of Vaginal Bacteria with Gram Stain Morphotypes Using Molecular Phylogenetic Analysis," Plos One, 2013, vol. 8, No. 10, pp. e78633.
Zarrifard et al., "Detection of bacterial vaginosis-related organisms by real-time PCR for Lactobacilli, Gardnerella vaginalis and Mycoplasma hominis," FEMS Immunology and Medical Microbiology, 2002, No. 34, pp. 277-281.
Zozaya-Hinchliffe et al., "Quantitative PCR Assessments of Bacterial Species in Women with and without Bacterial Vaginosis," Journal of Clinical Microbiology, 2010, vol. 48, No. 5, pp. 1812-1819.
PCT International Preliminary Report on Patentability, International Application No. PCT/US2016/022628, dated Sep. 19, 2017.
PCT Written Opinion, International Application No. PCT/US2016/022628, dated Jul. 21, 2016.
PCT International Search report, International Application No. PCT/US2016/022628, dated Jul. 25, 2016.

* cited by examiner

```
gacgaacgct ggcggcgtgc ctaatacatg caagtcgagc gagcggaact aacagattta
cttcggtaat gacgttagga aagcgagcgg cggatgggtg agtaacacgt ggggaacctg
ccccatagtc tgggatacca cttggaaaca ggtgctaata ccggataaga aagcagatcg
catgatcagc ttttaaaagg cggcgtaagc tgtcgctatg ggatggcccc gcggtgcatt
agctagttgg taaggtaaag gcttaccaag gcgatgatgc atagccgagt tgagagactg
atcggccaca ttgggactga gacacggccc aaactcctac gggaggcagc agtagggaat
cttccacaat ggacgcaagt ctgatggagc aacgccgcgt gagtgaagaa ggttttcgga
tcgtaaagct ctgttgttgg tgaagaagga tagaggtagt aactggcctt tatttgacgg
taatcaacca gaaagtcacg gctaactacg tgccagcagc cgcggtaata cgtaggtggc
aagcgttgtc cggatttatt gggcgtaaag cgagcgcagg cggaagaata agtctgatgt
gaaagccctc ggcttaaccg aggaactgca tcggaactg ttttcttga gtgcagaaga
ggagagtgga actccatgtg tagcggtgga atgcgtagat atatggaaga acaccagtgg
cgaaggcggc tctctggtct gcaactgacg ctgaggctcg aaagcatggg tagcgaacag
gattagatac cctggtagtc catgccgtaa acgatgagtg ctaagtgttg ggaggtttcc
gcctctcagt gctgcagcta acgcattaag cactccgcct ggggagtacg accgcaaggt
tgaaactcaa aggaattgac gggggcccgc acaagcggtg gagcatgtgg tttaattcga
agcaacgcga agaaccttac caggtcttga catctagtgc catttgtaga gatacaaagt
tcccttcggg gacgctaaga caggtggtgc atggctgtcg tcagctcgtg tcgtgagatg
ttgggttaag tcccgcaacg agcgcaaccc ttgttattag ttgccagcat taagttgggc
actctaatga gactgccggt gacaaaccgg aggaaggtgg ggatgacgtc aagtcatcat
gccccttatg acctgggcta cacacgtgct acaatgggca gtacaacgag aagcgagcct
gcgaaggcaa gcgaatctct gaaagctgtt ctcagttcgg actgcagtct gcaactcgac
tgcacgaagc tggaatcgct agtaatcgcg gatcagcacg ccgcggtgaa tacgttcccg
ggccttgtac acaccgcccg tcacaccatg ggagtctgca atgcccaaag ccggtggcct
aaccttcggg aaggagccgt ctaaggcagg gcagatgact ggggtgaagt cgtaacaagg
tagccgtagg agaactgc
```

FIG. 1A

```
TGCCTAATACATGCAAGTCGAGCGAGCTTGCCTATAGAAGTTCTTCGGAATGGAAATAGATACAAGCT
AGCGGCGGATGGGTGAGTAACGCGTGGGTAACCTGCCCTTAAGTCTGGGATACCATTTGGAAACAGAT
GCTAATACCGGATAAAAGCTACTTTCGCATGAAAGAAGTTTAAAAGGCGGCGTAAGCTGTCGTAAAGG
ATGGACTTGCGATGCATTAGCTAGTTGGTAAGGTAACGGCTTACCAAGGCTGATGATGCATAGCCGAG
TTGAGAGACTGATCGGCCACATTGGGACTGAGACACGGCCCAAACTCCTACGGGAGGCAGCAGTAGGG
AATCTTCCACAATGGACGAAAGTCTGATGGAGCAACGCCGCGTGAGTGAAGAAGGTTTTCGGATCGTA
AAGCTCTGTTGTTGGTGAAGAAGGATAGAGGTAGTAACTGGCCTTTATTTGACGGTAATCAACCAGAA
AGTCACGGCTAACTACGTGCCAGCAGCCGCGGTAATACGTAGGTGGCAAGCGTTGTCCGGATTTATTG
GGCGTAAAGCGAGCGCAGGCGGATTGATAAGTCTGATGTGAAAGCCTTCGGCTCAACCGAAGAACTGC
ATCAGAAACTGTCAATCTTGAGTGCAGAAGAGGAGAGTGGAACTCCATGTGTAGCGGTGGAATGCGTA
GATATATGGAAGAACACCAGTGGCGAAGGCGGCTCTCTGGTCTGTAACTGACGCTGAGGCTCGAAAGC
ATGGGTAGCGAACAGGATTAGATACCCTGGTAGTCCATGCCGTAAACGATGAGTGCTAAGTGTTGGGA
GGTTTCCGCCTCTCAGTGCTGCAGCTAACGCATTAAGCACTCCGCCTGGGGAGTACGACCGCAAGGTT
GAAACTCAAAGGAATTGACGGGGGCCCGCACAAGCGGTGGAGCATGTGGTTTAATTCGAAGCAACGCG
AAGAACCTTACCAGGTCTTGACATCCTTTGACCACCTAAGAGATTAGGTTTTCCCTTCGGGGACAAAG
AGACAGGTGGTGCATGGCTGTCGTCAGCTCGTGTCGTGAGATGTTGGGTTAAGTCCCGCAACGAGCGC
AACCCTTGTTAATAGTTGCCAGCATTAAGTTGGGCACTCTATTGAGACTGCCGGTGACAAACCGGAGG
AAGGTGGGGATGACGTCAAGTCATCATGCCCCTTATGACCTGGGCTACACACGTGCTACAATGGGCAG
TACAACGAGAAGCGAACCTGTGAAGGCAAGCGGATCTCTTAAAGCTGTTCTCAGTTCGGACTGTAGGC
TGCAACTCGCCTACACGAAGCTGGAATCGCTAGTAATCGCGGATCAGCACGCCGCGGTGAATACGTTC
CCGGGCCTTGTACACACCGCCCGTCACACCATGAGAGTTTGTAACACCCAAAGTCGGTGAGGTAACCT
TTGGAGCCAGCCGCCTAAGGTGGGACAGATGATTAGGGTGAAGTCGTAACAAGGTAGCCGTAGGAGAA
```

FIG 1B

```
ctgcggcgtg cctaatacat gcaagtcgag cgagcttgcc tagatgaatt tggtgcttgc
accagatgaa actagataca agcgagcggc ggacgggtga gtaacacgtg ggtaacctgc
ccaagagact gggataacac ctggaaacag atgctaatac cggataacaa cactagacgc
atgtctagag tttaaaagat ggttctgcta tcactcttgg atggacctgc ggtgcattag
ctagttggta aggtaacggc ttaccaaggc aatgatgcat agccgagttg agagactgat
cggccacatt gggactgaga cacggcccaa actcctacgg gaggcagcag tagggaatct
tccacaatgg acgcaagtct gatggagcaa cgccgcgtga gtgaagaagg gtttcggctc
gtaaagctct gttggtagtg aagaaagata gaggtagtaa ctggccttta tttgacggta
attacttaga aagtcacggc taactacgtg ccagcagccg cggtaatacg taggtggcaa
gcgttgtccg gatttattgg gcgtaaagcg agtgcaggcg gttcaataag tctgatgtga
aagccttcgg ctcaaccgga gaattgcatc agaaactgtt gaacttgagt gcagaagagg
agagtggaac tccatgtgta gcggtggaat gcgtagatat atggaagaac accagtggcg
aaggcggctc tctggtctgc aactgacgct gaggctcgaa agcatggta gcgaacagga
ttagataccc tggtagtcca tgccgtaaac gatgagtgct aagtgttggg aggtttccgc
ctctcagtgc tgcagctaac gcattaagca ctccgcctgg ggagtacgac cgcaaggttg
aaactcaaag gaattgacgg gggcccgcac aagcggtgga gcatgtggtt taattcgaag
caacgcgaag aaccttacca ggtcttgaca tccagtgcaa acctaagaga ttaggtgttc
ccttcgggga cgctgagaca ggtggtgcat ggctgtcgtc agctcgtgtc gtgagatgtt
gggttaagtc ccgcaacgag cgcaacccct gtcattagtt gccatcatta agttgggcac
tctaatgaga ctgccggtga caaccggag gaaggtgggg atgacgtcaa gtcatcatgc
cccttatgac ctgggctaca cacgtgctac aatggacggt acaacgagaa gcgaacctgc
gaaggcaagc ggatctctga aagccgttct cagttcggac tgtaggctgc aactcgccta
cacgaagctg gaatcgctag taatcgcgga tcagcacgcc gcggtgaata cgttcccggg
ccttgtacac accgcccgtc acaccatgag agtctgtaac acccaaagcc ggtgggataa
cctttatagg agtcagccgt ctaaggtagg acagatgatt agggtgaagt cgtaacaagg
tagccgtagg agaacctgcg gttggatca
```

FIG. 2

```
tttcgtggag ggttcgattc tggctcagga tgaacgctgg cggcgtgctt aacacatgcn
agtcgaacgg gatctgacca gcttgctggt tggtgagagt ggcgaacggg tgagtaatgc
gtgaccaacc tgccccatgc tccagaatag ctcttggaaa cgggtggtaa tgctggatgc
tccaacttga cgcatgtctt gttgggaaag tgtttagtgg catgggatgg ggtcgcgtcc
tatcagcttg taggcggggt aatggcccac ctaggcttcg acgggtagcc ggcctgagag
ggcggacggc cacattggga ctgagatacg gcccagactn ctacgggagg cagcagtggg
gaatattgcg caatggggga aaccctgacg cagcgacgnc gcgtgcggga tgaaggcctt
cgggttgtaa accgcttttg attgggagca agccttttgg gtgagtgtac ctttcgaata
agcgccggct aactacgtgc cagcagccgc ggtaatacgt agggcgcaag cgttatccgg
aattattggg cgtaaagagc ttgtaggcgg ttcgtcgcgt ctggtgtgaa agcccatcgc
ttaacggtgg gnttgcgccg ggtacgggcg ggctagagtg cagtaggga gactggaatt
ctcggtgtaa cggtggaatg tgtagatatc gggaagaaca ccaatggcga aggcaggtct
ctgggctgtt actgacgctg agaagcgaaa gcgtggggag cgaacaggat tagataccct
ggtagtccac gccgtaaacg gtggacgctg gatgtggggc ccattccacg ggttctgtgt
cggagctaac gcgttaagcg tcccgcctgg ggagtacggc cgcaaggcta aaactcaaag
aaattgacgg gggccngcac aagcggcgga gcatgcggat taattcgatg naacgcgaag
aaccttacct gggcttgaca tgtgcctgac gactgcagag atgtggtttc cnttcggggc
aggttcacag gtggtgcatg gtcgtcgtca gctcgtgtcg tgagatgttg ggttaagtcc
cgcaacgagc gcaaccctcg ccctgtgttg ccagcgggtt atgccgggaa ctcacggggg
accgccgggg ttaccncgga ggaaggtggg natgacgtca gatcatcatg ccccttacgt
ccagggcttc acgcatgcta caatggccag tacaacgggt tgcttcatgg tgacatggtg
ctaatccctt aaaactngtc tcagttcgga tcgtagtctg caactcgact acgtgaaggc
ggagtcgcta gtaatcgcga atcagcaacg tcgcggtgaa tgcgttcccg ggccttgtac
acaccgcccg tcaagtcatg aaagtgggca gcacccgaag ccggtggcct aaccctttg
ggatggagcc gtctaaggtg aggctcgtga ttggg
```

FIG. 3

```
tggggaatat tgcgcaatgg gggaaaccct gacgcagcaa cgccgcgtgc gggatgaagg
ccttcgggtt gtaaaccgct ttcagcaggg aagacatcga cggtacctgc agaagaagcc
ccggctaact acgtgccagc agccgcggta atacgtaggg ggcgagcgtt atccggattc
attgggcgta aagcgcgcgc aggcggttgc tcaagcggaa cctctaatct cggggcttaa
cctcgagccg ggttccgaac tggacgactc gagtgcggta gaggcagatg gaattcccgg
tgtagcggtg gaatgcgcag atatcgggaa gaacaccaac ggcgaaggca gtctgctggg
ccgtcactga cgctgaggcg cgaaagctgg gggagcgaac aggattagat accctggtag
tcccagccgt aaacgatgag cgctgggtgt gggagattac atcttccgtg ccgaagctaa
cgcattaagc gctccgcctg gggagtacgg ccgcaaggct aaaactcaaa ggaattgacg
ggggcccgca caagcagcgg agcatgtggc ttaattcgaa gcaacgcgaa gaaccttacc
agggcttgac atgtaggtga agcggcggaa acgtcgtggc cgaaaggagc ctacacaggt
ggtgcatggc tgtcgtcagc tcgtgtcgtg agatgttggg ttaagtcccg caacgagcgc
aaccccctgcc ccgtgttacc agcatttagt tggggactcg cggggggactg ccggcgtcaa
gccggaggaa ggcggggatg acgtcaagtc atcatgcccc ttatgccctg ggccgcacac
gtgctacaat ggccggcaca gcgggctgca acctagcgat aggaagcgaa tcccgtaaag
ccggtcccag ttcggattgg aggctgaaac ccgcctccat gaagccggag ttgctagtaa
tcgcggatca gcacgccgcg gtgaatgcgt tcccgggcct
```

FIG. 4

METHODS AND COMPOSITIONS FOR DETECTING BACTERIAL NUCLEIC ACID

CROSS-REFERENCE TO RELATED APPLICATIONS

This application is a national stage entry of International Patent Application No. PCT/US2016/022628, filed Mar. 16, 2016, and claims benefit of priority under 35 U.S.C § 119(e) to provisional application No. 62/133,881, filed Mar. 16, 2015, 62/168,405, filed May 29, 2015, and 62/168,688, filed May 29, 2015; the entire contents of each are incorporated herein by reference

REFERENCE TO SEQUENCE LISTING

The instant application contains a Sequence Listing which has been submitted in ASCII format via EFS-Web and is hereby incorporated by reference in its entirety. Said ASCII Copy, created on Aug. 8, 2017, is named "DIA-0002-05-UT_ST25.txt" and is 31 KB in size.

BACKGROUND

According to the National Health and Nutrition Examination Survey, nearly a third of women between the age of 14 and 49 have bacterial vaginosis (BV). (See Allsworth and Peipert, *Obstetrics and Gynecology* 109:114-120, 2007). BV is the most common cause of vaginal discharge and a reason many women seek medical attention. It is also associated with preterm birth, low birth weight, pelvic inflammatory disease, an increase in STD infections, including HIV, and a greater risk of passing HIV on to sex partners. See Srinivasan and Fredricks, *Interdisciplinary Perspectives on Infectious Diseases*, Vol. 2008, Article ID 750479, 22 pages, 2008). Women with bacterial vaginosis may have symptoms including a malodorous vaginal discharge or irritation, however, as many as half of the women with diagnosable BV have no clear symptoms (see Srivinvasan and Fredricks, supra).

No single etiologic agent is known to be the cause of BV. Most researchers and the CDC consider bacterial vaginosis to be the result of a disruption to the normal bacterial flora of the vagina. Unlike common infections, this dysbiosis is not the result of an individual bacterial species. See CDC Factsheet, 2014 (BV-Fact-Sheet-March-2014.pdf, from CDC website). A dysbiosis is a disruption of the normal microbiota within a body environment such as the vagina. See Nibali et al., *Journal of Oral Microbiology* 6:22962, 2014.

BV is diagnosed in the clinic using the Amsel Criteria and in the laboratory using the Nugent Scoring System. The later relies on counting bacterial morphotypes with the aid of the Gram stain. In this way, the Nugent Score is a visual assessment of dysbiosis—it scores the bad bacteria against the good. See Nugent et al., *Journal of Clinical Microbiology* 29:297-301, 1991. The Amsel Criteria evaluates a sample for the presence of clue cells, pH, color and odor which are key symptoms associated with BV. See Amsel et al., *Am. J. Med.* 74:14-22, 1983. A wet mount of the sample is examined with a microscope to detect clue cells which are human epithelial cells covered with bacteria thought to predominately consist of *G. vaginalis*.

Molecular tests generally target multiple organisms which have strong correlations with bacterial vaginosis. Which organisms are targeted varies from test to test. In nearly all cases, high abundance anaerobic bacteria are targeted such as *Atopobium*, *Gardnerella*, and *Megasphaera* species.

The only FDA approved test for BV (BD Affirm VPIII 2010), was found to have a sensitivity of 67.6% and a specificity of 76.4% in a study by Cartwright et al. (*Journal of Clinical Microbiology* 51:3694-3699, 2013). For the purpose diagnosing BV, the Affirm product detects *G. vaginalis* as its sole indicator. The product package insert indicates the Affirm product is 95.1% sensitive and 83.3% specific when compared to a scored gram stain method.

Cartwright et al., supra, used a multiplex assay for the detection of *Atopobium vaginae*, BVAB-2 and *Megasphaera*-1 for the diagnosis of BV. They measured the performance of this assay against a combination of Nugent and Amsel results in a population of 323 women (93% African-American, 7% white non-Hispanic). They reported this test was 96.9% sensitive and 92.6% specific when compared to the combination of Nugent and Amsel scores. They did not report the results of this assay relative to the Nugent Score alone.

SUMMARY

In one aspect, the present invention provides a method for determining the presence or absence of Bacterial Vaginosis (BV) in a subject. In some embodiments, the method generally includes the following steps: (a) providing a sample from a subject suspected of having BV; (b) performing an assay for the detection of *Lactobacillus* sp., *G. vaginalis*, and *Eggerthella* sp. in the sample; (c) for each of *Lactobacillus* sp., *G. vaginalis*, and *Eggerthella* sp., assigning a status of either positive or negative based on the detection assay; and (d) determining the presence or absence of BV in the subject based on a combination of the assigned *Lactobacillus* sp. status, *G. vaginalis* status, and *Eggerthella* sp. status from step (c), where (i) a negative status for both *G. vaginalis* and *Eggerthella* sp. indicates the absence of BV in the subject, (ii) a positive status for both *G. vaginalis* and *Eggerthella* sp. indicates the presence of BV in the subject, (iii) if the status of *Lactobacillus* sp. is positive, then a negative status for at least one of *G. vaginalis* and *Eggerthella* indicates the absence of BV in the subject, and (iv) if the status of *Lactobacillus* sp. is negative, then a positive status for at least one of *G. vaginalis* and *Eggerthella* indicates the presence of BV in the subject. In other embodiments, the method generally includes the following steps: (a) providing a sample from a subject suspected of having BV; (b) performing an assay for the detection of *Lactobacillus* sp. and *G. vaginalis* in the sample; (c) for each of *Lactobacillus* sp. and *G. vaginalis*, assigning a status of either positive or negative based on the detection assay; and (d) determining the presence or absence of BV in the subject based on a combination of the assigned *Lactobacillus* sp. status and *G. vaginalis* status from step (c), where (i) a negative status for *G. vaginalis* indicates the absence of BV in the subject, and (ii) if the status of *G. vaginalis* is positive, then a positive status for *Lactobacillus* sp. indicates the absence of BV in the subject and a negative status for *Lactobacillus* sp. indicates the presence of BV in the subject.

In some embodiments of a method for diagnosing BV as above, the assay for detection of *Lactobacillus* sp., *G. vaginalis*, and *Eggerthella* sp., or the assay for detection of *Lactobacillus* sp. and *G. vaginalis*, is a nucleic-acid-based detection assay. In some embodiments the *Lactobacillus* sp. is from the vaginal microbiome. In some embodiments the *Eggerthella* sp. is from the vaginal microbiome. Particularly suitable nucleic-acid-based detection assays include amplification-based assays such as, for example, an assay comprising an isothermal amplification reaction (e.g., a transcription-mediated amplification (TMA) reaction), which may be performed in real time. In certain embodiments, the nucleic-acid-based detection assay targets the 16S rRNA of *Lactobacillus* sp., *G. vaginalis*, and *Eggerthella* sp., or the 16S rRNA of *Lactobacillus* sp. and *G. vaginalis*. In particular variations, the nucleic-acid-based detection assay targets (i) a *Lactobacillus* sp. 16S rRNA region corresponding to a region of SEQ ID NO:1 from about nucleotide position 91 to about nucleotide position 265; (ii) a *G. vaginalis* 16S rRNA region corresponding to a region of SEQ ID NO:3 from about nucleotide position 964 to about nucleotide position 1036; and/or (iii) an *Eggerthella* sp. 16S rRNA region corresponding to a region of SEQ ID NO:4 from about nucleotide position 165 to about nucleotide position 259.

In certain embodiments of a method for diagnosing BV as above comprising a nucleic-acid-based detection assay, the assay is an amplification-based assay including the following steps:

(1) contacting the sample with
first and second *Lactobacillus*-specific amplification oligomers for amplifying a target region of a *Lactobacillus* sp. target nucleic acid, where (i) the first *Lactobacillus*-specific amplification oligomer comprises a first *Lactobacillus*-specific target-hybridizing sequence substantially corresponding to the nucleotide sequence of residues 28-45 of SEQ ID NO:7 or residues 28-45 of SEQ ID NO:8 and (ii) the second *Lactobacillus*-specific amplification oligomer comprises a second *Lactobacillus*-specific target-hybridizing sequence substantially corresponding to the nucleotide sequence of SEQ ID NO:6;
first and second *G. vaginalis*-specific amplification oligomers for amplifying a target region of a *G. vaginalis* target nucleic acid, where (i) the first *G. vaginalis*-specific amplification oligomer comprises a first *G. vaginalis*-specific target-hybridizing sequence substantially corresponding to the nucleotide sequence of residues 28-45 of SEQ ID NO:13 and (ii) the second *G. vaginalis*-specific amplification oligomer comprises a second *G. vaginalis*-specific target-hybridizing sequence substantially corresponding to the nucleotide sequence of SEQ ID NO:12; and
first and second *Eggerthella*-specific amplification oligomers for amplifying a target region of an *Eggerthella* sp. target nucleic acid, where (i) the first *Eggerthella*-specific amplification oligomer comprises a first *Eggerthella*-specific target-hybridizing sequence substantially corresponding to the nucleotide sequence of residues 28-51 of SEQ ID NO:17 and (ii) the second *Eggerthella*-specific amplification oligomer comprises a second *Eggerthella*-specific target-hybridizing sequence substantially corresponding to the nucleotide sequence of SEQ ID NO:16;

(2) performing an in vitro nucleic acid amplification reaction, where any *Lactobacillus* sp., *G. vaginalis*, and *Eggerthella* sp. target nucleic acid, if present in the sample, is used as a template for generating one or more amplification products corresponding to the *Lactobacillus* sp., *G. vaginalis*, and *Eggerthella* sp. target regions; and (3) detecting the presence or absence of the one or more amplification products.

In other embodiments of a method for diagnosing BV comprising a nucleic-acid-based detection assay, the assay is an amplification-based assay including the following steps:

(1) contacting the sample with
first and second *Lactobacillus*-specific amplification oligomers for amplifying a target region of a *Lactobacillus* sp. target nucleic acid, where (i) the first *Lactobacillus*-specific amplification oligomer comprises a first *Lactobacillus*-specific target-hybridizing sequence substantially corresponding to the nucleotide sequence of residues 28-45 of SEQ ID NO:7 or residues 28-45 of SEQ ID NO:8 and (ii) the second *Lactobacillus*-specific amplification oligomer comprises a second *Lactobacillus*-specific target-hybridizing sequence substantially corresponding to the nucleotide sequence of SEQ ID NO:6; and
first and second *G. vaginalis*-specific amplification oligomers for amplifying a target region of a *G. vaginalis* target nucleic acid, where (i) the first *G. vaginalis*-specific amplification oligomer comprises a first *G. vaginalis*-specific target-hybridizing sequence substantially corresponding to the nucleotide sequence of residues 28-45 of SEQ ID NO:13 and (ii) the second *G. vaginalis*-specific amplification oligomer comprises a second *G. vaginalis*-specific target-hybridizing sequence substantially corresponding to the nucleotide sequence of SEQ ID NO:12;

(2) performing an in vitro nucleic acid amplification reaction, where any *Lactobacillus* sp. and *G. vaginalis* target nucleic acid, if present in the sample, is used as a template for generating one or more amplification products corresponding to the *Lactobacillus* sp. and *G. vaginalis* target regions; and (3) detecting the presence or absence of the one or more amplification products.

In some variations of a method for diagnosing BV comprising an amplification-based detection assay as above, the first *Lactobacillus*-specific target-hybridizing sequence comprises the nucleotide sequence of residues 28-45 of SEQ ID NO:7 or residues 28-45 of SEQ ID NO:8; the second *Lactobacillus*-specific target-hybridizing sequence comprises the nucleotide sequence of SEQ ID NO:6; the first *G. vaginalis*-specific target-hybridizing sequence comprises the nucleotide sequence of residues 28-45 of SEQ ID NO:13; the second *G. vaginalis*-specific target-hybridizing sequence comprises the nucleotide sequence of SEQ ID NO:12; the first *Eggerthella*-specific target-hybridizing sequence comprises the nucleotide sequence of residues 28-51 of SEQ ID NO:17; and/or the second *Eggerthella*-specific target-hybridizing sequence comprises the nucleotide sequence of SEQ ID NO:16. In some such embodiments, the first *Lactobacillus*-specific target-hybridizing sequence consists of the nucleotide sequence of residues 28-45 of SEQ ID NO:7 or residues 28-45 of SEQ ID NO:8; the second *Lactobacillus*-specific target-hybridizing sequence consists of the nucleotide sequence of SEQ ID NO:6; the first *G. vaginalis*-specific target-hybridizing sequence consists of the nucleotide sequence of residues 28-45 of SEQ ID NO:13; the second *G. vaginalis*-specific target-hybridizing sequence consists of the nucleotide sequence of SEQ ID NO:12; the first *Eggerthella*-specific target-hybridizing sequence consists of the nucleotide sequence of residues 28-51 of SEQ ID NO:17; and/or the second *Eggerthella*-specific target-hybridizing sequence consists of the nucleotide sequence of SEQ ID NO:16.

In some variations of a method for diagnosing BV comprising an amplification-based detection assay as above, the first *Lactobacillus*-specific target-hybridizing sequence substantially corresponds to the nucleotide sequence of residues 28-45 of SEQ ID NO:7, and the sample is further contacted with a third *Lactobacillus*-specific amplification oligomer for amplifying the *Lactobacillus* sp. target region, where the third *Lactobacillus*-specific amplification oligomer includes a third *Lactobacillus*-specific target-hybridizing sequence substantially corresponding to the nucleotide sequence of residues 28-45 of SEQ ID NO:8. In some such embodiments, the third *Lactobacillus*-specific target-hybridizing sequence comprises the nucleotide sequence of residues 28-45 of SEQ ID NO:8. In a particular variation, the third *Lactobacillus*-specific target-hybridizing sequence consists of the nucleotide sequence of residues 28-45 of SEQ ID NO:8.

In some embodiments of a method for diagnosing BV comprising an amplification-based detection assay as above, at least one of the first *Lactobacillus*-specific amplification oligomer, the first *G. vaginalis*-specific amplification oligomer, and the first *Eggerthella*-specific amplification oligomer (or at least one of the first *Lactobacillus*-specific amplification oligomer and the first *G. vaginalis*-specific amplification oligomer) is a promoter primer or promoter provider further comprising a promoter sequence located 5' to the respective target hybridizing sequence. In some such embodiments where the first *Lactobacillus*-specific target-hybridizing sequence substantially corresponds to the nucleotide sequence of residues 28-45 of SEQ ID NO:7 and the sample is further contacted with a third *Lactobacillus*-specific amplification oligomer for amplifying the *Lactobacillus* sp. target region, the third *Lactobacillus*-specific amplification oligomer is a promoter primer or promoter provider further comprising a promoter sequence located 5' to the third *Lactobacillus*-specific target hybridizing sequence. A particularly suitable promoter sequence is a T7 promoter sequence such as, for example, a promoter sequence having the nucleotide sequence of residues 1-27 of SEQ ID NO:7. In specific variations, the first *Lactobacillus*-specific amplification oligomer has the nucleotide sequence of SEQ ID NO:7; the first *G. vaginalis*-specific amplification oligomer has the nucleotide sequence of SEQ ID NO:13; and/or the first *Eggerthella*-specific amplification oligomer has the nucleotide sequence of SEQ ID NO:17. In some embodiments as above where the sample is further contacted with a third *Lactobacillus*-specific amplification oligomer for amplifying the *Lactobacillus* sp. target region, the third *Lactobacillus*-specific amplification oligomer has the nucleotide sequence of SEQ ID NO:8.

In certain embodiments of a method for diagnosing BV comprising an amplification-based detection assay as above, the method further includes purifying the *Lactobacillus, G. vaginalis*, and *Eggerthella* target nucleic acids, or purifying the *Lactobacillus* and *G. vaginalis* target nucleic acids, if present, from other components in the sample before step (2). In some such embodiments, the purifying step includes contacting the sample with at least one capture probe oligomer comprising a target-hybridizing sequence covalently attached to a sequence or moiety that binds to an immobilized probe. For example, the sample may be contacted with a *Lactobacillus*-specific capture probe oligomer, a *G. vaginalis*-specific capture probe oligomer, and an *Eggerthella*-specific capture probe oligomer, where each of the *Lactobacillus*-specific, *G. vaginalis*-specific, and *Eggerthella*-specific capture probe oligomers comprises a capture probe target-hybridizing sequence that specifically hybridizes to a target sequence within the *Lactobacillus, G. vaginalis*, or *Eggerthella* target nucleic acid, respectively, and where each of the *Lactobacillus*-specific, *G. vaginalis*-specific, and *Eggerthella*-specific capture probe target-hybridizing sequences is covalently attached to the sequence or moiety that binds to the immobilized probe. In some embodiments directed to detection of *Lactobacillus* sp. and *G. vaginalis*, the sample may be contacted with a *Lactobacillus*-specific capture probe oligomer and a *G. vaginalis*-specific capture probe oligomer, where each of the *Lactobacillus*-specific and *G. vaginalis*-specific capture probe oligomers comprises a capture probe target-hybridizing sequence that specifically hybridizes to a target sequence within the *Lactobacillus* or *G. vaginalis* target nucleic acid, respectively, and where each of the *Lactobacillus*-specific and *G. vaginalis*-specific capture probe target-hybridizing sequences is covalently attached to the sequence or moiety that binds to the immobilized probe. In specific variations, the *Lactobacillus*-specific capture probe target-hybridizing sequence substantially corresponds to the nucleotide sequence of residues 1-12 of SEQ ID NO:5, the *G. vaginalis*-specific capture probe target-hybridizing sequence substantially corresponds to the nucleotide sequence of residues 1-17 of SEQ ID NO:11, and/or the *Eggerthella*-specific capture probe target hybridizing sequence substantially corresponds to the nucleotide sequence of residues 1-21 of SEQ ID NO:15. In some embodiments, the *Lactobacillus*-specific capture probe oligomer has the nucleotide sequence of SEQ ID NO:5, the *G. vaginalis*-specific capture probe oligomer has the nucleotide sequence of SEQ ID NO:11, and/or the *Eggerthella*-specific capture probe oligomer has the nucleotide sequence of SEQ ID NO:15.

In some embodiments of a method for diagnosing BV comprising an amplification-based detection assay as above, the detecting step (3) includes (i) contacting the one or more amplification products with a first *Lactobacillus*-specific detection probe that specifically hybridizes to the *Lactobacillus* sp. target region, a first *G. vaginalis*-specific detection probe that specifically hybridizes to the *G. vaginalis* target region, and a first *Eggerthella*-specific detection probe that specifically hybridizes to the *Eggerthella* sp. target region, and (ii) detecting the presence or absence of any target-hybridized *Lactobacillus*-specific, *G. vaginalis*-specific, and/or *Eggerthella*-specific detection probe. In some embodiments of a method for diagnosing BV comprising an amplification-based detection assay for detection of *Lactobacillus* sp. and *G. vaginalis* as above, the detecting step (3) includes (i) contacting the one or more amplification products with a first *Lactobacillus*-specific detection probe that specifically hybridizes to the *Lactobacillus* sp. target region and a first *G. vaginalis*-specific detection probe that specifically hybridizes to the *G. vaginalis* target region, and (ii) detecting the presence or absence of any target-hybridized *Lactobacillus*-specific and/or *G. vaginalis*-specific detection probe. In some embodiments, the first *Lactobacillus*-specific detection probe comprises a target-hybridizing sequence substantially corresponding to SEQ ID NO:9, the first *G. vaginalis*-specific detection probe comprises a target-hybridizing sequence substantially corresponding to residues 1-19 of SEQ ID NO:14, and/or the first *Eggerthella*-specific detection probe comprises a target-hybridizing sequence substantially corresponding to SEQ ID NO:18. In specific variations, the first *Lactobacillus*-specific detection probe has the nucleotide sequence of SEQ ID NO:9, the first *G.* vaginalis-specific detection probe has the nucleotide sequence of SEQ ID NO:14, and/or the first Eggerthella-specific detection probe has the nucleotide sequence of SEQ ID NO:18. In some embodiments as above, the detecting step (3) further includes contacting the one or more amplification products with a second Lactobacillus-specific detection probe that specifically hybridizes to the Lactobacillus sp. target region, where the second Lactobacillus-specific detection probe comprises a target-hybridizing sequence substantially corresponding to residues 6-21 of SEQ ID NO:10; in some such embodiments, the second Lactobacillus-specific detection probe has the nucleotide sequence of SEQ ID NO:10.

In certain embodiments of a method for diagnosing BV comprising an amplification-based detection assay and the use of a first Lactobacillus-specific detection probe, a first G. vaginalis-specific detection probe, and a first Eggerthella-specific detection probe (or the use of a first Lactobacillus-specific detection probe and a first G. vaginalis-specific detection probe) as above, each of said probes comprises a label. In some embodiments further including contacting the one or more amplification products with a second Lactobacillus-specific detection probe, the second Lactobacillus-specific detection probe comprises a label. Particularly suitable labels include chemiluminescent and fluorescent labels.

In some embodiments of a method for diagnosing BV comprising an amplification-based detection assay and the use of labeled detection probes as above, the detecting step (3) occurs during the amplifying step (2). In some such variations, each detection probe comprises a fluorescent label and a quencher. Particularly suitable detection probes comprising a fluorescent label and a quencher include a molecular torch, a molecular beacon, and a TaqMan detection probe.

In certain embodiments of a method for diagnosing BV comprising an amplification-based detection assay and the use of detection probes as above, at least one of the first Lactobacillus-specific detection probe, the first G. vaginalis-specific detection probe, and the first Eggerthella-specific detection probe (or at least one of the first Lactobacillus-specific detection probe and the first G. vaginalis-specific detection probe) further comprises a non-target-hybridizing sequence. In some embodiments further including contacting the one or more amplification products with a second Lactobacillus-specific detection probe, the second Lactobacillus-specific detection probe further comprises a non-target-hybridizing sequence. In some such variations as above, any one of (e.g., each of) the detection probes is a molecular torch or a molecular beacon.

In some embodiments of a method for diagnosing BV comprising an amplification-based detection assay as above, the amplification reaction at step (2) is an isothermal amplification reaction. In particular variations, the isothermal amplification reaction is a transcription-mediated amplification (TMA) reaction. In certain embodiments, the isothermal amplification reaction is a real-time amplification reaction.

In some embodiments of a method for diagnosing BV as above, the method includes the detection of no more than ten bacterial genera associated with BV. For example, in certain variations, the method includes the detection of no more than five bacterial genera associated with BV. In a specific variation, the method does not include detection of bacterial genera associated with BV other than Lactobacillus, Gardnerella, and Eggerthella. In another specific variation, the method does not include detection of bacterial genera associated with BV other than Lactobacillus and Gardnerella.

In some embodiments of a method for diagnosing BV as above, if the presence of BV is indicated in the subject, then the method further includes administering a treatment regime for BV to the subject.

In some embodiments of a method for diagnosing BV as above, the method is a method for monitoring BV in the subject and the subject is undergoing a treatment regime for BV prior to step (a). In some such variations, if the presence of BV is indicated in the subject, then the method further includes either (i) administering the treatment regime for BV to the subject or (ii) administering a different treatment regime for BV to the subject.

In another aspect, the present invention provides a multiplex detection method. In some embodiments, the multiplex detection method is for determining the presence or absence of each of each of Lactobacillus sp., G. vaginalis, and Eggerthella sp. in a sample. The method generally includes the following steps:

(1) contacting a sample, the sample suspected of containing at least one of Lactobacillus sp., G. vaginalis, and Eggerthella sp., with
  (a) first and second Lactobacillus-specific amplification oligomers for amplifying a target region of a Lactobacillus sp. target nucleic acid, where (i) the first Lactobacillus-specific amplification oligomer comprises a first Lactobacillus-specific target-hybridizing sequence substantially corresponding to the nucleotide sequence of residues 28-45 of SEQ ID NO:7 or residues 28-45 of SEQ ID NO:8 and (ii) the second Lactobacillus-specific amplification oligomer comprises a second Lactobacillus-specific target-hybridizing sequence substantially corresponding to the nucleotide sequence of SEQ ID NO:6;
  (b) first and second G. vaginalis-specific amplification oligomers for amplifying a target region of a G. vaginalis target nucleic acid, where (i) the first G. vaginalis-specific amplification oligomer comprises a first G. vaginalis-specific target-hybridizing sequence substantially corresponding to the nucleotide sequence of residues 28-45 of SEQ ID NO:13 and (ii) the second G. vaginalis-specific amplification oligomer comprises a second G. vaginalis-specific target-hybridizing sequence substantially corresponding to the nucleotide sequence of SEQ ID NO:12; and
  (c) first and second Eggerthella-specific amplification oligomers for amplifying a target region of an Eggerthella sp. target nucleic acid, where (i) the first Eggerthella-specific amplification oligomer comprises a first Eggerthella-specific target-hybridizing sequence substantially corresponding to the nucleotide sequence of residues 28-51 of SEQ ID NO:17 and (ii) the second Eggerthella-specific amplification oligomer comprises a second Eggerthella-specific target-hybridizing sequence substantially corresponding to the nucleotide sequence of SEQ ID NO:16;
(2) performing an in vitro nucleic acid amplification reaction, where any Lactobacillus sp., G. vaginalis, and Eggerthella sp. target nucleic acid, if present in the sample, is used as a template for generating one or more amplification products corresponding to the Lactobacillus sp., G. vaginalis, and Eggerthella sp. target regions; and
(3) detecting the presence or absence of the one or more amplification products, thereby determining the presence or absence of *Lactobacillus* sp., *G. vaginalis*, and *Eggerthella* sp. in the sample.

In other embodiments, the multiplex detection method is for determining the presence or absence of each of each of *Lactobacillus* sp. and *G. vaginalis* in a sample. The method generally includes the following steps:

(1) contacting a sample, the sample suspected of containing at least one of *Lactobacillus* sp. and *G. vaginalis*, with (a) first and second *Lactobacillus*-specific amplification oligomers for amplifying a target region of a *Lactobacillus* sp. target nucleic acid, where (i) the first *Lactobacillus*-specific amplification oligomer comprises a first *Lactobacillus*-specific target-hybridizing sequence substantially corresponding to the nucleotide sequence of residues 28-45 of SEQ ID NO:7 or residues 28-45 of SEQ ID NO:8 and (ii) the second *Lactobacillus*-specific amplification oligomer comprises a second *Lactobacillus*-specific target-hybridizing sequence substantially corresponding to the nucleotide sequence of SEQ ID NO:6; and (b) first and second *G. vaginalis*-specific amplification oligomers for amplifying a target region of a *G. vaginalis* target nucleic acid, where (i) the first *G. vaginalis*-specific amplification oligomer comprises a first *G. vaginalis*-specific target-hybridizing sequence substantially corresponding to the nucleotide sequence of residues 28-45 of SEQ ID NO:13 and (ii) the second *G. vaginalis*-specific amplification oligomer comprises a second *G. vaginalis*-specific target-hybridizing sequence substantially corresponding to the nucleotide sequence of SEQ ID NO:12;

(2) performing an in vitro nucleic acid amplification reaction, where any *Lactobacillus* sp. and *G. vaginalis* target nucleic acid, if present in the sample, is used as a template for generating one or more amplification products corresponding to the *Lactobacillus* sp. and *G. vaginalis* target regions; and (3) detecting the presence or absence of the one or more amplification products, thereby determining the presence or absence of *Lactobacillus* sp. and *G. vaginalis* in the sample.

In some variations of a multiplex method as above, the first *Lactobacillus*-specific target-hybridizing sequence comprises the nucleotide sequence of residues 28-45 of SEQ ID NO:7 or residues 28-45 of SEQ ID NO:8; the second *Lactobacillus*-specific target-hybridizing sequence comprises the nucleotide sequence of SEQ ID NO:6; the first *G. vaginalis*-specific target-hybridizing sequence comprises the nucleotide sequence of residues 28-45 of SEQ ID NO:13; the second *G. vaginalis*-specific target-hybridizing sequence comprises the nucleotide sequence of SEQ ID NO:12; the first *Eggerthella*-specific target-hybridizing sequence comprises the nucleotide sequence of residues 28-51 of SEQ ID NO:17; and/or the second *Eggerthella*-specific target-hybridizing sequence comprises the nucleotide sequence of SEQ ID NO:16. In some such embodiments, the first *Lactobacillus*-specific target-hybridizing sequence consists of the nucleotide sequence of residues 28-45 of SEQ ID NO:7 or residues 28-45 of SEQ ID NO:8; the second *Lactobacillus*-specific target-hybridizing sequence consists of the nucleotide sequence of SEQ ID NO:6; the first *G. vaginalis*-specific target-hybridizing sequence consists of the nucleotide sequence of residues 28-45 of SEQ ID NO:13; the second *G. vaginalis*-specific target-hybridizing sequence consists of the nucleotide sequence of SEQ ID NO:12; the first *Eggerthella*-specific target-hybridizing sequence consists of the nucleotide sequence of residues 28-51 of SEQ ID NO:17; and/or the second *Eggerthella*-specific target-hybridizing sequence consists of the nucleotide sequence of SEQ ID NO:16.

In some variations of a multiplex method as above, the first *Lactobacillus*-specific target-hybridizing sequence substantially corresponds to the nucleotide sequence of residues 28-45 of SEQ ID NO:7, and the sample is further contacted with a third *Lactobacillus*-specific amplification oligomer for amplifying the *Lactobacillus* sp. target region, where the third *Lactobacillus*-specific amplification oligomer comprises a third *Lactobacillus*-specific target-hybridizing sequence substantially corresponding to the nucleotide sequence of residues 28-45 of SEQ ID NO:8. In some such embodiments, the third *Lactobacillus*-specific target-hybridizing sequence comprises the nucleotide sequence of residues 28-45 of SEQ ID NO:8. In a particular variation, the third *Lactobacillus*-specific target-hybridizing sequence consists of the nucleotide sequence of residues 28-45 of SEQ ID NO:8.

In some embodiments of a multiplex method as above, at least one of the first *Lactobacillus*-specific amplification oligomer, the first *G. vaginalis*-specific amplification oligomer, and the first *Eggerthella*-specific amplification oligomer (at least one of the first *Lactobacillus*-specific amplification oligomer and the first *G. vaginalis*-specific amplification oligomer) is a promoter primer or promoter provider further comprising a promoter sequence located 5' to the respective target hybridizing sequence. In some such embodiments where the first *Lactobacillus*-specific target-hybridizing sequence substantially corresponds to the nucleotide sequence of residues 28-45 of SEQ ID NO:7 and the sample is further contacted with a third *Lactobacillus*-specific amplification oligomer for amplifying the *Lactobacillus* sp. target region, the third *Lactobacillus*-specific amplification oligomer is a promoter primer or promoter provider further comprising a promoter sequence located 5' to the third *Lactobacillus*-specific target hybridizing sequence. A particularly suitable promoter sequence is a T7 promoter sequence such as, for example, a promoter sequence having the nucleotide sequence of residues 1-27 of SEQ ID NO:7. In specific variations, the first *Lactobacillus*-specific amplification oligomer has the nucleotide sequence of SEQ ID NO:7; the first *G. vaginalis*-specific amplification oligomer has the nucleotide sequence of SEQ ID NO:13; and/or the first *Eggerthella*-specific amplification oligomer has the nucleotide sequence of SEQ ID NO:17. In some embodiments as above where the sample is further contacted with a third *Lactobacillus*-specific amplification oligomer for amplifying the *Lactobacillus* sp. target region, the third *Lactobacillus*-specific amplification oligomer has the nucleotide sequence of SEQ ID NO:8.

In certain embodiments of a multiplex method as above, the method further includes purifying the *Lactobacillus*, *G. vaginalis*, and *Eggerthella* target nucleic acids, or purifying the *Lactobacillus* and *G. vaginalis* target nucleic acids, if present, from other components in the sample before step (2). In some such embodiments, the purifying step includes contacting the sample with at least one capture probe oligomer comprising a target-hybridizing sequence covalently attached to a sequence or moiety that binds to an immobilized probe. For example, the sample may be contacted with a *Lactobacillus*-specific capture probe oligomer, a *G. vaginalis*-specific capture probe oligomer, and an *Eggerthella*-specific capture probe oligomer, where each of the *Lactobacillus*-specific, *G. vaginalis*-specific, and *Eggerthella*-specific capture probe oligomers comprises a capture probe target-hybridizing sequence that specifically hybridizes to a target sequence within the *Lactobacillus*, *G. vaginalis*, or *Eggerthella* target nucleic acid, respectively, and where each of the *Lactobacillus*-specific, *G. vaginalis*-specific, and *Eggerthella*-specific capture probe target-hybridizing sequences is covalently attached to the sequence or moiety that binds to the immobilized probe. In some embodiments directed to detection of *Lactobacillus* sp. and *G. vaginalis*, the sample may be contacted with a *Lactobacillus*-specific capture probe oligomer and a *G. vaginalis*-specific capture probe oligomer, where each of the *Lactobacillus*-specific and *G. vaginalis*-specific capture probe oligomers comprises a capture probe target-hybridizing sequence that specifically hybridizes to a target sequence within the *Lactobacillus* or *G. vaginalis* target nucleic acid, respectively, and where each of the *Lactobacillus*-specific and *G. vaginalis*-specific capture probe target-hybridizing sequences is covalently attached to the sequence or moiety that binds to the immobilized probe. In specific variations, the *Lactobacillus*-specific capture probe target-hybridizing sequence substantially corresponds to the nucleotide sequence of residues 1-12 of SEQ ID NO:5, the *G. vaginalis*-specific capture probe target-hybridizing sequence substantially corresponds to the nucleotide sequence of residues 1-17 of SEQ ID NO:11, and/or the *Eggerthella*-specific capture probe target hybridizing sequence substantially corresponds to the nucleotide sequence of residues 1-21 of SEQ ID NO:15. In some embodiments, the *Lactobacillus*-specific capture probe oligomer has the nucleotide sequence of SEQ ID NO:5, the *G. vaginalis*-specific capture probe oligomer has the nucleotide sequence of SEQ ID NO:11, and/or the *Eggerthella*-specific capture probe oligomer has the nucleotide sequence of SEQ ID NO:15.

In some embodiments of a multiplex method as above, the detecting step (3) includes (i) contacting the one or more amplification products with a first *Lactobacillus*-specific detection probe that specifically hybridizes to the *Lactobacillus* sp. target region, a first *G. vaginalis*-specific detection probe that specifically hybridizes to the *G. vaginalis* target region, and a first *Eggerthella*-specific detection probe that specifically hybridizes to the *Eggerthella* sp. target region, and (ii) detecting the presence or absence of any target-hybridized *Lactobacillus*-specific, *G. vaginalis*-specific, and/or *Eggerthella*-specific detection probe. In some embodiments of a multiplex method for detection of *Lactobacillus* sp. and *G. vaginalis* as above, the detecting step (3) includes (i) contacting the one or more amplification products with a first *Lactobacillus*-specific detection probe that specifically hybridizes to the *Lactobacillus* sp. target region and a first *G. vaginalis*-specific detection probe that specifically hybridizes to the *G. vaginalis* target region, and (ii) detecting the presence or absence of any target-hybridized *Lactobacillus*-specific and/or *G. vaginalis*-specific detection probe. In some embodiments, the first *Lactobacillus*-specific detection probe comprises a target-hybridizing sequence substantially corresponding to SEQ ID NO:9, the first *G. vaginalis*-specific detection probe comprises a target-hybridizing sequence substantially corresponding to residues 1-19 of SEQ ID NO:14, and/or the first *Eggerthella*-specific detection probe comprises a target-hybridizing sequence substantially corresponding to SEQ ID NO:18. In specific variations, the first *Lactobacillus*-specific detection probe has the nucleotide sequence of SEQ ID NO:9, the first *G. vaginalis*-specific detection probe has the nucleotide sequence of SEQ ID NO:14, and/or the first *Eggerthella*-specific detection probe has the nucleotide sequence of SEQ ID NO:18. In some embodiments as above, the detecting step (3) further includes contacting the one or more amplification products with a second *Lactobacillus*-specific detection probe that specifically hybridizes to the *Lactobacillus* sp. target region, where the second *Lactobacillus*-specific detection probe comprises a target-hybridizing sequence substantially corresponding to residues 6-21 of SEQ ID NO:10; in some such embodiments, the second *Lactobacillus*-specific detection probe has the nucleotide sequence of SEQ ID NO:10.

In certain embodiments of a multiplex method comprising the use of a first *Lactobacillus*-specific detection probe, a first *G. vaginalis*-specific detection probe, and a first *Eggerthella*-specific detection probe (or the use of a first *Lactobacillus*-specific detection probe and a first *G. vaginalis*-specific detection probe) as above, each of the probes comprises a label. In some embodiments further including contacting the one or more amplification products with a second *Lactobacillus*-specific detection probe, the second *Lactobacillus*-specific detection probe comprises a label. Particularly suitable labels include chemiluminescent and fluorescent labels.

In some embodiments of a multiplex method comprising the use of labeled detection probes as above, the detecting step (3) occurs during the amplifying step (2). In some such variations, each detection probe comprises a fluorescent label and a quencher. Particularly suitable detection probes comprising a fluorescent label and a quencher include a molecular torch, a molecular beacon, and a TaqMan detection probe.

In certain embodiments of a multiplex method comprising the use of detection probes as above, at least one of the first *Lactobacillus*-specific detection probe, the first *G. vaginalis*-specific detection probe, and the first *Eggerthella*-specific detection probe (or at least one of the first *Lactobacillus*-specific detection probe and the first *G. vaginalis*-specific detection probe) further comprises a non-target-hybridizing sequence. In some embodiments further including contacting the one or more amplification products with a second *Lactobacillus*-specific detection probe, the second *Lactobacillus*-specific detection probe further comprises a non-target-hybridizing sequence. In some such variations as above, any one of (e.g., each of) the detection probes is a molecular torch or a molecular beacon.

In some embodiments of a multiplex method as above, the amplification reaction at step (2) is an isothermal amplification reaction. In particular variations, the isothermal amplification reaction is a transcription-mediated amplification (TMA) reaction. In certain embodiments, the isothermal amplification reaction is a real-time amplification reaction.

In another aspect, the present invention provides an oligomer combination. In some embodiments, the oligomer combination is for determining the presence or absence of each of each of *Lactobacillus* sp., *G. vaginalis*, and *Eggerthella* sp. in a sample. The oligomer combination generally includes the following oligomers:

(a) first and second *Lactobacillus*-specific amplification oligomers for amplifying a target region of a *Lactobacillus* sp. target nucleic acid, where (i) the first *Lactobacillus*-specific amplification oligomer comprises a first *Lactobacillus*-specific target-hybridizing sequence substantially corresponding to the nucleotide sequence of residues 28-45 of SEQ ID NO:7 or residues 28-45 of SEQ ID NO:8 and (ii) the second *Lactobacillus*-specific amplification oligomer comprises a second *Lac-* tobacillus-specific target-hybridizing sequence substantially corresponding to the nucleotide sequence of SEQ ID NO:6;

(b) first and second *G. vaginalis*-specific amplification oligomers for amplifying a target region of a *G. vaginalis* target nucleic acid, where (i) the first *G. vaginalis*-specific amplification oligomer comprises a first *G. vaginalis*-specific target-hybridizing sequence substantially corresponding to the nucleotide sequence of residues 28-45 of SEQ ID NO:13 and (ii) the second *G. vaginalis*-specific amplification oligomer comprises a second *G. vaginalis*-specific target-hybridizing sequence substantially corresponding to the nucleotide sequence of SEQ ID NO:12; and (c) first and second *Eggerthella*-specific amplification oligomers for amplifying a target region of an *Eggerthella* sp. target nucleic acid, where (i) the first *Eggerthella*-specific amplification oligomer comprises a first *Eggerthella*-specific target-hybridizing sequence substantially corresponding to the nucleotide sequence of residues 28-51 of SEQ ID NO:17 and (ii) the second *Eggerthella*-specific amplification oligomer comprises a second *Eggerthella*-specific target-hybridizing sequence substantially corresponding to the nucleotide sequence of SEQ ID NO:16.

In other embodiments, the oligomer combination is for determining the presence or absence of each of each of *Lactobacillus* sp. and *G. vaginalis* in a sample. The oligomer combination generally includes the following oligomers:

(a) first and second *Lactobacillus*-specific amplification oligomers for amplifying a target region of a *Lactobacillus* sp. target nucleic acid, where (i) the first *Lactobacillus*-specific amplification oligomer comprises a first *Lactobacillus*-specific target-hybridizing sequence substantially corresponding to the nucleotide sequence of residues 28-45 of SEQ ID NO:7 or residues 28-45 of SEQ ID NO:8 and (ii) the second *Lactobacillus*-specific amplification oligomer comprises a second *Lactobacillus*-specific target-hybridizing sequence substantially corresponding to the nucleotide sequence of SEQ ID NO:6; and (b) first and second *G. vaginalis*-specific amplification oligomers for amplifying a target region of a *G. vaginalis* target nucleic acid, where (i) the first *G. vaginalis*-specific amplification oligomer comprises a first *G. vaginalis*-specific target-hybridizing sequence substantially corresponding to the nucleotide sequence of residues 28-45 of SEQ ID NO:13 and (ii) the second *G. vaginalis*-specific amplification oligomer comprises a second *G. vaginalis*-specific target-hybridizing sequence substantially corresponding to the nucleotide sequence of SEQ ID NO:12.

In some variations of an oligomer combination as above, the first *Lactobacillus*-specific target-hybridizing sequence comprises the nucleotide sequence of residues 28-45 of SEQ ID NO:7 or residues 28-45 of SEQ ID NO:8; the second *Lactobacillus*-specific target-hybridizing sequence comprises the nucleotide sequence of SEQ ID NO:6; the first *G. vaginalis*-specific target-hybridizing sequence comprises the nucleotide sequence of residues 28-45 of SEQ ID NO:13; the second *G. vaginalis*-specific target-hybridizing sequence comprises the nucleotide sequence of SEQ ID NO:12; the first *Eggerthella*-specific target-hybridizing sequence comprises the nucleotide sequence of residues 28-51 of SEQ ID NO:17; and/or the second *Eggerthella*-specific target-hybridizing sequence comprises the nucleotide sequence of SEQ ID NO:16. In some such embodiments, the first *Lac-*

*tobacillus*-specific target-hybridizing sequence consists of the nucleotide sequence of residues 28-45 of SEQ ID NO:7 or residues 28-45 of SEQ ID NO:8; the second *Lactobacillus*-specific target-hybridizing sequence consists of the nucleotide sequence of SEQ ID NO:6; the first *G. vaginalis*-specific target-hybridizing sequence consists of the nucleotide sequence of residues 28-45 of SEQ ID NO:13; the second *G. vaginalis*-specific target-hybridizing sequence consists of the nucleotide sequence of SEQ ID NO:12; the first *Eggerthella*-specific target-hybridizing sequence consists of the nucleotide sequence of residues 28-51 of SEQ ID NO:17; and/or the second *Eggerthella*-specific target-hybridizing sequence consists of the nucleotide sequence of SEQ ID NO:16.

In some variations of an oligomer combination as above, the first *Lactobacillus*-specific target-hybridizing sequence substantially corresponds to the nucleotide sequence of residues 28-45 of SEQ ID NO:7, and the oligomer combination further includes a third *Lactobacillus*-specific amplification oligomer for amplifying the *Lactobacillus* sp. target region, where the third *Lactobacillus*-specific amplification oligomer comprises a third *Lactobacillus*-specific target-hybridizing sequence substantially corresponding to the nucleotide sequence of residues 28-45 of SEQ ID NO:8. In some such embodiments, the third *Lactobacillus*-specific target-hybridizing sequence comprises the nucleotide sequence of residues 28-45 of SEQ ID NO:8. In a particular variation, the third *Lactobacillus*-specific target-hybridizing sequence consists of the nucleotide sequence of residues 28-45 of SEQ ID NO:8.

In some embodiments of an oligomer combination as above, at least one of the first *Lactobacillus*-specific amplification oligomer, the first *G. vaginalis*-specific amplification oligomer, and the first *Eggerthella*-specific amplification oligomer (or at least one of the first *Lactobacillus*-specific amplification oligomer and the first *G. vaginalis*-specific amplification oligomer) is a promoter primer or promoter provider further comprising a promoter sequence located 5' to the respective target hybridizing sequence. In some such embodiments where the first *Lactobacillus*-specific target-hybridizing sequence substantially corresponds to the nucleotide sequence of residues 28-45 of SEQ ID NO:7 and the sample is further contacted with a third *Lactobacillus*-specific amplification oligomer for amplifying the *Lactobacillus* sp. target region, the third *Lactobacillus*-specific amplification oligomer is a promoter primer or promoter provider further comprising a promoter sequence located 5' to the third *Lactobacillus*-specific target hybridizing sequence. A particularly suitable promoter sequence is a T7 promoter sequence such as, for example, a promoter sequence having the nucleotide sequence of residues 1-27 of SEQ ID NO:7. In specific variations, the first *Lactobacillus*-specific amplification oligomer has the nucleotide sequence of SEQ ID NO:7; the first *G. vaginalis*-specific amplification oligomer has the nucleotide sequence of SEQ ID NO:13; and/or the first *Eggerthella*-specific amplification oligomer has the nucleotide sequence of SEQ ID NO:17. In some embodiments as above where the sample is further contacted with a third *Lactobacillus*-specific amplification oligomer for amplifying the *Lactobacillus* sp. target region, the third *Lactobacillus*-specific amplification oligomer has the nucleotide sequence of SEQ ID NO:8.

In certain embodiments of an oligomer combination as above, the oligomer combination further includes at least one capture probe oligomer comprising a target-hybridizing sequence covalently attached to a sequence or moiety that binds to an immobilized probe. For example, the oligomer combination may include a *Lactobacillus*-specific capture probe oligomer, a *G. vaginalis*-specific capture probe oligomer, and an *Eggerthella*-specific capture probe oligomer, where each of the *Lactobacillus*-specific, *G. vaginalis*-specific, and *Eggerthella*-specific capture probe oligomers comprises a capture probe target-hybridizing sequence that specifically hybridizes to a target sequence within the *Lactobacillus*, *G. vaginalis*, or *Eggerthella* target nucleic acid, respectively, and where each of the *Lactobacillus*-specific, *G. vaginalis*-specific, and *Eggerthella*-specific capture probe target-hybridizing sequences is covalently attached to the sequence or moiety that binds to the immobilized probe. In some embodiments directed to an oligomer combination for determining the presence or absence of each of each of *Lactobacillus* sp. and *G. vaginalis*, the oligomer combination may include a *Lactobacillus*-specific capture probe oligomer and a *G. vaginalis*-specific capture probe oligomer, where each of the *Lactobacillus*-specific and *G. vaginalis*-specific capture probe oligomers comprises a capture probe target-hybridizing sequence that specifically hybridizes to a target sequence within the *Lactobacillus* or *G. vaginalis* target nucleic acid, respectively, and where each of the *Lactobacillus*-specific and *G. vaginalis*-specific capture probe target-hybridizing sequences is covalently attached to the sequence or moiety that binds to the immobilized probe. In specific variations, the *Lactobacillus*-specific capture probe target-hybridizing sequence substantially corresponds to the nucleotide sequence of residues 1-12 of SEQ ID NO:5, the *G. vaginalis*-specific capture probe target-hybridizing sequence substantially corresponds to the nucleotide sequence of residues 1-17 of SEQ ID NO:11, and/or the *Eggerthella*-specific capture probe target hybridizing sequence substantially corresponds to the nucleotide sequence of residues 1-21 of SEQ ID NO:15. In some embodiments, the *Lactobacillus*-specific capture probe oligomer has the nucleotide sequence of SEQ ID NO:5, the *G. vaginalis*-specific capture probe oligomer has the nucleotide sequence of SEQ ID NO:11, and/or the *Eggerthella*-specific capture probe oligomer has the nucleotide sequence of SEQ ID NO:15.

In some embodiments of an oligomer combination as above, the oligomer combination further includes a first *Lactobacillus*-specific detection probe that specifically hybridizes to the *Lactobacillus* sp. target region, a first *G. vaginalis*-specific detection probe that specifically hybridizes to the *G. vaginalis* target region, and a first *Eggerthella*-specific detection probe that specifically hybridizes to the *Eggerthella* sp. target region. In some embodiments of an oligomer combination for determining the presence or absence of each of each of *Lactobacillus* sp. and *G. vaginalis* as above, the oligomer combination further includes a first *Lactobacillus*-specific detection probe that specifically hybridizes to the *Lactobacillus* sp. target region and a first *G. vaginalis*-specific detection probe that specifically hybridizes to the *G. vaginalis* target region. In some embodiments, the first *Lactobacillus*-specific detection probe comprises a target-hybridizing sequence substantially corresponding to SEQ ID NO:9, the first *G. vaginalis*-specific detection probe comprises a target-hybridizing sequence substantially corresponding to residues 1-19 of SEQ ID NO:14, and/or the first *Eggerthella*-specific detection probe comprises a target-hybridizing sequence substantially corresponding to SEQ ID NO:18. In specific variations, the first *Lactobacillus*-specific detection probe has the nucleotide sequence of SEQ ID NO:9, the first *G. vaginalis*-specific detection probe has the nucleotide sequence of SEQ ID NO:14, and/or the first *Eggerthella*-specific detection probe has the nucleotide sequence of SEQ ID NO:18. In some embodiments as above, the oligomer combination further includes a second *Lactobacillus*-specific detection probe that specifically hybridizes to the *Lactobacillus* sp. target region, where the second *Lactobacillus*-specific detection probe comprises a target-hybridizing sequence substantially corresponding to residues 6-21 of SEQ ID NO:10; in some such embodiments, the second *Lactobacillus*-specific detection probe has the nucleotide sequence of SEQ ID NO:10.

In certain embodiments of an oligomer combination comprising a first *Lactobacillus*-specific detection probe, a first *G. vaginalis*-specific detection probe, and a first *Eggerthella*-specific detection probe (or a first *Lactobacillus*-specific detection probe and a first *G. vaginalis*-specific detection probe) as above, each of the probes comprises a label. In some embodiments further including a second *Lactobacillus*-specific detection probe, the second *Lactobacillus*-specific detection probe comprises a label. Particularly suitable labels include chemiluminescent and fluorescent labels.

In some embodiments of an oligomer combination comprising labeled detection probes as above, each detection probe comprises a fluorescent label and a quencher. Particularly suitable detection probes comprising a fluorescent label and a quencher include a molecular torch, a molecular beacon, and a TaqMan detection probe.

In certain embodiments of an oligomer combination comprising detection probes as above, at least one of the first *Lactobacillus*-specific detection probe, the first *G. vaginalis*-specific detection probe, and the first *Eggerthella*-specific detection probe (or at least one of the first *Lactobacillus*-specific detection probe and the first *G. vaginalis*-specific detection probe) further comprises a non-target-hybridizing sequence. In some embodiments further including a second *Lactobacillus*-specific detection probe, the second *Lactobacillus*-specific detection probe further comprises a non-target-hybridizing sequence. In some such variations as above, any one of (e.g., each of) the detection probes is a molecular torch or a molecular beacon.

In yet another aspect, the present invention provides a method for determining the presence or absence of *Lactobacillus* sp. in a sample. The method generally includes the following steps:

(1) contacting a sample, the sample suspected of containing *Lactobacillus* sp., with first and second *Lactobacillus*-specific amplification oligomers for amplifying a target region of a *Lactobacillus* sp. target nucleic acid, where the first and second *Lactobacillus*-specific amplification oligomers respectively comprise first and second *Lactobacillus*-specific target-hybridizing sequences, and where the first and second amplification oligomers target a *Lactobacillus* sp. 16S rRNA region corresponding to a region of SEQ ID NO:1 from about nucleotide position 91 to about nucleotide position 265;

(2) performing an in vitro nucleic acid amplification reaction, where any *Lactobacillus* sp. target nucleic acid, if present in the sample, is used as a template for generating one or more amplification products corresponding to the *Lactobacillus* sp. target region; and (3) detecting the presence or absence of the one or more amplification products, thereby determining the presence or absence of *Lactobacillus* sp. in the sample.

In some variations of a method for detecting *Lactobacillus* sp. as above, the first *Lactobacillus*-specific target-hybridizing sequence substantially corresponds to the nucleotide sequence of residues 28-45 of SEQ ID NO:7 or residues 28-45 of SEQ ID NO:8, and/or the second *Lacto-*

*bacillus*-specific target-hybridizing sequence substantially corresponds to the nucleotide sequence of SEQ ID NO:6. In some such embodiments, the first *Lactobacillus*-specific target-hybridizing sequence comprises or consists of the nucleotide sequence of residues 28-45 of SEQ ID NO:7 or residues 28-45 of SEQ ID NO:8, and/or the second *Lactobacillus*-specific target-hybridizing sequence comprises or consists of the nucleotide sequence of SEQ ID NO:6.

In some embodiments of a method for detecting *Lactobacillus* sp. as above, the first *Lactobacillus*-specific target-hybridizing sequence substantially corresponds to the nucleotide sequence of residues 28-45 of SEQ ID NO:7, and the sample is further contacted with a third *Lactobacillus*-specific amplification oligomer for amplifying the *Lactobacillus* sp. target region, where the third *Lactobacillus*-specific amplification oligomer comprises a third *Lactobacillus*-specific target-hybridizing sequence substantially corresponding to the nucleotide sequence of residues 28-45 of SEQ ID NO:8. In some such embodiments, the third *Lactobacillus*-specific target-hybridizing sequence comprises or consists of the nucleotide sequence of residues 28-45 of SEQ ID NO:8.

In some embodiments of a method for detecting *Lactobacillus* sp. as above, the first *Lactobacillus*-specific amplification oligomer further comprises a promoter sequence located 5' to the first *Lactobacillus*-specific target hybridizing sequence. In some such embodiments, where the first *Lactobacillus*-specific target-hybridizing sequence substantially corresponds to the nucleotide sequence of residues 28-45 of SEQ ID NO:7 and the sample is further contacted with a third *Lactobacillus*-specific amplification oligomer for amplifying the *Lactobacillus* sp. target region, the third *Lactobacillus*-specific amplification oligomer is a promoter primer or promoter provider further comprising a promoter sequence located 5' to the third *Lactobacillus*-specific target hybridizing sequence. A particularly suitable promoter sequence is a T7 promoter sequence such as, for example, a promoter sequence having the nucleotide sequence of residues 1-27 of SEQ ID NO:7. In specific variations, the first *Lactobacillus*-specific amplification oligomer has the nucleotide sequence of SEQ ID NO:7. In some embodiments as above where the sample is further contacted with a third *Lactobacillus*-specific amplification oligomer for amplifying the *Lactobacillus* sp. target region, the third *Lactobacillus*-specific amplification oligomer has the nucleotide sequence of SEQ ID NO:8.

In certain embodiments of a method for detecting *Lactobacillus* sp. as above, the method further includes purifying the *Lactobacillus* target nucleic acid, if present, from other components in the sample before step (2). In some such embodiments, the purifying step includes contacting the sample with at least one capture probe oligomer comprising a target-hybridizing sequence covalently attached to a sequence or moiety that binds to an immobilized probe. For example, the sample may be contacted with a *Lactobacillus*-specific capture probe oligomer comprising a capture probe target-hybridizing sequence that specifically hybridizes to a target sequence within the *Lactobacillus* target nucleic acid, where the *Lactobacillus*-specific capture probe target-hybridizing sequence is covalently attached to the sequence or moiety that binds to the immobilized probe. In specific variations, the *Lactobacillus*-specific capture probe target-hybridizing sequence substantially corresponds to the nucleotide sequence of residues 1-12 of SEQ ID NO:5. In some embodiments, the *Lactobacillus*-specific capture probe oligomer has the nucleotide sequence of SEQ ID NO:5.

In some embodiments of a method for detecting *Lactobacillus* sp. as above, the detecting step (3) includes (i) contacting the one or more amplification products with a first *Lactobacillus*-specific detection probe that specifically hybridizes to the *Lactobacillus* sp. target region, and (ii) detecting the presence or absence of any target-hybridized *Lactobacillus*-specific detection probe. In some such embodiments, the first *Lactobacillus*-specific detection probe comprises a target-hybridizing sequence substantially corresponding to SEQ ID NO:9. In a specific variation, the first *Lactobacillus*-specific detection probe has the nucleotide sequence of SEQ ID NO:9. In some embodiments as above, the detecting step (3) further includes contacting the one or more amplification products with a second *Lactobacillus*-specific detection probe that specifically hybridizes to the *Lactobacillus* sp. target region, where the second *Lactobacillus*-specific detection probe comprises a target-hybridizing sequence substantially corresponding to residues 6-21 of SEQ ID NO:10; in some such embodiments, the second *Lactobacillus*-specific detection probe has the nucleotide sequence of SEQ ID NO:10.

In certain embodiments of a method for detecting *Lactobacillus* sp. as above, where the method includes the use of a first *Lactobacillus*-specific detection probe, the first *Lactobacillus*-specific detection probe comprises a label. In some embodiments further including contacting the one or more amplification products with a second *Lactobacillus*-specific detection probe, the second *Lactobacillus*-specific detection probe comprises a label. Particularly suitable labels include chemiluminescent and fluorescent labels.

In some embodiments of a method for detecting *Lactobacillus* sp. as above, where the method includes the use of a labeled detection probe, the detecting step (3) occurs during the amplifying step (2). In some such variations, the detection probe comprises a fluorescent label and a quencher. Particularly suitable detection probes comprising a fluorescent label and a quencher include a molecular torch, a molecular beacon, and a TaqMan detection probe.

In certain embodiments of a method for detecting *Lactobacillus* sp. as above, where the method includes the use of a labeled detection probe, the first *Lactobacillus*-specific detection probe further comprises a non-target-hybridizing sequence. In some variations of the method, the first *Lactobacillus*-specific detection probe is a molecular torch or a molecular beacon.

In yet another aspect, the present invention provides a method for determining the presence or absence of *G. vaginalis* in a sample. The method generally includes the following steps:

(1) contacting a sample, the sample suspected of containing *G. vaginalis*, with first and second *G. vaginalis*-specific amplification oligomers for amplifying a target region of a *G. vaginalis* target nucleic acid, where the first and second *G. vaginalis*-specific amplification oligomers respectively comprise first and second *G. vaginalis*-specific target hybridizing sequences, and where the first and second amplification oligomers target a *G. vaginalis* 16S rRNA region corresponding to a region of SEQ ID NO:3 from about nucleotide position 964 to about nucleotide position 1036;

(2) performing an in vitro nucleic acid amplification reaction, where any *G. vaginalis* target nucleic acid, if present in the sample, is used as a template for generating one or more amplification products corresponding to the *G. vaginalis* target region; and (3) detecting the presence or absence of the one or more amplification products, thereby determining the presence or absence of *G. vaginalis* in the sample.

In some variations of a method for detecting *G. vaginalis* as above, the first *G. vaginalis*-specific target-hybridizing sequence substantially corresponds to the nucleotide sequence of residues 28-45 of SEQ ID NO:13, and/or the second *G. vaginalis*-specific target-hybridizing sequence substantially corresponds to the nucleotide sequence of SEQ ID NO:12. In some such embodiments, the first *G. vaginalis*-specific target-hybridizing sequence comprises or consists of the nucleotide sequence of residues 28-45 of SEQ ID NO:13, and/or the second *G. vaginalis*-specific target-hybridizing sequence comprises or consists of the nucleotide sequence of SEQ ID NO:12.

In some embodiments of a method for detecting *G. vaginalis* as above, the first *G. vaginalis*-specific amplification oligomer is a promoter primer or promoter provider further comprising a promoter sequence located 5' to the first *G. vaginalis*-specific target hybridizing sequence. A particularly suitable promoter sequence is a T7 promoter sequence such as, for example, a promoter sequence having the nucleotide sequence of residues 1-27 of SEQ ID NO:7. In specific variations, the first *G. vaginalis*-specific amplification oligomer has the nucleotide sequence of SEQ ID NO:13.

In certain embodiments of a method for detecting *G. vaginalis* as above, the method further includes purifying the *G. vaginalis* target nucleic acid, if present, from other components in the sample before step (2). In some embodiments, the purifying step further includes contacting the sample with at least one capture probe oligomer comprising a target-hybridizing sequence covalently attached to a sequence or moiety that binds to an immobilized probe. For example, the sample may be contacted with a *G. vaginalis*-specific capture probe oligomer comprising a capture probe target-hybridizing sequence that specifically hybridizes to a target sequence within the *G. vaginalis* target nucleic acid, where the *G. vaginalis*-specific capture probe target-hybridizing sequence is covalently attached to the sequence or moiety that binds to the immobilized probe. In specific variations, the *G. vaginalis*-specific capture probe target-hybridizing sequence substantially corresponds to the nucleotide sequence of residues 1-17 of SEQ ID NO:11. In some embodiments, the *G. vaginalis*-specific capture probe oligomer has the nucleotide sequence of SEQ ID NO:11.

In some embodiments of a method for detecting *G. vaginalis* as above, the detecting step (3) includes (i) contacting the one or more amplification products with a first *G. vaginalis*-specific detection probe that specifically hybridizes to the *G. vaginalis* target region, and (ii) detecting the presence or absence of any target-hybridized *G. vaginalis*-specific detection probe. In some such embodiments, the first *G. vaginalis*-specific detection probe comprises a target-hybridizing sequence substantially corresponding to residues 1-19 of SEQ ID NO:14. In a specific variation, the first *G. vaginalis*-specific detection probe has the nucleotide sequence of SEQ ID NO:14.

In certain embodiments of a method for detecting *G. vaginalis* as above, the first *G. vaginalis*-specific detection probe detection probe comprises a label. Particularly suitable labels include chemiluminescent and fluorescent labels.

In some embodiments of a method for detecting *G. vaginalis* as above, where the method includes the use of a labeled detection probe, the detecting step (3) occurs during the amplifying step (2). In some such variations, the detection probe comprises a fluorescent label and a quencher. Particularly suitable detection probes comprising a fluorescent label and a quencher include a molecular torch, a molecular beacon, or a TaqMan detection probe.

In certain embodiments of a method for detecting *G. vaginalis* as above, where the method includes the use of a labeled detection probe, the first *G. vaginalis*-specific detection probe further comprises a non-target-hybridizing sequence. In some variations of the method, the first *G. vaginalis*-specific detection probe is a molecular torch or a molecular beacon.

In still another aspect, the present invention provides a method for determining the presence or absence of *Eggerthella* sp. in a sample. The method generally includes the following steps:

(1) contacting a sample, the sample suspected of containing *Eggerthella* sp., with first and second *Eggerthella*-specific amplification oligomers for amplifying a target region of a *Eggerthella* sp. target nucleic acid, where the first and second *Eggerthella*-specific amplification oligomers respectively comprise first and second *Eggerthella*-specific target-hybridizing sequences, and where the first and second amplification oligomers target a *Eggerthella* sp. 16S rRNA region corresponding to a region of SEQ ID NO:4 from about nucleotide position 165 to about nucleotide position 259;

(2) performing an in vitro nucleic acid amplification reaction, wherein any *Eggerthella* sp. target nucleic acid, if present in the sample, is used as a template for generating one or more amplification products corresponding to the *Eggerthella* sp. target region; and (3) detecting the presence or absence of the one or more amplification products, thereby determining the presence or absence of *Eggerthella* sp. in the sample.

In some variations of a method for detecting *Eggerthella* sp. as above, the first *Eggerthella*-specific target-hybridizing sequence substantially corresponds to the nucleotide sequence of residues 28-51 of SEQ ID NO:17, and/or the second *Eggerthella*-specific target-hybridizing sequence substantially corresponds to the nucleotide sequence of SEQ ID NO:16. In some such embodiments, the first *Eggerthella*-specific target-hybridizing sequence comprises or consists of the nucleotide sequence of residues 28-51 of SEQ ID NO:17, and/or the second *Eggerthella*-specific target-hybridizing sequence comprises or consists of the nucleotide sequence of SEQ ID NO:16.

In some embodiments of a method for detecting *Eggerthella* sp. as above, the first *Eggerthella*-specific amplification oligomer is a promoter primer or promoter provider further comprising a promoter sequence located 5' to the first *Eggerthella*-specific target hybridizing sequence. A particularly suitable promoter sequence is a T7 promoter sequence such as, for example, a promoter sequence having the nucleotide sequence of residues 1-27 of SEQ ID NO:7. In specific variations, the first *Eggerthella*-specific amplification oligomer has the nucleotide sequence of SEQ ID NO:17.

In certain embodiments of a method for detecting *Eggerthella* sp. as above, the method further includes purifying the *Eggerthella* sp. target nucleic acid, if present, from other components in the sample before step (2). In some embodiments, the purifying step further includes contacting the sample with at least one capture probe oligomer comprising a target-hybridizing sequence covalently attached to a sequence or moiety that binds to an immobilized probe. For example, the sample may be contacted with a *Eggerthella*-specific capture probe oligomer comprising a capture probe target-hybridizing sequence that specifically hybridizes to a target sequence within the *Eggerthella* sp. target nucleic acid, where the *Eggerthella*-specific capture probe target-hybridizing sequence is covalently attached to the sequence or moiety that binds to the immobilized probe. In specific variations, the *Eggerthella*-specific capture probe target-hybridizing sequence substantially corresponds to the nucleotide sequence of residues 1-21 of SEQ ID NO:15. In some embodiments, the *Eggerthella*-specific capture probe oligomer has the nucleotide sequence of SEQ ID NO:15.

In some embodiments of a method for detecting *Eggerthella* sp. as above, the detecting step (3) includes (i) contacting the one or more amplification products with a first *Eggerthella*-specific detection probe that specifically hybridizes to the *Eggerthella* sp. target region, and (ii) detecting the presence or absence of any target-hybridized *Eggerthella*-specific detection probe. In some such embodiments, the first *Eggerthella*-specific detection probe comprises a target-hybridizing sequence substantially corresponding to SEQ ID NO:18. In a specific variation, the first *Eggerthella*-specific detection probe has the nucleotide sequence of SEQ ID NO:18.

In certain embodiments of a method for detecting *Eggerthella* sp. as above, the first *Eggerthella*-specific detection probe detection probe comprises a label. Particularly suitable labels include chemiluminescent and fluorescent labels.

In some embodiments of a method for detecting *Eggerthella* sp. as above, where the method includes the use of a labeled detection probe, the detecting step (3) occurs during the amplifying step (2). In some such variations, the detection probe comprises a fluorescent label and a quencher. Particularly suitable detection probes comprising a fluorescent label and a quencher include a molecular torch, a molecular beacon, or a TaqMan detection probe.

In certain embodiments of a method for detecting *Eggerthella* sp. as above, where the method includes the use of a labeled detection probe, the first *Eggerthella*-specific detection probe further comprises a non-target-hybridizing sequence. In some variations of the method, the first *Eggerthella*-specific detection probe is a molecular torch or a molecular beacon.

In some embodiments of a method for detecting any one of *Lactobacillus* sp., *G. vaginalis*, or *Eggerthella* sp. as above, the amplification reaction at step (2) is an isothermal amplification reaction. In particular variations, the isothermal amplification reaction is a transcription-mediated amplification (TMA) reaction. In certain embodiments, the isothermal amplification reaction is a real-time amplification reaction.

In still other aspects, the present invention provides an oligomer combination for determining the presence or absence of any one of *Lactobacillus* sp., *G. vaginalis*, and *Eggerthella* sp. in a sample. In various embodiments, the oligomer combination includes oligomers as set forth above for a method for determining the presence or absence of *Lactobacillus* sp., *G. vaginalis*, and *Eggerthella* sp. in a sample.

In yet other aspects, the present invention provides a composition or a kit for determining the presence or absence of Bacterial Vaginosis (BV) in a subject. The composition or kit generally includes (a) a first detection probe that specifically hybridizes to a *Lactobacillus* sp. target nucleic acid, and (b) a second detection probe that specifically hybridizes to a *G. vaginalis* target nucleic acid, where at least one of the first and second detection probes comprises a label, and where the composition or kit (i) does not comprise a detection probe that specifically hybridizes to a target nucleic acid from any fungal species and (ii) does not comprise a detection probe that specifically hybridizes to a target nucleic acid from any bacterial species other than *Lactobacillus* sp. or *G. vaginalis*. In some embodiments, the first detection probe specifically hybridizes to at least one of an *L. gasseri* target nucleic acid, an *L. crispatus* target nucleic acid, and an *L. jensenii* target nucleic acid. In some embodiments, the first detection probe targets a *Lactobacillus* sp. 16S rRNA region corresponding to a region of SEQ ID NO:1 from about nucleotide position 91 to about nucleotide position 265, and/or the second detection probe targets a *G. vaginalis* 16S rRNA region corresponding to a region of SEQ ID NO:3 from about nucleotide position 964 to about nucleotide position 1036. In particular variations, the first detection probe comprises a target-hybridizing sequence substantially corresponding to SEQ ID NO:9 and/or the second detection probe comprises a target-hybridizing sequence substantially corresponding to residues 1-19 of SEQ ID NO:14; in some such embodiments, the first detection probe has the nucleotide sequence of SEQ ID NO:9 and/or the second detection probe has the nucleotide sequence of SEQ ID NO:14. In certain embodiments, the composition or kit further includes a third detection probe that specifically hybridizes to the *Lactobacillus* sp. target nucleic acid, e.g., a third detection probe comprising a target-hybridizing sequence that substantially corresponds to residues 6-21 of SEQ ID NO:10. In a specific variation, the third detection probe has the nucleotide sequence of SEQ ID NO:10.

These and other aspects of the invention will become evident upon reference to the following detailed description of the invention.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

"Sample" includes any specimen that may contain *Lactobacillus* sp., *Gardnerella vaginalis*, or *Eggerthella* sp. or components thereof, such as nucleic acids or fragments of nucleic acids. Samples include "biological samples" which include any tissue or material derived from a living or dead human that may contain *Lactobacillus* sp., *Gardnerella vaginalis*, or *Eggerthella* sp. or components thereof (e.g., a target nucleic acid derived therefrom), including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; *The Biochemistry of the Nucleic Acids* 5-36, Adams et al., ed., 11$^{th}$ ed., 1992, Abraham et al., 2007, *BioTechniques* 43: 617-24), which include derivatives of purine or pyrimidine bases (e.g., N$^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

The term "polynucleotide," as used herein, denotes a nucleic acid chain. Throughout this application, nucleic acids are designated by the 5'-terminus to the 3'-terminus. Standard nucleic acids, e.g., DNA and RNA, are typically synthesized "5'-to-3'," i.e., by the addition of nucleotides to the 3'-terminus of a growing nucleic acid.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "nucleic-acid-based detection assay," as used herein, is an assay for the detection of a target sequence within a target nucleic acid and utilizing one more oligonucleotides that specifically hybridize to the target sequence.

In certain embodiments in accordance with the present invention, a nucleic-acid-based detection assay is an "amplification-based assay," i.e., an assay that utilizes one or more steps for amplifying a nucleic acid target sequence. Various amplification methods for use in detection assays are known in the art, several of which are summarized further herein. For the sake of clarity, an amplification-based assay may include one or more steps that do not amplify a target sequence, such as, for example, steps used in non-amplification-based assay methods (e.g., a hybridization assay or a cleavage-based assay).

In other embodiments, a nucleic-acid-based detection assay is a "non-amplification-based assay," i.e., an assay that does not rely on any step for amplifying a nucleic acid target sequence. For the sake of clarity, a nucleic-acid-based detection assay that includes a reaction for extension of a primer in the absence of any corresponding downstream amplification oligomer (e.g., extension of a primer by a reverse transcriptase to generate an RNA:DNA duplex followed by an RNase digestion of the RNA, resulting in a single-stranded cDNA complementary to an RNA target but without generating copies of the cDNA) is understood to be a non-amplification-based assay.

An exemplary non-amplification-based assay is a "cleavage-based assay," which is an assay that relies on the specific cleavage, by a flap endonuclease, of a linear duplex cleavage structure formed by the specific hybridization of overlapping oligonucleotides to a target nucleic acid. In these assays, a probe oligonucleotide containing a non-target-hybridizing flap region is cleaved in an overlap-dependent manner by the flap endonuclease to release a cleavage product that is then detected. The principles of cleavage-based assays are well-known in the art, and exemplary assays are described in, for example, Lyamichev et al. (*Nat. Biotechnol.* 17:292-296, 1999), Ryan et al. (*Mol. Diagn.* 4:135-144, 1999), Allawi et al. (*J. Clin. Microbiol.* 44:3443-3447, 2006), U.S. Pat. Nos. 5,846,717 & 6,706,471 to Brow et al., and U.S. Pat. No. 5,614,402 to Dahlberg et al. Cleavage-based assays include, e.g., the commercially available Invader® assays (Hologic, Inc., Madison, Wis.).

A "target nucleic acid," as used herein, is a nucleic acid comprising a target sequence to be detected. Target nucleic acids may be DNA or RNA as described herein, and may be either single-stranded or double-stranded. The target nucleic acid may include other sequences besides the target sequence.

By "isolated" it is meant that a sample containing a target nucleic acid is taken from its natural milieu, but the term does not connote any degree of purification.

The term "target sequence," as used herein, refers to the particular nucleotide sequence of a target nucleic acid that is to be detected. The "target sequence" includes the complexing sequences to which oligonucleotides (e.g., probe oligonucleotide, priming oligonucleotides and/or promoter oligonucleotides) complex during a detection process (e.g., an amplification-based detection assay such as, for example, TMA or PCR, or a non-amplification-based detection assay such as, for example, a cleavage-based assay). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *Lactobacillus*. It is understood that other reasons exist for configuring a target-hybridizing sequence to have less than 100% complementarity to a target nucleic acid.

The term "targets a sequence," as used herein in reference to a region of *Lactobacillus* sp., *G. vaginalis*, or *Eggerthella* sp. nucleic acid, refers to a process whereby an oligonucleotide hybridizes to the target sequence in a manner that allows for detection as described herein. In one embodiment, the oligonucleotide is complementary with the targeted *Lactobacillus* sp., *G. vaginalis*, or *Eggerthella* sp. nucleic acid sequence and contains no mismatches. In another embodiment, the oligonucleotide is complementary but contains 1, 2, 3, 4, or 5 mismatches with the targeted *Lactobacillus* sp., *G. vaginalis*, or *Eggerthella* sp. nucleic acid sequence. Preferably, the oligonucleotide that hybridizes to the target nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an oligonucleotide is designed to have a polynucleotide sequence that could target a sequence of the referenced *Lactobacillus* sp., *G. vaginalis*, or *Eggerthella* sp. target region. Such an oligonucleotide is not limited to targeting that sequence only, but is rather useful as a composition, in a kit or in a method for targeting a *Lactobacillus* sp., *G. vaginalis*, or *Eggerthella* sp. target nucleic acid. The oligonucleotide is designed to function as a component of an assay for detection of *Lactobacillus* sp., *G. vaginalis*, or *Eggerthella* sp. from a sample, and therefore is designed to target *Lactobacillus* sp., *G. vaginalis*, or *Eggerthella* sp. in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the oligonucleotide target-hybridizing sequence.

The term "fragment," as used herein in reference to an *Lactobacillus* sp., *G. vaginalis*, or *Eggerthella* sp. targeted nucleic acid, refers to a piece of contiguous nucleic acid. In certain embodiments, the fragment includes contiguous nucleotides from an *Lactobacillus* sp., *G. vaginalis*, or *Eggerthella* sp. 16S ribosomal RNA, wherein the number of 16S contiguous nucleotides in the fragment are less than that for the entire 16S.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a 16S ribosomal RNA, the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectable moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

"Amplification" refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. In some embodiments, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211). Preferred embodiments use an amplification method suitable for the amplification of RNA target nucleic acids, such as transcription-mediated amplification (TMA) or NASBA, but it will be apparent to persons of ordinary skill in the art that oligomers disclosed herein may be readily used as primers in other amplification methods.

"Transcription-associated amplification," also referred to herein as "transcription-mediated amplification" (TMA), refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting HSV target sequences as described herein. Variations of transcription-associated amplification are well-known in the art as previously disclosed in detail (e.g., U.S. Pat. Nos. 4,868,105; 5,124,246; 5,130,238; 5,399,491; 5,437,990; 5,554,516; and 7,374,885; and PCT Pub. Nos. WO 88/01302, WO 88/10315, and WO 95/03430). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon," which is used interchangeably with "amplification product," refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

"Probe," "detection probe," "detection oligonucleotide," and "detection probe oligomer" are used interchangeably herein to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained.

The term "TaqMan® probe" refers to detection oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan probe to separate the fluorophore from the quencher, thereby allowing an unquenched signal to be emitted from the fluorophore as an indicator of amplification.

As used herein, a "label" refers to a moiety or compound joined directly or indirectly to a probe that is detected or leads to a detectable signal. Direct labelling can occur through bonds or interactions that link the label to the probe, including covalent bonds or non-covalent interactions, e.g., hydrogen bonds, hydrophobic and ionic interactions, or formation of chelates or coordination complexes. Indirect labelling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., *Molecular Cloning, A Laboratory Manual*, 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

"Capture probe," "capture oligonucleotide," "target capture oligonucleotide," and "capture probe oligomer" are used interchangeably herein to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support (see, e.g., PCT Pub No. WO 2008/016988). The immobilized probe binding region can be a nucleic acid sequence, referred to as a tail. Tails include a substantially homopolymeric tail of about 10 to 40 nucleotides (e.g., $A_{10}$ to $A_{40}$), or of about 14 to 33 nt (e.g., $T_3A_{14}$ to $T_3A_{30}$), that bind to a complementary immobilized sequence attached to the support particle or support matrix. Thus, a non-limiting example of preferred nucleic acid tails can in some embodiments include $T_{0-4}A_{10-40}$ sequences. Another example of a capture oligomer comprises two regions, a target hybridizing sequence and a binding pair member that is not a nucleic acid sequence.

As used herein, an "immobilized oligonucleotide," "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size±5%), to which an immobilized probe is joined directly (via covalent linkage, chelation, or ionic interaction), or indirectly (via one or more linkers), where the linkage or interaction between the probe and support is stable during hybridization conditions.

BRIEF DESCRIPTION OF THE DRAWINGS

FIG. 1A illustrates a reference sequence (SEQ ID NO:1) for *Lactobacillus* 16S ribosomal RNA gene (*Lactobacillus crispatus* strain ATCC 33820 16S ribosomal RNA gene, partial sequence, found at GenBank under accession number NR_041800.1 GI:343201103). FIG. 1B illustrates a reference sequence (SEQ ID NO:88) for *Lactobacillus jensenii* 16S ribosomal RNA gene, partial sequence, GenBank accession number NR_025087.1 GI:219857499.

FIG. 2 illustrates a reference sequence (SEQ ID NO:2) for *Lactobacillus* 16S ribosomal RNA gene (*Lactobacillus gasseri* partial 16S rRNA gene, type strain CIP 102991Tstrain, found at GenBank under accession number HE573914.1 GI:341599788).

FIG. 3 illustrates a reference sequence (SEQ ID NO:3) for *Gardnerella vaginalis* 16S ribosomal RNA gene (*Gardnerella vaginalis* strain 594 16S ribosomal RNA gene, complete sequence, found at GenBank under accession number NR_044694.2 GI:545589071).

FIG. 4 illustrates a reference sequence (SEQ ID NO:4) for *Eggerthella* 16S ribosomal RNA gene (Uncultured *Eggerthella* sp. clone 123-f2 68 16S ribosomal RNA gene, partial sequence, found at GenBank under accession number AY738656.1 GI:52222145).

DESCRIPTION

The present invention is generally directed to methods and compositions for determining the presence or absence of select bacterial organisms in a sample. In some embodiments, the present invention provides methods and compositions for diagnosing Bacterial Vaginosis (BV) in a subject. In other, non-mutually exclusive embodiments, the present invention provides methods for the detection of any one or more of *Lactobacillus* sp., *G. vaginalis*, and *Eggerthella* sp. in a sample, where the method includes performing amplification-based detection of a 16S rRNA target nucleic from one or more of *Lactobacillus* sp., *G. vaginalis*, and *Eggerthella* sp. The present invention further provides compositions (including reaction mixtures) and kits comprising a combination of oligomers for detecting any one or more of *Lactobacillus* sp., *G. vaginalis*, and *Eggerthella* sp. in a sample. The oligomer combination generally includes at least two amplification oligomers for detecting one or more of *Lactobacillus* sp., *G. vaginalis*, and *Eggerthella* sp. in a sample, and may further include one or more additional oligomers as described herein for performing amplification-based detection of *Lactobacillus* sp., *G. vaginalis*, and/or *Eggerthella* sp. such as, e.g., a capture probe and/or a detection probe.

The methods for diagnosing BV generally include detecting the presence or absence of one or more of *Lactobacillus* sp., *G. vaginalis*, and *Eggerthella* sp. in a sample from a subject suspected of having BV. In particular, an assay is performed for the specific detection in the sample of each of *Lactobacillus* sp., *G. vaginalis*, and *Eggerthella* sp., or the specific detection in the sample of each of *Lactobacillus* sp. and *G. vaginalis*. Based on the results from the detection assay, a status of either positive or negative is assigned for each of *Lactobacillus* sp., *G. vaginalis*, and *Eggerthella* sp., or each of *Lactobacillus* sp. and *G. vaginalis*, and the presence or absence of BV in the subject is determined based on a combination of the assigned *Lactobacillus* sp. status, *G. vaginalis* status, and *Eggerthella* sp. status, or based on a combination of the assigned *Lactobacillus* sp. status and *G. vaginalis* status.

In particular, where a status of either positive or negative is assigned for each of *Lactobacillus* sp., *G. vaginalis*, and *Eggerthella* sp. a negative status for both *G. vaginalis* and *Eggerthella* sp. indicates the absence of BV in the subject, and a positive status for both *G. vaginalis* and *Eggerthella* sp. indicates the presence of BV in the subject. Further, if the status of *Lactobacillus* sp. is positive, then a negative status for at least one of *G. vaginalis* and *Eggerthella* indicates the absence of BV in the subject, and if the status of *Lactobacillus* sp. is negative, then a positive status for at least one of *G. vaginalis* and *Eggerthella* indicates the presence of BV in the subject. Table 1 below shows a BV indication matrix based on the combined status for *Lactobacillus*, *G. vaginalis*, and *Eggerthella*.

TABLE 1

Bacterial Vaginosis Indication Matrix Based on *Lactobacillus*, *G. vaginalis*, and *Eggerthella*

| *Lactobacillus* status | *G. vaginalis* status | *Eggerthella* status | BV |
|---|---|---|---|
| + | + | + | Yes |
| + | + | − | No |
| + | − | + | No |
| − | − | − | No |
| − | + | − | Yes |
| − | − | + | Yes |
| − | + | + | Yes |
| + | − | − | No |

Alternatively, where a status of either positive or negative is assigned for each of *Lactobacillus* sp. and *G. vaginalis*, a negative status for *G. vaginalis* indicates the absence of BV in the subject. Further, if the status of *G. vaginalis* is positive, then a positive status for *Lactobacillus* sp. indicates the absence of BV in the subject and a negative status for *Lactobacillus* sp. indicates the presence of BV in the subject. It is noted, though, that the presence of a high copy number (e.g., ≥1.4e10 copies/mL) of *G. vaginalis* in a sample is a positive indicator of BV in the subject. Table 2 below shows a BV indication matrix based on the combined status for *Lactobacillus* and *G. vaginalis*.

TABLE 2

Bacterial Vaginosis Indication Matrix Based on *Lactobacillus* and *G. vaginalis*

| *Lactobacillus* status | *G. vaginalis* status | BV |
|---|---|---|
| + | + | No |
| + | − | No |
| − | + | Yes |
| − | − | No |

While *Lactobacillus* sp., *G. vaginalis*, and/or *Eggerthella* sp. may be detected using any suitable method, it is presently preferred that these bacteria are detected using a nucleic-acid-based detection assay. Nucleic-acid-based detection assays in accordance with the present invention generally utilize oligonucleotides that specifically hybridize to a target nucleic acid of *Lactobacillus* sp., *G. vaginalis*, or *Eggerthella* sp. with minimal cross-reactivity to other nucleic acids suspected of being in a sample. Accordingly, oligonucleotides for nucleic-acid-based detection of the select species of *Lactobacillus* sp., *G. vaginalis*, or *Eggerthella* sp.

will have minimal cross-reactivity to species within other bacterial genera, including, for example, *Trichomonas* sp.; *Trichomonas vaginalis*; *Candida* sp.; Bacterium from the order Clostridiales; *Clostridium*-like sp.; *Atopobium* sp.; *Atopobium vaginae*; Enterobacteria; *Peptostreptococcus micros*; *Aerococcus christensenii*; *Leptotrichia amnionii*; *Peptoniphilus* sp.; *Dialister* sp.; *Mycoplasma hominis*; *Sneathia sanguinegens*; *Anaerococcus tetradius*; *Mobiluncus* sp.; *Mobiluncus hominis*; *Megasphaera* sp.; *Prevotella* sp.; *Leptotrichia sanguinegens*; and *Finegoldia magna*. In one aspect, a nucleic-acid-based detection assay in accordance with the present invention further includes components for detecting one of more of these organisms, or other bacterial genera associated with BV.

In particular embodiments, a nucleic-acid-based detection assay targets the 16S rRNA of *Lactobacillus* sp., *G. vaginalis*, and/or *Eggerthella* sp., or a gene encoding the 16S rRNA. Particularly suitable target regions of the 16S rRNA or the encoding gene are (i) a *Lactobacillus* sp. 16S rRNA region corresponding to a region of SEQ ID NO:1 from about nucleotide position 91 to about nucleotide position 265; (ii) a *Lactobacillus* sp. 16S rRNA region corresponding to a region of SEQ ID NO:2 from about nucleotide position 90 to about nucleotide position 263; (iii) a *G. vaginalis* 16S rRNA region corresponding to a region of SEQ ID NO:3 from about nucleotide position 964 to about nucleotide position 1036; and (iv) an *Eggerthella* sp. 16S rRNA region corresponding to a region of SEQ ID NO:4 from about nucleotide position 165 to about nucleotide position 259. In specific variations of a nucleic-acid-based detection assay targeting a 16S rRNA region as above, (a) a *Lactobacillus*-specific oligonucleotide includes a target-hybridizing region comprising a sequence substantially corresponding to the sequence shown in SEQ ID NO:6, a sequence substantially corresponding to the sequence shown in residues 28-45 of SEQ ID NO:7, a sequence substantially corresponding to the sequence shown in residues 28-45 of SEQ ID NO:8, a sequence substantially corresponding to the sequence shown in SEQ ID NO:9, or a sequence substantially corresponding to the sequence shown in residues 6-21 of SEQ ID NO:10; (b) a *G. vaginalis*-specific oligonucleotide includes a target-hybridizing region comprising a sequence substantially corresponding to the sequence shown in SEQ ID NO:12, a sequence substantially corresponding to the sequence shown in residues 28-45 of SEQ ID NO:13, or a sequence substantially corresponding to the sequence shown in residues 1-19 of SEQ ID NO:14; and/or (c) an *Eggerthella*-specific oligonucleotide includes a target-hybridizing region comprising a sequence substantially corresponding to the sequence shown in SEQ ID NO:16, a sequence substantially corresponding to the sequence shown in residues 28-51 of SEQ ID NO:17, or a sequence substantially corresponding to the sequence shown SEQ ID NO:18. In some such embodiments, (a) a *Lactobacillus*-specific oligonucleotide includes a target-hybridizing region comprising or consisting of the sequence shown in SEQ ID NO:6, the sequence shown in residues 28-45 of SEQ ID NO:7, the sequence shown in residues 28-45 of SEQ ID NO:8, or the sequence shown in SEQ ID NO:9; (b) a *G. vaginalis*-specific oligonucleotide includes a target-hybridizing region comprising or consisting of the sequence shown in SEQ ID NO:12, the sequence shown in residues 28-45 of SEQ ID NO:13, or the sequence shown in residues 1-19 of SEQ ID NO:14; and/or (c) an *Eggerthella*-specific oligonucleotide includes a target-hybridizing region comprising or consisting of the sequence shown in SEQ ID NO:16, the sequence shown in residues 28-51 of SEQ ID NO:17, or the sequence shown SEQ ID NO:18. In certain embodiments, a nucleic-acid-based detection assay utilizes at least two or three *Lactobacillus*-specific oligonucleotides, at least two or three *G. vaginalis*-specific oligonucleotides, and/or at least two or three *Eggerthella*-specific oligonucleotides, which may be oligonucleotides selected from those specified above.

In some embodiments of a method comprising the use of a nucleic-acid-base detection assay, an amplification-based assay is used to detect *Lactobacillus* sp., *G. vaginalis*, and/or *Eggerthella* sp. Such variations generally include amplifying a target sequence within a bacterial target nucleic acid utilizing an in vitro nucleic acid amplification reaction and detecting the amplified product by, for example, specifically hybridizing the amplified product with a nucleic acid detection probe that provides a signal to indicate the presence of a bacterial target in the sample. The amplification step includes contacting the sample with two or more amplification oligomers specific for a target sequence in a target nucleic acid (e.g., a target sequence in a 16S rRNA) to produce an amplified product if the target nucleic acid is present in the sample. Amplification synthesizes additional copies of the target sequence or its complement such as, e.g., by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected amplification oligomers. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art (see, e.g., discussion of amplification methods in Definitions section, supra) and are readily used in accordance with the methods of the present invention.

For example, some amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configure to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

In certain embodiments comprising an amplification-based detection assay, a combination of at least two amplification oligomers is utilized for the detection of a *Lactobacillus* sp. 16S rRNA or a gene encoding a *Lactobacillus* sp. 16S rRNA. The oligomer combination may include first and second amplification oligomers for amplifying a *Lactobacillus* sp. nucleic acid target region corresponding to a region of SEQ ID NO:1 from about nucleotide position 91 to about nucleotide position 265, and/or a *Lactobacillus* sp. nucleic acid target region corresponding to a region of SEQ ID NO:2 from about nucleotide position 90 to about nucleotide position 263. For example, in some embodiments, the first amplification oligomer includes a target-hybridizing sequence substantially corresponding to the nucleotide sequence of residues 28-45 of SEQ ID NO:7 or residues 28-45 of SEQ ID NO:8, and/or the second amplification oligomer includes a target-hybridizing sequence substantially corresponding to the nucleotide sequence of SEQ ID NO:6. In more particular variations, the first amplification oligomer includes a target-hybridizing sequence comprising or consisting of the nucleotide sequence of residues 28-45 of SEQ ID NO:7 or residues 28-45 of SEQ ID NO:8, and/or the second amplification oligomer includes a target-hybridizing sequence comprising or consisting of the nucleotide sequence of SEQ ID NO:6. In some embodiments, where the first amplification oligomer includes a target-hybridizing sequence substantially corresponding to the nucleotide sequence of residues 28-45 of SEQ ID NO:7, the amplification detection assay further utilizes a third amplification oligomer that includes a target-hybridizing sequence substantially corresponding to the nucleotide sequence of residues 28-45 of SEQ ID NO:8; in some such variations, the third amplification oligomer includes a target-hybridizing sequence comprising or consisting of the nucleotide sequence of residues 28-45 of SEQ ID NO:8. In some embodiments as above, at least one amplification is a promoter primer or promoter provide further comprising a promoter sequence located 5' to the respective target-hybridizing sequence (e.g., a T7 promoter sequences such as, for example, the nucleotide sequence of residues 1-27 of SEQ ID NO:7); in some such embodiments, the first amplification oligomer is a promoter primer or promoter provider, and/or, if present, the third amplification oligomer is a promoter primer or promoter provider. In more specific variations, the first amplification oligomer consists of the nucleotide sequence of SEQ ID NO:7, the second amplification oligomer consists of the nucleotide sequence of SEQ ID NO:6, and/or, if present, the third amplification oligomer consists of the nucleotide sequence of SEQ ID NO:8.

In certain embodiments comprising an amplification-based detection assay, a combination of at least two amplification oligomers is utilized for the detection of a *G. vaginalis* 16S rRNA or a gene encoding a *G. vaginalis* 16S rRNA. The oligomer combination may include first and second amplification oligomers for amplifying a *G. vaginalis* nucleic acid target region corresponding to a region of SEQ ID NO:3 from about nucleotide position 964 to about nucleotide position 1036. For example, in some embodiments, the first amplification oligomer includes a target-hybridizing sequence substantially corresponding to the nucleotide sequence of residues 28-45 of SEQ ID NO:13 and/or the second amplification oligomer includes a target-hybridizing sequence substantially corresponding to the nucleotide sequence of SEQ ID NO:12. In more particular variations, the first amplification oligomer includes a target-hybridizing sequence comprising or consisting of the nucleotide sequence of residues 28-45 of SEQ ID NO:13 and/or the second amplification oligomer includes a target-hybridizing sequence comprising or consisting of the nucleotide sequence of SEQ ID NO:12. hi some embodiments as above, at least one amplification is a promoter primer or promoter provide further comprising a promoter sequence located 5' to the respective target-hybridizing sequence (e.g., a T7 promoter sequences such as, for example, the nucleotide sequence of residues 1-27 of SEQ ID NO:7); in some such embodiments, the first amplification oligomer is a promoter primer or promoter provider. In more specific variations, the first amplification oligomer consists of the nucleotide sequence of SEQ ID NO:13 and/or the second amplification oligomer consists of the nucleotide sequence of SEQ ID NO:12.

In certain embodiments comprising an amplification-based detection assay, a combination of at least two amplification oligomers is utilized for the detection of an *Eggerthella* sp. 16S rRNA or a gene encoding an *Eggerthella* sp. 16S rRNA. The oligomer combination may include first and second amplification oligomers for amplifying an *Eggerthella* sp. nucleic acid target region corresponding to a region of SEQ ID NO:4 from about nucleotide position 165 to about nucleotide position 259. For example, in some embodiments, the first amplification oligomer includes a target-hybridizing sequence substantially corresponding to the nucleotide sequence of residues 28-51 of SEQ ID NO:17 and/or the second amplification oligomer includes a target-hybridizing sequence substantially corresponding to the nucleotide sequence of SEQ ID NO:16. In more particular variations, the first amplification oligomer includes a target-hybridizing sequence comprising or consisting of the nucleotide sequence of residues 28-51 of SEQ ID NO:17 and/or the second amplification oligomer includes a target-hybridizing sequence comprising or consisting of the nucleotide sequence of SEQ ID NO:16. In some embodiments as above, at least one amplification is a promoter primer or promoter provide further comprising a promoter sequence located 5' to the respective target-hybridizing sequence (e.g., a T7 promoter sequences such as, for example, the nucleotide sequence of residues 1-27 of SEQ ID NO:7); in some such embodiments, the first amplification oligomer is a promoter primer or promoter provider. In more specific variations, the first amplification oligomer consists of the nucleotide sequence of SEQ ID NO:17 and/or the second amplification oligomer consists of the nucleotide sequence of SEQ ID NO:16.

Detection of the amplified products may be accomplished by a variety of methods to detect a signal specifically associated with the amplified target sequence. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. For example, if the target nucleic acid is the 16S rRNA of *Lactobacillus* sp., *G. vaginalis*, and/or *Eggerthella* sp., the amplified product will contain a target sequence in or complementary to a sequence in the 16S rRNA, and a probe will bind directly or indirectly to a sequence contained in the amplified product to indicate the presence of the 16S rRNA of *Lactobacillus* sp., *G. vaginalis*, and/or *Eggerthella* sp. in the tested sample.

Detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified sequences may be unlabeled and detected indirectly (e.g., by binding of another binding partner to a moiety on the probe) or may be labeled with a variety of detectable labels. In some embodiments of the method for diagnosing BV, such as in certain embodiments using transcription-mediated amplification (TMA), the detection probe is a linear chemiluminescently labeled probe such as, e.g., a linear acridinium ester (AE) labeled probe.

The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174, each incorporated by reference herein).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

In certain embodiments comprising an amplification-based detection assay targeting a *Lactobacillus* sp., *G. vaginalis*, and/or *Eggerthella* sp. 16S rRNA or a gene encoding a *Lactobacillus* sp., *G. vaginalis*, and/or *Eggerthella* sp. 16S rRNA, the method utilizes one or more detection probes that specifically hybridizes to a *Lactobacillus* sp., *G. vaginalis*, and/or *Eggerthella* sp. 16S rRNA amplification product. In particular variations, a *Lactobacillus*-specific detection probe specifically hybridizes to a nucleic acid target region corresponding to a region of SEQ ID NO:1 from about nucleotide position 91 to about nucleotide position 265, and/or a *Lactobacillus* sp. nucleic acid target region corresponding to a region of SEQ ID NO:2 from about nucleotide position 90 to about nucleotide position 263; a *G. vaginalis*-specific detection probe specifically hybridizes to a nucleic acid target region corresponding to a region of SEQ ID NO:3 from about nucleotide position 964 to about nucleotide position 1036; and/or an *Eggerthella*-specific probe specifically hybridizes to a nucleic acid target region corresponding to a region of SEQ ID NO:4 from about nucleotide position 165 to about nucleotide position 259. For example, in some variations, a probe for detection of a *Lactobacillus* sp. amplification product includes a target-hybridizing sequence substantially corresponding to the sequence of SEQ ID NO:9 or a sequence substantially corresponding to the sequence of residues 6-21 of SEQ ID NO:10 (e.g., a probe that comprises the target-hybridizing sequence of SEQ ID NO:9 or residues 6-21 of SEQ ID NO:10). In some variations, a probe for detection of a *G.*

*vaginalis* amplification product includes a target-hybridizing sequence substantially corresponding to the sequence of residues 1-19 of SEQ ID NO:14 (e.g., a probe that comprises the target-hybridizing sequence of residues 1-19 of SEQ ID NO:14). In some variations, a probe for detection of an *Eggerthella* sp. amplification product includes a target-hybridizing sequence substantially corresponding to the sequence of SEQ ID NO:18 (e.g., a probe that comprises the target-hybridizing sequence of SEQ ID NO:18). In certain embodiments, a probe for detection of a *Lactobacillus* sp. amplification product comprises or consists of the sequence of SEQ ID NO:9 or SEQ ID NO:10; a probe for detection of a *G. vaginalis* amplification product comprises or consists of the sequence of SEQ ID NO:14; and/or a probe for detection of an *Eggerthella* sp. amplification product comprises or consists of the sequence of SEQ ID NO:18.

In some embodiments of a method comprising the use of a nucleic-acid-base detection assay, a non-amplification-based assay is used to detect *Lactobacillus* sp., *G. vaginalis*, and/or *Eggerthella* sp. In some such embodiments, the non-amplification-based assay is a hybridization assay comprising the hybridization of a specific detection probe to a target nucleic acid. Methods for conducting polynucleotide hybridization assays have been well developed in the art. Hybridization assay procedures and conditions will vary depending on the application and are selected in accordance with the general binding methods known, including those referred to in, e.g., Maniatis et al., *Molecular Cloning: A Laboratory Manual* (3rd ed. Cold Spring Harbor, N.Y., 2002), and Berger and Kimmel, *Methods in Enzymology, Vol.* 152, *Guide to Molecular Cloning Techniques* (Academic Press, Inc., San Diego, Calif., 1987). Generally, the probe and sample are mixed under conditions that will permit specific nucleic acid hybridization, and specific hybridization of the probe to its respective target is then detected. Nucleic acid hybridization is adaptable to a variety of assay formats. One suitable format is the sandwich assay format, which is particularly adaptable to hybridization under non-denaturing conditions. A primary component of a sandwich-type assay is a solid support, which has adsorbed to it or covalently coupled to it immobilized nucleic acid probe that is unlabeled and complementary to one portion of the DNA sequence. Target nucleic acid is hybridized to the immobilized probe, and a second, labeled detection probe—which is complementary to a second and different region of the same DNA strand to which the immobilized, unlabeled nucleic acid probe is hybridized—is hybridized to the [target nucleic acid]:[immobilized probe] duplex to detect the target nucleic acid. Another exemplary format utilizes electro-chemical detection of target nucleic acids hybridized to unlabeled detection probes immobilized on a suitable electrode surface as a signal transducer. See, e.g., Drummond et al., *Nat. Biotechnol.* 21:1192, 2003; Gooding, *Electroanalysis* 14:1149, 2002; Wang, *Anal. Chim. Acta* 469:63, 2002; Cagnin et al., *Sensors* 9:3122, 2009; Katz and Willner, *Electroanalysis* 15:913, 2003; Daniels and Pourmand, *Electroanalysis* 19:1239, 2007.

In certain embodiments comprising a hybridization assay, a detection probe is utilized for the detection of a *Lactobacillus* sp., *G. vaginalis*, and/or *Eggerthella* sp. 16S rRNA or a gene encoding a *Lactobacillus* sp., *G. vaginalis*, and/or *Eggerthella* sp. 16S rRNA. In such embodiments, a probe for detecting a *Lactobacillus* sp. 16S rRNA or gene encoding a *Lactobacillus* sp. 16S rRNA specifically hybridizes to a nucleic acid target region corresponding to a region of SEQ ID NO:1 from about nucleotide position 91 to about nucleotide position 265, and/or a *Lactobacillus* sp. nucleic acid target region corresponding to a region of SEQ ID NO:2 from about nucleotide position 90 to about nucleotide position 263; a probe for detecting a *G. vaginalis* 16S rRNA or gene encoding a *G. vaginalis* 16S rRNA specifically hybridizes to a nucleic acid target region corresponding to a region of SEQ ID NO:3 from about nucleotide position 964 to about nucleotide position 1036; and/or a probe for detecting an *Eggerthella* sp. 16S rRNA or gene encoding an *Eggerthella* sp. 16S rRNA specifically hybridizes to a nucleic acid target region corresponding to a region of SEQ ID NO:4 from about nucleotide position 165 to about nucleotide position 259. For example, in some variations, a probe for detection of a *Lactobacillus* sp. 16S rRNA or gene encoding a *Lactobacillus* sp. 16S rRNA includes a target-hybridizing sequence substantially corresponding to the sequence of SEQ ID NO:9 or a sequence substantially corresponding to the sequence of residues 6-21 of SEQ ID NO:10 (e.g., a probe that comprises the target-hybridizing sequence of SEQ ID NO:9 or residues 6-21 of SEQ ID NO:10). In some variations, a probe for detection of a *G. vaginalis* 16S rRNA or gene encoding a *G. vaginalis* 16S rRNA includes a target-hybridizing sequence substantially corresponding to the sequence of residues 1-19 of SEQ ID NO:14 (e.g., a probe that comprises the target-hybridizing sequence of residues 1-19 of SEQ ID NO:14). In some variations, a probe for detection of an *Eggerthella* sp. 16S rRNA or gene encoding an *Eggerthella* sp. 16S rRNA includes a target-hybridizing sequence substantially corresponding to the sequence of SEQ ID NO:18 (e.g., a probe that comprises the target-hybridizing sequence of SEQ ID NO:18). In certain embodiments, a probe for detection of a *Lactobacillus* sp. 16S rRNA or gene encoding a *Lactobacillus* sp. 16S rRNA comprises or consists of the sequence of SEQ ID NO:9 or SEQ ID NO:10; a probe for detection of a *G. vaginalis* 16S rRNA or gene encoding a *G. vaginalis* sp. 16S rRNA comprises or consists of the sequence of SEQ ID NO:14; and/or a probe for detection of an *Eggerthella* sp. 16S rRNA or gene encoding an *Eggerthella* sp. 16S rRNA comprises or consists of the sequence of SEQ ID NO:18.

In some embodiments, a non-amplification-based assay for detection of *Lactobacillus* sp., *G. vaginalis*, and/or *Eggerthella* sp. is a cleavage-based assay, in which a probe oligonucleotide containing a non-target-hybridizing flap region is cleaved in an overlap-dependent manner by a flap endonuclease to release a cleavage product that is then detected. Exemplary cleavage-based assay reagents are described in, e.g., Lyamichev et al. (*Nat. Biotechnol.* 17:292-296, 1999), Ryan et al. (*Mol. Diagn.* 4:135-144, 1999), and Allawi et al. (*J. Clin. Microbiol.* 44:3443-3447, 2006). Appropriate conditions for flap endonuclease reactions are either known or can be readily determined using methods known in the art (see, e.g., Kaiser et al., *J. Biol. Chem.* 274:2138-721394, 1999). Exemplary flap endonucleases that may be used in the method include *Thermus aquaticus* DNA polymerase I, *Thermus thermophilus* DNA polymerase I, mammalian FEN-1, *Archaeoglobus fulgidus* FEN-1, *Methanococcus jannaschii* FEN-1, *Pyrococcus furiosus* FEN-1, *Methanobacterium thermoautotrophicum* FEN-1, *Thermus thermophilus* FEN-1, CLEAVASE® (Hologic, Inc., Madison, Wis.), *S. cerevisiae* RTH1, *S. cerevisiae* RAD27, *Schizosaccharomyces pombe* rad2, bacteriophage T5 5'-3' exonuclease, *Pyrococcus horikoshii* FEN-1, human endonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of flap endonucleases can be found in, for example, Lyamichev et al., *Science* 260:778-783, 1993; Eis et al., *Nat. Biotechnol.* 19:673-676, 2001; Shen et al., *Trends in Bio. Sci.* 23:171-173, 1998; Kaiser et al., *J. Biol. Chem.* 274:21387-21394, 1999; Ma et al., *J. Biol. Chem.* 275:24693-24700, 2000; Allawi et al., *J. Mol. Biol.* 328: 537-554, 2003; Sharma et al., *J. Biol. Chem.* 278:23487-23496, 2003; and Feng et al., *Nat. Struct. Mol. Biol.* 11:450-456, 2004.

In certain variations, a cleavage-based assay detects an RNA target nucleic acid of *Lactobacillus* sp., *G. vaginalis*, and/or *Eggerthella* sp., and the cleavage-based assay utilizes a flap endonuclease that is capable of cleaving and RNA:DNA linear duplex structure. In some alternative embodiments, a cleavage-based assay detects a DNA target nucleic acid of *Lactobacillus* sp., *G. vaginalis*, and/or *Eggerthella* sp., and the cleavage-based assay utilizes a flap endonuclease that is capable of cleaving and DNA:DNA linear duplex structure. Exemplary flap endonucleases capable of cleaving RNA:DNA duplexes include polymerase-deficient 5' nucleases of the genus *Thermus* as well as certain CLEAVASE® enzymes (Hologic, Inc., Madison, Wis.) such as, for example, CLEAVASE® BN (BstX-NotI deletion of Taq polymerase, see U.S. Pat. No. 5,614,402), CLEAVASE® II ("AG" mutant of full length Taq polymerase, see U.S. Pat. No. 5,614,402), CLEAVASE® VII (synthesis-deficient mutation of full length *Thermus thermophilus* polymerase), CLEAVASE® IX (polymerase deficient mutant of the Tth DNA polymerase), and CLEAVASE® XII (polymerase deficient chimeric polymerase constructed from fragments of taq DNA polymerase and Tth DNA polymerase). Exemplary flap endonucleases capable of cleaving DNA:DNA duplexes include the flap endonucleases indicated above, as well as CLEAVASE® 2.0 (*Archaeoglobus fulgidus* FEN-1), CLEAVASE® 2.1 (*Archaeoglobus fulgidus* FEN-1 with 6 histidines on the C-terminus), CLEAVASE® 3.0 (*Archaeoglobus veneficus* FEN-1), and CLEAVASE® 3.1 (*Archaeoglobus veneficus* FEN-1 with 6 histidines on the C-terminus).

In some embodiments, a cleavage-based assay detects an RNA target nucleic acid of *Lactobacillus* sp., *G. vaginalis*, and/or *Eggerthella* sp., and the assay includes a step for synthesizing a DNA complement of an RNA target region, which cDNA strand is then hybridized to overlapping first and second probe oligonucleotides to form a linear duplex cleavage structure for cleavage by the flap endonuclease. Reaction conditions for synthesizing cDNA from an RNA template, using an RNA-dependent DNA polymerase (reverse transcriptase), are well-known in the art.

In certain embodiments utilizing a nucleic-acid-based detection assay, the method further includes purifying the *Lactobacillus* sp., *G. vaginalis*, and/or *Eggerthella* sp. target nucleic acid from other components in the sample. Such purification may include may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Lactobacillus* sp., *G. vaginalis*, and/or *Eggerthella* sp. nucleic acid and other sample components.

In some embodiments, a target nucleic acid (e.g., a 16S rRNA target nucleic or a gene encoding the 16S rRNA) of *Lactobacillus* sp., *G. vaginalis*, and/or *Eggerthella* sp. is separated from other sample components by hybridizing the target nucleic acid to a capture probe oligomer. The capture probe oligomer comprises a target-hybridizing sequence configured to specifically or non-specifically hybridize to a target nucleic acid so as to form a [target nucleic acid]:[capture probe] complex that is separated from other sample components. Capture probes comprising target-hybridizing sequences suitable for non-specific capture of target nucleic acids are described in, e.g., International PCT Publication WO 2008/016988, incorporated by reference herein. In some specific variations comprising target-hybridizing sequence(s) configured to specifically hybridize to a *Lactobacillus* sp., *G. vaginalis*, and/or *Eggerthella* sp. 16S rRNA target nucleic acid, a *Lactobacillus*-specific capture probe comprises a target-hybridizing sequence substantially corresponding to the nucleotide sequence of residues 1-12 of SEQ ID NO:5 (e.g., a capture probe the comprises the target-hybridizing sequence of residues 1-12 of SEQ ID NO:5); a *G. vaginalis*-specific capture probe comprises a target-hybridizing sequence substantially corresponding to the nucleotide sequence of residues 1-17 of SEQ ID NO:11 (e.g., a capture probe the comprises the target-hybridizing sequence of residues 1-17 of SEQ ID NO:11); and/or an *Eggerthella*-specific capture probe comprises a target-hybridizing sequence substantially corresponding to the nucleotide sequence of residues 1-21 of SEQ ID NO:15 (e.g., a capture probe the comprises the target-hybridizing sequence of residues 1-21 of SEQ ID NO:15). In a preferred variation, the capture probe binds the [target nucleic acid]:[capture probe] complex to an immobilized probe to form a [target nucleic acid]:[capture probe]:[immobilized probe] complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds attaches the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to target nucleic acid but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. In some such embodiments comprising target-hybridizing sequence(s) configured to specifically hybridize to a *Lactobacillus* sp., *G. vaginalis*, and/or *Eggerthella* sp. 16S rRNA target nucleic acid, a *Lactobacillus*-specific capture probe comprises or consists of a the nucleotide sequence of SEQ ID NO:5; a *G. vaginalis*-specific capture probe comprises or consists of the nucleotide sequence of SEQ ID NO:11; and/or an *Eggerthella*-specific capture probe comprises or consists of the nucleotide sequence of SEQ ID NO:15.

Target capture typically occurs in a solution phase mixture that contains one or more capture probe oligomers that hybridize to the target nucleic acid under hybridizing conditions, usually at a temperature higher than the $T_m$ of the [tail sequence]:[immobilized probe sequence] duplex. For embodiments comprising a capture probe tail, the [target nucleic acid]:[capture probe] complex is captured by adjusting the hybridization conditions so that the capture probe tail hybridizes to the immobilized probe, and the entire complex on the solid support is then separated from other sample components. The support with the attached [immobilized probe]:[capture probe]:[target nucleic acid] may be washed one or more times to further remove other sample components. Preferred embodiments use a particulate solid support, such as paramagnetic beads, so that particles with the attached [target nucleic acid]:[capture probe]:[immobilized probe] complex may be suspended in a washing solution and retrieved from the washing solution, preferably by using magnetic attraction. In embodiments of the method comprising the use of an amplification-based detection assay, to limit the number of handling steps, a target nucleic acid may be amplified by simply mixing the target nucleic acid in the complex on the support with amplification oligomers and proceeding with amplification steps.

In some embodiments of a method for diagnosing BV, where detection of *Lactobacillus* sp., *G. vaginalis*, and/or *Eggerthella* sp. indicate BV in a subject, the method further includes treating BV in the subject. Treatment regimes for BV are generally known in the art and include, for example, administration of antibiotic drugs such as metronidazole (e.g., FLAGYL, METROGEL-VAGINAL), clindamycin (e.g., CLEOCIN, CLINDESSE), and tinidazole (e.g., TINDAMAX). In certain variations, the subject has not been previously diagnosed with BV. In other embodiments, the subject has been previously diagnosed with BV and is undergoing treatment for BV at the time a diagnostic method of the present disclosure is performed. Such variations are particularly useful for monitoring treatment of BV in a subject. For example, if the method indicates that BV is still present in the subject, then the subject may continue treatment. In some embodiments, the same treatment regime (i.e., the same treatment that the subject is undergoing at the time the present diagnostic method is performed) is re-administered to the subject. Alternatively, the continued presence of BV in the subject undergoing treatment may indicate that a change in the ongoing treatment is needed, and a different treatment regime (e.g., a different medication, or an increased dosage and/or frequency of a drug) is administered to the subject.

In accordance with the present invention, detecting the presence or absence of *Lactobacillus* sp., *G. vaginalis*, and/or *Eggerthella* sp. may be performed separately for each target (e.g., in separate reaction vessels, sequentially or in parallel), or performed together as a multiplex reaction system. Accordingly, in some embodiments, a method as described herein (e.g., a method for diagnosing BV) utilizes a multiplex reaction, where the reaction mix contains reagents for assaying multiple (e.g., at least two, three, four, or more) different target sequences in parallel. In these cases, a reaction mix may contain multiple different target-specific oligonucleotides for performing the detection assay. For example, in a method utilizing an amplification-based detection assay, a multiplex reaction may contain multiple sets (e.g., multiple pairs) of amplification oligomers (for example, multiple pairs of PCR primers or multiple pairs of TMA amplification oligomers (e.g., for TMA, multiple pairs of promoter primer and non-promoter primer, or multiple pairs of promoter provider and non-promoter primer)). In other embodiments utilizing a cleavage-based detection assay, a multiplex reaction may contain multiple probe oligonucleotides having different flaps, multiple different overlapping probe oligonucleotides, and multiple different FRET cassettes for detecting the different flaps, once they are cleaved.

Additional microbe detection assays can be similarly performed for determining the presence and/or relative amount of a plurality of microbes implicated in BV. By way of example only, such plurality of microbes can include one or more of anaerobic gram-positive cocci; *Trichomonas* sp.; *Trichomonas vaginalis*; *Candida* sp.; *Eggerthella* sp.; Bacterium from the order Clostridiales; *Clostridium*-like sp.; *Atopobium* sp.; *Atopobium vaginae*; Enterobacteria; *Peptostreptococcus micros*; *Aerococcus christensenii*; *Leptotrichia amnionii*; *Peptoniphilus* sp.; *Dialister* sp.; *Mycoplasma hominis*; *Sneathia sanguinegens*; *Anaerococcus tetradius*; *Mobiluncus* sp.; *Mobiluncus hominis*; *Eggerthella hongkongensis*; *Prevotella* sp.; *Megasphaera* sp.; *Leptotrichia sanguinegens* and *Finegoldia magna*. Assays may be performed separately or multiplexed. Thus, a diagnosis of BV can include identifying a plurality of microbes and optionally determining their relative abundances in a sample.

In certain embodiments, the method for diagnosing BV includes the detection of no more than ten bacterial genera associated with BV. In other embodiments, the method includes the detection of no more than nine, no more than eight, no more than seven, no more than six, no more than five, or nor more than four bacterial genera associated with BV. In some variations, the method does not include detection of bacterial genera associated with BV other than *Lactobacillus*, *Gardnerella*, and *Eggerthella*.

Also provided by the subject invention is an oligomer for determining the presence or absence of any one or more of *Lactobacillus* sp., *G. vaginalis*, and *Eggerthella* sp. in a sample. In various embodiments, the oligomer combination includes oligomers as set forth herein for a method for determining the presence or absence of *Lactobacillus* sp., *G. vaginalis*, and/or *Eggerthella* sp. in a sample. In some variations, the oligomer combination includes at least one *Lactobacillus*-specific oligonucleotide (e.g., at least two or three *Lactobacillus*-specific oligonucleotides, each binding to different target sequences); at least one *G. vaginalis*-specific oligonucleotide (e.g., at least two or three *G. vaginalis*-specific oligonucleotides, each binding to different target sequences); and at least one *Eggerthella*-specific oligonucleotide (e.g., at least two or three *Eggerthella*-specific oligonucleotides, each binding to different target sequences). In some variations, the oligomer combination includes at least two *Lactobacillus*-specific oligonucleotides (e.g., at least three *Lactobacillus*-specific oligonucleotides, each binding to different target sequences); at least two *G. vaginalis*-specific oligonucleotides (e.g., at least three *G. vaginalis*-specific oligonucleotides, each binding to different target sequences); and/or at least two *Eggerthella*-specific oligonucleotides (e.g., at least three *Eggerthella*-specific oligonucleotides, each binding to different target sequences). In some embodiments, the oligomer combination at least two *Lactobacillus*-specific amplification oligonucleotides for amplifying a *Lactobacillus* sp. nucleic acid target region; at least two *G. vaginalis*-specific amplification oligonucleotides for amplifying a *G. vaginalis* nucleic acid target region; and/or at least two *Eggerthella*-specific amplification oligonucleotides for amplifying an *Eggerthella* sp. nucleic acid target region. The oligomer combination may be in the form of a reaction mixture or a kit comprising the oligomers. The reaction mixture or kit may further include a number of optional components such as, for example, capture probe nucleic acids or arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which an *Eggerthella, Prevotella,* and/or *Lactobacillus* target nucleic acid may or may not be present. A kit comprising an oligomer combination for amplification of one or more target nucleic acid regions of *Lactobacillus* sp., *G. vaginalis*, and/or *Eggerthella* sp. may also include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). For an oligomer combination (e.g., reaction mixture or kit) that includes a detection probe together with an amplification oligomer combination targeting a common target nucleic acid, selection of amplification oligomers and detection probe oligomers are linked by a common target region (i.e., the combination will include a probe that binds to a sequence amplifiable by the amplification oligomer combination).

The invention is further illustrated by the following non-limiting examples.

Example 1: Reagents for RT-TMA-Based Assays

Unless otherwise specified, reagents commonly used in the RT-TMA-based assays described herein include the following. Target Capture Reagent (TCR), General Purpose Reagent formulation: 250 mM HEPES, 1.88 M LiCl, 310 mM LiOH, 100 mM EDTA, pH 6.4, and 250 µg/ml of paramagnetic particles (0.7-1.05 micron particles, Sera-Mag™ MG-CM) with $(dT)_{14}$ oligomers covalently bound thereto. Wash Solution: 10 mM HEPES, 150 mM NaCl, 6.5 mM NaOH, 1 mM EDTA, 0.3% (v/v) ethanol, 0.02% (w/v) methylparaben, 0.01% (w/v) propylparaben, and 0.1% (w/v) sodium lauryl sulfate, pH 7.5. Amplification reagent, Real-Time Reagent formulation: a solution containing 11.61 mM Tris base, 14.94 mM Tris-HCl, 28.5 mM $MgCl_2$, 23.30 mM KCl, 3.3% Glycerol, 0.02% PRO CLIN 300, 0.05 mM Zinc Acetate Dihydrate, 0.76 mM each of dATP, dCTP, dGTP, and dTTP, 6.50 mM each ATP, CTP, and GTP, 7.50 mM UTP, to which primers may be added. RT-TMA Enzymes: 57.46 mM HEPES, 49.58 mM N-Acetyl-L-Cysteine, 0.98 mM EDTA free acid, 0.039 mM EDTA Disodium Dihydrate, 0.10 v/v TRITON X-100, 49.61 mM KCl, 0.20 v/v Glycerol, 0.03 w/v Trehalose Dihydrate, MMLV reverse transcriptase (RT) and T7 RNA polymerase. Promoter Reagent, Real-Time Reagent formulation: same reagent formulation as Amplification Reagent.

Oligo screening experiments for amplification oligos and torches were performed on an OEM platform (Stratagene Mx3000) using the biphasic real-time TMA format. Briefly, samples were incubated with 100 µl TCR reagent, containing target-specific capture oligos (15 pmol/rxn) and T7 oligos (5 pmol/rxn) at 62° C. for 30 minutes, then ramped down to room temperature for 20 minutes. Magnetic beads bound with TCOs and target rRNAs were washed and eluted into the Amplification reagent, containing 15 pmol/rxn NT7 oligos. Samples were incubated at 43° C. during addition of Enzyme Reagent (25 µl) and subsequent addition of Promoter Reagent (25 µl). The Promoter Reagent contained 15 pmol/rxn T7 oligos and 15 pmol/rxn Torch oligos. Fluorescence emission, reflecting Torch binding to target amplicon rRNA and resulting in dye separation from quencher, was measured in real-time on the Stratagene instrument every 30 seconds for 1 hour. Fluorescence curve profiles were analyzed for amplification of target.

Several T7 oligos were screened for the *Lactobacillus* sp. target systems, to identify the optimal combination of these oligos for overall L. spp target detection in the assay. Two T7 oligos were selected for inclusion in the assay. Additional torch oligos were developed and tested to improve the detection of *L. gasseri* specifically, and reduce cross-detection of *Lactobacillus iners* (a non-target *Lactobacillus* species). Several torches showed good performance for *L. gasseri*, and one showed the best reduction in *L. iners* cross-detection. Two different T7 oligos for *G. vaginalis* were screened for possible inclusion of a competitive internal control for the assay, utilizing the T7/NT7 oligos for *G. vaginalis* and torch-specific oligos for *G. vaginalis* versus IC detection. Different target-specific target capture oligos were designed and screened, comparing performance of the assay for each target system to a common BV target capture oligo. One target-specific TCO was selected for each BV target system. Additional TCOs were screened for the L. spp targets, and one TCO was selected that provided the best balance in detection for the three L. spp targets overall. A list of the primers screened for optimization of the multiplex bacterial vaginosis assay are listed in Table 1.

Following optimization of target amplification and detection, oligos were selected for each BV target and subsequent experiments were carried out on the Panther instrument platform. The amplification and detection reaction was configured to amplify and detect all specified BV targets as well as a nucleic acid internal control. Briefly, lysed target was combined with target capture oligos, magnetic beads joined to immobilized probes, and T7 primers. Reaction conditions were provided to hybridize the target capture oligos and the T7 primers to their intended targets. A series of wash steps were performed to remove cellular components, culture and transport medium and the like. Following the wash step, a first amplification reagent was added to the washed and captured target nucleic acids. The first amplification reagent contained only non-T7 primers. There was no primer-annealing step prior to enzyme addition; initiation of amplification occurred at addition of enzyme, and was followed by a 5-minute incubation step at 42° C. The second amplification reagent containing T7 primers and torches as detection probes was added to the first amplification reagent after a 5-minute 42° C. incubation reaction. Real-time detection occurred during this step measured by 4 separate fluorometers used to detect Fam, Hex, Rox, and Cy5.5 dye labels on each of the different detection probes.

Example 2: Sensitivity and Specificity Testing of Oligomer Combinations for Amplification and Detection of BV Target Nucleic Acid Analytical sensitivity of BV targets was assessed testing half-log titrations of lysates (for L. spp targets and *G. vaginalis*), or in vitro transcripts (IVTs) for *Eggerthella*, spiked into Aptima Specimen Transport Medium (STM). Fifteen replicates were screened at each panel concentration (N=10 total concentrations, for each target) on the Panther instrument. Oligos were tested in multiplex-kit format; however, each BV target was screened separately. The assays used TCO primers (15 pmol/rxn), T7 primers (at either 5 or 15 pmol/rxn), NT7 primers (15 pmol/rxn), and Torch primers (15 pmol/rxn). A Probit analysis was performed to determine the 95% and 50% detection levels for each of the BV targets. At 95% Probability (95% CL), limit-of-detection (LoD) was determined: *L. crispatus,* 3.4e4 (3.2e4-3.5e4) CFU/ml; *L. jensenii,* 3.1e3 (3.0e3-3.2e3) CFU/ml; *L. gasseri,* 3.2e3 (3.1e3-3.2e3) CFU/ml; *G. vaginalis,* 107 (103-110) CFU/ml; *Eggerthella,* 1.1e8 (1.0e8-1.2e8) copies/ml.

Cross-reactivity of optimal primer sets for each BV target was tested against 16 pooled panels of 4-5 organisms each. No significant cross-detection of any of the organisms was observed for the primer set optimized to detect *G. vaginalis.* The primer set optimized to detect the L. spp targets cross-reacted with 1 of the pooled panels screened. Additional experiments determined that the cross-reacting organism was *Lactobacillus acidophilus. L. acidophilus* is a gut microbe and was determined to be no risk for the assay. The primer set optimized to detect the *Eggerthella* target cross-reacted with 1 of the pooled panels screened. Additional experiments determined that the cross-reacting organism was *Neisseria gonorrhoeae. N. gonorrhoeae* was a high-risk cross-detection, and additional primers were screened for *Eggerthella.* The new optimized primer set successfully eliminated detection of *N. gonorrhoeae* up to 1e7 CFU/ml.

Example 3: Clinical Sensitivity of RT-TMA Assay for Detecting BV Target Nucleic Acids Clinical performance of the bacterial vaginosis assay was assessed using vaginal swab patient specimens (n=200, collected from four different clinical sites), and included roughly 100 positive and 100 negative samples (utilizing Cartwright criteria). TTime was used as a cutoff in each fluorescent channel utilized for target detection (Fam, Hex, Cy5.5): L. spp, 25 minutes; *G. vaginalis,* 12.5 minutes; *Eggerthella,* 40 minutes. The bacterial vaginosis assay clinical performance was analyzed for sensitivity: 93.8% (86.2-97.3), and specificity: 88.6% (79.7-93.9).

Ninety-eight ThinPrep/vaginal swab paired samples were also assessed for clinical feasibility and the bacterial vaginosis assay performance, including a roughly equal amount of positive and negative samples (utilizing Cartwright criteria). Overall agreement for positive samples=93.8%; overall agreement for negative samples=100%; overall agreement for intermediate samples=87.5%.

Example 4: Clinical Sensitivity of RT-TMA Assay for Detecting BV Target Nucleic Acids For this testing, Amplification and Promoter reagent formulations were adjusted compared to those previously described in Example 1. Amplification reagent, Real-Time Reagent formulation: a solution containing 11.61 mM Tris base, 14.94 mM Tris-HCl, 31.0 mM $MgCl_2$, 23.30 mM KCl, 3.3% Glycerol, 0.02% PRO CLIN 300, 0.05 mM Zinc Acetate Dihydrate, 0.83 mM each of dATP, dCTP, dGTP, and dTTP, 7.00 mM each ATP, CTP, and GTP, 8.00 mM UTP, to which primers may be added. RT-TMA Enzymes: 57.46 mM HEPES, 49.58 mM N-Acetyl-L-Cysteine, 0.98 mM EDTA free acid, 0.039 mM EDTA Disodium Dihydrate, 0.10 v/v TRITON X-100, 49.61 mM KCl, 0.20 v/v Glycerol, 0.03 w/v Trehalose Dihydrate, MMLV reverse transcriptase (RT) and T7 RNA polymerase. Promoter Reagent, Real-Time Reagent formulation: same reagent formulation as Amplification Reagent.

Oligo concentration optimization experiments were carried out to determine the optimal concentration for each oligo of the bacterial vaginosis assay. The oligo concentrations were titrated and screened against target IVTs spiked into STM at concentrations that would demonstrate differences in performance. From this testing it was determined to adjust the oligo concentrations to optimize performance of the assay. For the TCR reagent, the TCOs for *Lactobacillus* sp., *Eggerthella,* and *Gardnerella* were adjusted from 15 pmol/rxn to 10 pmol/rxn. All T7 primers were removed from the TCR reagent. For the Amplification reagent, the NT7 for *Eggerthella* was adjusted from 15 pmol/rxn to 10 pmol/rxn, and the NT7s for *Lactobacillus* and *Gardnerella* were adjusted from 15 pmol/rxn to 5 pmol/rxn. For the T7 oligos in the Promoter reagent, *Lactobacillus* sp. T7 oligo SEQ ID NO:7 was removed from the formulation, *Lactobacillus* T7 oligo SEQ ID NO:8 remained in the formulation and was adjusted from 15 pmol/rxn to 4 pmol/rxn, the *Eggerthella* T7 was adjusted from 15 pmol/rxn to 10 pmol/rxn, and the *Gardnerella* T7 was adjusted from 15 pmol/rxn to 5 pmol/rxn. For the torch oligos in the Promoter reagent, the *Lactobacillus* sp. torch for *L. gasseri* detection (SEQ ID NO:10) was adjusted from 15 pmol/rxn to 10 pmol/rxn, the *Lactobacillus* sp. torch for *L. crispatus* and *L. jensenii* detection was adjusted from 15 pmol/rxn to 20 pmol/rxn, and the *Gardnerella* torch and *Eggerthella* torch were adjusted from 15 pmol/rxn to 20 pmol/rxn.

Clinical performance of the bacterial vaginosis assay was assessed using vaginal swab patient specimens (n=353, collected from three different clinical sites), and included 78 positive, 41 intermediates, and 234 negatives according to culture result. Intermediate status was resolved with Amsel criteria resulting in 4 positive and 37 negative. Positive criteria was determined if the sample had an RFU signal that exceeded 2000 RFU in FAM, 2000 RFU in HEX, and/or 1600 RFU in ROX. A positive result in FAM channel corresponded to positive result for *Lactobacillus* sp., a positive result in HEX corresponded to a positive result for *Eggerthella,* and a positive result in the ROX channel corresponded to a positive all for *Gardnerella.* No TTime cutoff was utilized to determine a positive result. The bacterial vaginosis assay clinical performance was analyzed for sensitivity and specificity with and without the inclusion of the *Eggerthella* target. The sensitivity of the assay was 96.3 (89.7-99.2) with *Eggerthella* and 96.3 (89.7-99.2) without *Eggerthella.* The specificity of the assay was 86.7 (82.1-90.5) with *Eggerthella* and 87.5 (82.9-91.2) without *Eggerthella.* Better specificity is gained with the exclusion of *Eggerthella* detection from the sample testing results (the improved specificity was due to removal of false positives). Furthermore, the *Eggerthella* result was only found to be positive when *Gardnerella* was also determined to be positive a result, and no BV positive sample was determined by using *Eggerthella* status alone. The results demonstrate that improved specificity is gained by the exclusion of *Eggerthella* from the BV assay formulation and thus supports the removal from the assay.

TABLE 3

Oligos Screened for the Bacterial Vaginosis Assay

| SEQ ID NO: | Sequence (5' → 3') | Type |
|---|---|---|
| 12 | CTTACCTGGGCTTGACATGTGCCTG | NT7 |
| 19 | GGATTCATTGGGCGTAAAGC | NT7 |
| 6 | CGGATGGGTGAGTAAC | NT7 |

TABLE 3-continued

Oligos Screened for the Bacterial Vaginosis Assay

| SEQ ID NO: | Sequence (5' → 3') | Type |
|---|---|---|
| 20 | GCGTTATCCGGATTCAT | NT7 |
| 16 | AGCGTTATCCGGATTC | NT7 |
| 13 | AATTTAATACGACTCACTATAGGGAGACACCACCTGTGAAC CTGC | T7 |
| 17 | AATTTAATACGACTCACTATAGGGAGATTCGGAACCCGGCT CGAGGTTAAG | T7 |
| 21 | AATTTAATACGACTCACTATAGGGAGATAAGCCTTTACCTT ACCA | T7 |
| 22 | AATTTAATACGACTCACTATAGGGAGAATACGACAGCTTAC GCCGC | T7 |
| 23 | AATTTAATACGACTCACTATAGGGAGATATCTGCGCATTTC ACCGCTACAC | T7 |
| 8 | AATTTAATACGACTCACTATAGGGAGATAAGCCGTTACCTT ACCA | T7 |
| 7 | AATTTAATACGACTCACTATAGGGAGATAAGCCCTTACCTT ACCA | T7 |
| 24 | AATTTAATACGACTCACTATAGGGAGACGACCATGCACCAC CTGT | T7 |
| 25 | GGACUACCAGGGUAUCUAAUCCUGUUUAAAAAAAAAAAAAA AAAAAAAAAAAAAA | TCO |
| 11 | CAUGCUCCGCCGCUUGUUUAAAAAAAAAAAAAAAAAAAAA AAAAAAAAA | TCO |
| 15 | GUACCGUCGAUGUCUUCCCUGUUUAAAAAAAAAAAAAAAA AAAAAAAAAAAA | TCO |
| 26 | GUAGGAGUUUGGGCCGUGUUUAAAAAAAAAAAAAAAAAA AAAAAAAAAA | TCO |
| 5 | UCUGUUAGUUCCUUUAAAAAAAAAAAAAAAAAAAAAAAA AAAAA | TCO |
| 27 | CUUUGAGUUUUAGCCUUGCGUUUAAAAAAAAAAAAAAAAA AAAAAAAAAAA | TCO |
| 28 | GCAUCGAAUUAAUCCGCAUGCUUUAAAAAAAAAAAAAAAA AAAAAAAAAAAA | TCO |
| 29 | GUAGUUAGCCGGGGCUUCUUCUUUAAAAAAAAAAAAAAAAA AAAAAAAAAAA | TCO |
| 30 | UACGUAUUACCGCGGCUGUUUAAAAAAAAAAAAAAAAAA AAAAAAAAAA | TCO |
| 31 | CGUGUCUCAGUCCCAAUGUGUUUAAAAAAAAAAAAAAAAA AAAAAAAAAAA | TCO |
| 32 | CAAUGUGGCCGAUCAGUCUUUAAAAAAAAAAAAAAAAAA AAAAAAAAA | TCO |
| 33 | CCAUUGUGGAAGAUUCCCUACUUUAAAAAAAAAAAAAAAA AAAAAAAAAAAA | TCO |
| 34 | CUCGCUCGACUUGCAUGUAUUUAAAAAAAAAAAAAAAAA AAAAAAAAAA | TCO |
| 35 | CUUGCAUGUAUUAGGCACGUUUAAAAAAAAAAAAAAAAA AAAAAAAAAA | TCO |
| 36 | CUUGUAUCUAUGUCCAUUCCUUUAAAAAAAAAAAAAAAAA AAAAAAAAAAA | TCO |
| 37 | UGGUGCAAGCACCAAAUUCUUUAAAAAAAAAAAAAAAAAA AAAAAAAAAAA | TCO |
| 38 | AAUUCAUCUAGGCAAGUUUAAAAAAAAAAAAAAAAAAAA AAAAAAAAA | TCO |
| 39 | UCCUAACGUCAUUACCUUUAAAAAAAAAAAAAAAAAAAA AAAAAAAAA | TCO |
| 40 | UCCAUUCCGAAGAAUUUAAAAAAAAAAAAAAAAAAAAAA AAAAAAA | TCO |
| 41 | UUGCUGCGUCAGGGUUUCCUUUAAAAAAAAAAAAAAAAAA AAAAAAAAAAA | TCO |
| 42 | GAAAGCGGUUUACAACCCGAUUUAAAAAAAAAAAAAAAAA AAAAAAAAAAAA | TCO |
| 43 | AAGGCCUUCAUCCCGCAUUUAAAAAAAAAAAAAAAAAAA AAAAAAAAA | TCO |
| 44 | UCGCCGUUGGUGUUCUUCUUUAAAAAAAAAAAAAAAAAA AAAAAAAAAAA | TCO |
| 45 | UGACGGCCCAGCAGACUUUAAAAAAAAAAAAAAAAAAAA AAAAAAAAA | TCO |
| 46 | UCCUGUUCGCUCCCCCAGCUUUAAAAAAAAAAAAAAAAAA AAAAAAAAAAAA | TCO |
| 47 | TCCTAACGTCATTACCTTTAAAAAAAAAAAAAAAAAAAAA AAAAAAAA | TCO |
| 48 | GTACCGTCGATGTCTTCCCTGTTTAAAAAAAAAAAAAAAAA AAAAAAAAAAAA | TCO |
| 49 | CAGCGCUCAUCGUUUUAAAAAAAAAAAAAAAAAAAAAAA AAAAAAA | TCO |
| 50 | ACGGAAGAUGUAAUCUCUUUAAAAAAAAAAAAAAAAAAA AAAAAAAAA | TCO |
| 51 | GAUGUAAUCUCCCACUUUAAAAAAAAAAAAAAAAAAAAA AAAAAAAA | TCO |
| 52 | CCAUUCCGAAGAUUUAAAAAAAAAAAAAAAAAAAAAAA AAAAA | TCO |
| 53 | AGUUUCAUCUGUUUAAAAAAAAAAAAAAAAAAAAAAAAA AAAA | TCO |
| 54 | CCGAAGAAUUUCUUUAAAAAAAAAAAAAAAAAAAAAAAA AAAAA | TCO |
| 55 | UUCAAUAGGCUUUAAAAAAAAAAAAAAAAAAAAAAAAAA AAA | TCO |
| 56 | CGUCAUUACCUUUAAAAAAAAAAAAAAAAAAAAAAAAAA AAA | TCO |
| 57 | CCAAAUUCAUCUUUUAAAAAAAAAAAAAAAAAAAAAAAA AAAAA | TCO |
| 58 | AACGUCAUUACCUUUAAAAAAAAAAAAAAAAAAAAAAAA AAAAA | TCO |
| 59 | UUUCCUAACGUCUUUAAAAAAAAAAAAAAAAAAAAAAAA AAAAA | TCO |
| 60 | CCUGCAGAGAUGUGGUUUCGCAGG | Torch |
| 18 | CCGCUCAGGCGGUUGCUCAAGCGG | Torch |
| 9 | GUCUGGGAUACCACUUGGAAACAGAC | Torch |

TABLE 3-continued

Oligos Screened for the Bacterial Vaginosis Assay

| SEQ ID NO: | Sequence (5' → 3') | Type |
|---|---|---|
| 61 | CUGGGAUACCACUUGGAAACACCCAG | Torch |
| 62 | UCUGGGAUACCACUUCCAGA | Torch |
| 14 | CCUGCAGAGAUGUGGUUUCGCAGG | Torch |
| 63 | CCUGCAGAGAUGUGGUUUCGCAGG | Torch |
| 64 | GGUUCUGCUAUCACUCUUGGAACC | Torch |
| 65 | ACGCAUGUCUAGAGUUGCGU | Torch |
| 66 | AGACGCAUGUCUAGAGCGUCU | Torch |
| 67 | GAUGCUAAUACCGGAUAACAACGCAUC | Torch |
| 68 | UACCGGAUAACAACACUAGACGCCGGUA | Torch |
| 69 | GUCUGGGAUACCAUUUGGAAACAGAC | Torch |
| 70 | GUCUGGGAUACCACUUGGAAACAGAC | Torch |
| 71 | GUCUGGGAUACCACUUGGAAACAGAC | Torch |
| 72 | GGUUCUGCUAUCACUCUUGGAACC | Torch |
| 73 | GGUUCUGCUAUCACUCUUGGAACC | Torch |
| 74 | CGCAUGUCUAGAGUUGCG | Torch |
| 75 | ACUCACGCAUGUCUAGAGU | Torch |
| 10 | CACUCACGCAUGUCUAGAGUG | Torch |
| 76 | GAGACGCAUGUCUAGAGUUGUCUC | Torch |
| 77 | GUUGCUCAAGCGGAACCUCGCAAC | Torch |
| 78 | UUGCUCAAGCGGAACCUCUAGCAA | Torch |
| 79 | GCUCAAGCGGAACCUCUGAGC | Torch |
| 80 | AGCGGAACCUCUAAUCUCGUCGCU | Torch |
| 81 | CCGCUCAGGCGGUUGCUCAAGCGG | Torch |
| 82 | CCGCUCAGGCGGUUGCUCAAGCGG | Torch |
| 83 | CCGCUCAGGCGGUUGCUCAAGCGG | Torch |
| 84 | CCGCUCAGGCGGUUGCUCAAGCGG | Torch |
| 85 | CCGCUCAGGCGGUUGCUCAAGCGG | Torch |
| 86 | CCGCUCAGGCGGUUGCUCAAGCGG | Torch |
| 87 | CCGCUCAGGCGGUUGCUCAAGCGG | Torch |

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

\*\*\*\*\*\*\*\*\*\*\*\*\*\*\*\*\*\*\*\*\*\*\*\*\*\*\*\*\*\*

---

What is claimed is:

1. A multiplex method for determining the presence or absence of each of *Lactobacillus* sp., *G. vaginalis*, and *Eggerthella* sp. in a clinical sample, the method comprising:
    (1) contacting a clinical sample, said sample suspected of containing at least one of *Lactobacillus* sp., *G. vaginalis*, and *Eggerthella* sp., with
        (a) first, second, and third *Lactobacillus*-specific amplification oligomers for amplifying a target region of a *Lactobacillus* sp. target nucleic acid, wherein (i) the first *Lactobacillus*-specific amplification oligomer comprises a first *Lactobacillus*-specific target-hybridizing sequence consisting of the nucleotide sequence of residues 28-45 of SEQ ID NO:7, (ii) the second *Lactobacillus*-specific amplification oligomer comprises a second *Lactobacillus*-specific target-hybridizing sequence consisting of the nucleotide sequence of SEQ ID NO:6, and (iii) the third *Lactobacillus*-specific amplification oligomer comprises a third *Lactobacillus*-specific target-hybridizing sequence consisting of the nucleotide sequence of residues 28-45 of SEQ ID NO:8;
        (b) first and second *G. vaginalis*-specific amplification oligomers for amplifying a target region of a *G. vaginalis* target nucleic acid, wherein (i) the first *G. vaginalis*-specific amplification oligomer comprises a first *G. vaginalis*-specific target-hybridizing sequence consisting of the nucleotide sequence of residues 28-45 of SEQ ID NO:13 and (ii) the second *G. vaginalis*-specific amplification oligomer comprises a second *G. vaginalis*-specific target-hybridizing sequence consisting of the nucleotide sequence of SEQ ID NO:12; and
        (c) first and second *Eggerthella*-specific amplification oligomers for amplifying a target region of an *Egg-*

*erthella* sp. target nucleic acid, wherein (i) the first *Eggerthella*-specific amplification oligomer comprises a first *Eggerthella*-specific target-hybridizing sequence consisting of the nucleotide sequence of residues 28-51 of SEQ ID NO:17 and (ii) the second *Eggerthella*-specific amplification oligomer comprises a second *Eggerthella*-specific target-hybridizing sequence consisting of the nucleotide sequence of SEQ ID NO:16;

wherein each of the first *Lactobacillus*-specific amplification oligomer, the third *Lactobacillus*-specific amplification oligomer, the first *G. vaginalis*-specific amplification oligomer, and the first *Eggerthella* specific amplification oligomer is a promoter primer or promoter provider further comprising a T7 promoter sequence located 5' to the respective target-hybridizing sequence;

(2) performing an in vitro nucleic acid amplification reaction, wherein any *Lactobacillus* sp., *G. vaginalis*, and *Eggerthella* sp. target nucleic acid, if present in the sample, is used as a template for generating one or more amplification products corresponding to the *Lactobacillus* sp., *G. vaginalis*, and *Eggerthella* sp. target regions; and (3) detecting the presence or absence of the one or more amplification products, thereby determining the presence or absence of *Lactobacillus* sp., *G. vaginalis*, and *Eggerthella* sp. in the sample.

2. The method of claim 1, wherein
the nucleotide sequence of the first *Lactobacillus*-specific amplification oligomer consists of the sequence of SEQ ID NO:7;
the nucleotide sequence of the third *Lactobacillus*-specific amplification oligomer consists of the sequence of SEQ ID NO:8;
the nucleotide sequence of the first *G. vaginalis*-specific amplification oligomer consists of the sequence of SEQ ID NO:13; and/or
the nucleotide sequence of the first *Eggerthella*-specific amplification oligomer consists of the sequence of SEQ ID NO:17.

3. The method of claim 1, further comprising purifying the *Lactobacillus*, *G. vaginalis*, and *Eggerthella* target nucleic acids, if present, from other components in the sample before step (2).

4. The method of claim 1, wherein the detecting step (3) comprises
contacting the one or more amplification products with a first *Lactobacillus*-specific detection probe that specifically hybridizes to the *Lactobacillus* sp. target region, a first *G. vaginalis*-specific detection probe that specifically hybridizes to the *G. vaginalis* target region, and a first *Eggerthella*-specific detection probe that specifically hybridizes to the *Eggerthella* sp. target region, and
detecting the presence or absence of any target-hybridized *Lactobacillus*-specific, *G. vaginalis*-specific, and/or *Eggerthella*-specific detection probe.

5. The method of claim 4, wherein
the first *Lactobacillus*-specific detection probe comprises a target-hybridizing sequence consisting of SEQ ID NO:9,
the first *G. vaginalis*-specific detection probe comprises a target-hybridizing sequence consisting of residues 1-19 of SEQ ID NO:14, and/or
the first *Eggerthella*-specific detection probe comprises a target-hybridizing sequence consisting of SEQ ID NO:18.

6. The method of claim 4, wherein each of the first *Lactobacillus*-specific detection probe, the first *G. vaginalis*-specific detection probe, and the first *Eggerthella*-specific detection probe comprises a label.

7. The method of claim 6, wherein the label is a chemiluminescent label or a fluorescent label.

8. An oligomer combination for determining the presence or absence of each of *Lactobacillus* sp., *G. vaginalis*, and *Eggerthella* sp. in a clinical sample, the oligomer combination comprising:

(a) first, second, and third *Lactobacillus*-specific amplification oligomers for amplifying a target region of a *Lactobacillus* sp. target nucleic acid, wherein (i) the first *Lactobacillus*-specific amplification oligomer comprises a first *Lactobacillus*-specific target-hybridizing sequence consisting of the nucleotide sequence of residues 28-45 of SEQ ID NO:7, (ii) the second *Lactobacillus*-specific amplification oligomer comprises a second *Lactobacillus*-specific target-hybridizing sequence consisting of the nucleotide sequence of SEQ ID NO:6, and (iii) the third *Lactobacillus*-specific amplification oligomer comprises a third *Lactobacillus*-specific target-hybridizing sequence consisting of the nucleotide sequence of residues 28-45 of SEQ ID NO:8;

(b) first and second *G. vaginalis*-specific amplification oligomers for amplifying a target region of a *G. vaginalis* target nucleic acid, wherein (i) the first *G. vaginalis*-specific amplification oligomer comprises a first *G. vaginalis*-specific target-hybridizing sequence consisting of the nucleotide sequence of residues 28-45 of SEQ ID NO:13 and (ii) the second *G. vaginalis*-specific amplification oligomer comprises a second *G. vaginalis*-specific target-hybridizing sequence consisting of the nucleotide sequence of SEQ ID NO:12; and (c) first and second *Eggerthella*-specific amplification oligomers for amplifying a target region of an *Eggerthella* sp. target nucleic acid, wherein (i) the first *Eggerthella*-specific amplification oligomer comprises a first *Eggerthella*-specific target-hybridizing sequence consisting of the nucleotide sequence of residues 28-51 of SEQ ID NO:17 and (ii) the second *Eggerthella*-specific amplification oligomer comprises a second *Eggerthella*-specific target-hybridizing sequence consisting of the nucleotide sequence of SEQ ID NO:16;

wherein each of the first *Lactobacillus*-specific amplification oligomer, the third *Lactobacillus*-specific amplification oligomer, the first *G. vaginalis*-specific amplification oligomer, and the first *Eggerthella* specific amplification oligomer is a promoter primer or promoter provider further comprising a T7 promoter sequence located 5' to the respective target-hybridizing sequence.

9. The oligomer combination of claim 8, wherein
the nucleotide sequence of the first *Lactobacillus*-specific amplification oligomer consists of the sequence of SEQ ID NO:7;
the nucleotide sequence of the third *Lactobacillus*-specific amplification oligomer consists of the sequence of SEQ ID NO:8;
the nucleotide sequence of the first *G. vaginalis*-specific amplification oligomer consists of the sequence of SEQ ID NO:13; and/or the nucleotide sequence of the first *Eggerthella*-specific amplification oligomer consists of the sequence of SEQ ID NO:17.

10. The oligomer combination of claim 8, further comprising a first *Lactobacillus*-specific detection probe that specifically hybridizes to the *Lactobacillus* sp. target region, a first *G. vaginalis*-specific detection probe that specifically hybridizes to the *G. vaginalis* target region, and a first *Eggerthella*-specific detection probe that specifically hybridizes to the *Eggerthella* sp. target region.

11. The method of claim 5, wherein the detecting step (3) further comprises contacting the one or more amplification products with a second *Lactobacillus*-specific detection probe that specifically hybridizes to the *Lactobacillus* sp. target region, wherein the second *Lactobacillus*-specific detection probe comprises a target-hybridizing sequence consisting of residues 6-21 of SEQ ID NO:10.

* * * * *

SEQUENCE LISTING

<160> NUMBER OF SEQ ID NOS: 88

<210> SEQ ID NO 1
<211> LENGTH: 1518
<212> TYPE: DNA
<213> ORGANISM: Lactobacillus crispatus
<300> PUBLICATION INFORMATION:
<308> DATABASE ACCESSION NUMBER: GenBank/NR_041800.1 GI:343201103
<309> DATABASE ENTRY DATE: 2011-08-10
<313> RELEVANT RESIDUES IN SEQ ID NO: (1)..(1518)

<400> SEQUENCE: 1

```
gacgaacgct ggcggcgtgc ctaatacatg caagtcgagc gagcggaact aacagattta      60
cttcggtaat gacgttagga aagcgagcgg cggatgggtg agtaacacgt ggggaacctg     120
ccccatagtc tgggatacca cttggaaaca ggtgctaata ccggataaga aagcagatcg     180
catgatcagc ttttaaaagg cggcgtaagc tgtcgctatg ggatggcccc gcggtgcatt     240
agctagttgg taaggtaaag gcttaccaag gcgatgatgc atagccgagt tgagagactg     300
atcggccaca ttgggactga gacacggccc aaactcctac gggaggcagc agtagggaat     360
cttccacaat ggacgcaagt ctgatggagc aacgccgcgt gagtgaagaa ggttttcgga     420
tcgtaaagct ctgttgttgg tgaagaagga tagaggtagt aactggcctt tatttgacgg     480
taatcaacca gaaagtcacg gctaactacg tgccagcagc cgcggtaata cgtaggtggc     540
aagcgttgtc cggatttatt gggcgtaaag cgagcgcagg cggaagaata agtctgatgt     600
```

```
gaaagccctc ggcttaaccg aggaactgca tcggaaactg ttttcttga gtgcagaaga      660 ggagagtgga actccatgtg tagcggtgga atgcgtagat atatggaaga acaccagtgg      720
cgaaggcggc tctctggtct gcaactgacg ctgaggctcg aaagcatggg tagcgaacag      780
gattagatac cctggtagtc catgccgtaa acgatgagtg ctaagtgttg ggaggtttcc      840
gcctctcagt gctgcagcta acgcattaag cactccgcct ggggagtacg accgcaaggt      900
tgaaactcaa aggaattgac gggggcccgc acaagcggtg gagcatgtgg tttaattcga      960
agcaacgcga agaaccttac caggtcttga catctagtgc catttgtaga gatacaaagt     1020
tcccttcggg gacgctaaga caggtggtgc atggctgtcg tcagctcgtg tcgtgagatg     1080
ttgggttaag tcccgcaacg agcgcaaccc ttgttattag ttgccagcat taagttgggc     1140
actctaatga gactgccggt gacaaaccgg aggaaggtgg ggatgacgtc aagtcatcat     1200
gccccttatg acctgggcta cacacgtgct acaatgggca gtacaacgag aagcgagcct     1260
gcgaaggcaa gcgaatctct gaaagctgtt ctcagttcgg actgcagtct gcaactcgac     1320
tgcacgaagc tggaatcgct agtaatcgcg gatcagcacg ccgcggtgaa tacgttcccg     1380
ggccttgtac acaccgcccg tcacaccatg gagtctgca atgcccaaag ccggtggcct     1440
aaccttcggg aaggagccgt ctaaggcagg gcagatgact ggggtgaagt cgtaacaagg     1500
tagccgtagg agaactgc                                                   1518

<210> SEQ ID NO 2
<211> LENGTH: 1529
<212> TYPE: DNA
<213> ORGANISM: Lactobacillus gasseri
<300> PUBLICATION INFORMATION:
<308> DATABASE ACCESSION NUMBER: GenBank/HE573914.1 GI:341599788
<309> DATABASE ENTRY DATE: 2011-07-25
<313> RELEVANT RESIDUES IN SEQ ID NO: (1)..(1529)

<400> SEQUENCE: 2
ctgcggcgtg cctaatacat gcaagtcgag cgagcttgcc tagatgaatt tggtgcttgc       60
accagatgaa actagataca agcgagcggc ggacgggtga gtaacacgtg gtaacctgc      120 ccaagagact gggataacac ctggaaacag atgctaatac cggataacaa cactagacgc      180
atgtctagag tttaaaagat ggttctgcta tcactcttgg atggacctgc ggtgcattag      240
ctagttggta aggtaacggc ttaccaaggc aatgatgcat agccgagttg agagactgat      300
cggccacatt gggactgaga cacggcccaa actcctacgg aggcagcag tagggaatct      360 tccacaatgg acgcaagtct gatggagcaa cgccgcgtga gtgaagaagg gtttcggctc      420
gtaaagctct gttggtagtg aagaaagata gaggtagtaa ctggcctta tttgacggta      480 attacttaga aagtcacggc taactacgtg ccagcagccg cggtaatacg taggtggcaa      540
gcgttgtccg gatttattgg gcgtaaagcg agtgcaggcg gttcaataag tctgatgtga      600
aagccttcgg ctcaaccgga gaattgcatc agaaactgtt gaacttgagt gcagaagagg      660
agagtggaac tccatgtgta gcggtggaat gcgtagatat atggaagaac accagtggcg      720
aaggcggctc tctggtctgc aactgacgct gaggctcgaa agcatgggta gcgacagga      780 ttagataccc tggtagtcca tgccgtaaac gatgagtgct aagtgttggg aggtttccgc      840
ctctcagtgc tgcagctaac gcattaagca ctccgcctgg ggagtacgac cgcaaggttg      900
aaactcaaag gaattgacgg gggcccgcac aagcggtgga gcatgtggtt taattcgaag      960
caacgcgaag aaccttacca ggtcttgaca tccagtgcaa acctaagaga ttaggtgttc     1020
```

```
ccttcgggga cgctgagaca ggtggtgcat ggctgtcgtc agctcgtgtc gtgagatgtt      1080
gggttaagtc ccgcaacgag cgcaacccett gtcattagtt gccatcatta agttgggcac     1140
tctaatgaga ctgccggtga caaaccggag gaaggtgggg atgacgtcaa gtcatcatgc      1200
cccttatgac ctgggctaca cacgtgctac aatggacggt acaacgagaa gcgaacctgc     1260
gaaggcaagc ggatctctga aagccgttct cagttcggac tgtaggctgc aactcgccta     1320
cacgaagctg gaatcgctag taatcgcgga tcagcacgcc gcggtgaata cgttcccggg     1380
ccttgtacac accgcccgtc acaccatgag agtctgtaac acccaaagcc ggtgggataa     1440
cctttatagg agtcagccgt ctaaggtagg acagatgatt agggtgaagt cgtaacaagg     1500
tagccgtagg agaacctgcg gttggatca                                        1529

<210> SEQ ID NO 3
<211> LENGTH: 1475
<212> TYPE: DNA
<213> ORGANISM: Gardnerella vaginalis
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (1012)..(1012)
<223> OTHER INFORMATION: n is a, c, g, or t
<220> FEATURE:
<221> NAME/KEY: misc_feature
<222> LOCATION: (1156)..(1156)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1277)..(1277)
<223> OTHER INFORMATION: n is a, c, g, or t
<300> PUBLICATION INFORMATION:
<308> DATABASE ACCESSION NUMBER: GenBank/NR_044694.2 GI:545589071
<309> DATABASE ENTRY DATE: 2013-09-24
<313> RELEVANT RESIDUES IN SEQ ID NO: (1)..(1475)

<400> SEQUENCE: 3
tttcgtggag ggttcgattc tggctcagga tgaacgctgg cggcgtgctt aacacatgcn       60
agtcgaacgg gatctgacca gcttgctggt tggtgagagt ggcgaacggg tgagtaatgc      120
gtgaccaacc tgccccatgc tccagaatag ctcttggaaa cgggtggtaa tgctggatgc      180
tccaacttga cgcatgtctt gttgggaaag tgtttagtgg catgggatgg ggtcgcgtcc      240
tatcagcttg taggcggggt aatggcccac ctaggcttcg acgggtagcc ggcctgagag      300
```

```
ggcggacggc cacattggga ctgagatacg gcccagactn ctacgggagg cagcagtggg      360
gaatattgcg caatggggga acccctgacg cagcgacgnc gcgtgcggga tgaaggcctt      420
cgggttgtaa accgcttttg attgggagca agccttttgg gtgagtgtac ctttcgaata      480
agcgccggct aactacgtgc cagcagccgc ggtaatacgt agggcgcaag cgttatccgg      540
aattattggg cgtaaagagc ttgtaggcgg ttcgtcgcgt ctggtgtgaa agcccatcgc      600
ttaacggtgg gnttgcgccg ggtacgggcg gctagagtg cagtagggga gactggaatt       660
ctcggtgtaa cggtggaatg tgtagatatc gggaagaaca ccaatggcga aggcaggtct      720
ctgggctgtt actgacgctg agaagcgaaa gcgtggggag cgaacaggat tagatacccct    780 ggtagtccac gccgtaaacg gtggacgctg gatgtggggc ccattccacg ggttctgtgt      840
cggagctaac gcgttaagcg tcccgcctgg ggagtacggc cgcaaggcta aaactcaaag      900
aaattgacgg gggccngcac aagcggcgga gcatgcggat taattcgatg naacgcgaag      960
aaccttacct gggcttgaca tgtgcctgac gactgcagag atgtggtttc cnttcggggc     1020
aggttcacag gtggtgcatg gtcgtcgtca gctcgtgtcg tgagatgttg ggttaagtcc     1080
cgcaacgagc gcaaccctcg ccctgtgttg ccagcgggtt atgccgggaa ctcacggggg     1140
accgccgggg ttaccncgga ggaaggtggg natgacgtca gatcatcatg ccccttacgt     1200
ccagggcttc acgcatgcta caatggccag tacaacgggt tgcttcatgg tgacatggtg     1260
ctaatccctt aaaactngtc tcagttcgga tcgtagtctg caactcgact acgtgaaggc     1320
ggagtcgcta gtaatcgcga atcagcaacg tcgcggtgaa tgcgttcccg ggccttgtac     1380
acaccgcccg tcaagtcatg aaagtgggca gcacccgaag ccggtggcct aacccttttg     1440
ggatggagcc gtctaaggtg aggctcgtga ttggg                                1475
```

<210> SEQ ID NO 4
<211> LENGTH: 1000
<212> TYPE: DNA
<213> ORGANISM: Uncultured Eggerthella sp. clone 123-f2 68
<300> PUBLICATION INFORMATION:
<308> DATABASE ACCESSION NUMBER: GenBank/AY738656.1 GI:52222145
<309> DATABASE ENTRY DATE: 2005-11-02
<313> RELEVANT RESIDUES IN SEQ ID NO: (1)..(1000)

<400> SEQUENCE: 4

```
tggggaatat tgcgcaatgg gggaaaccct gacgcagcaa cgccgcgtgc gggatgaagg       60
ccttcgggtt gtaaaccgct ttcagcaggg aagacatcga cggtacctgc agaagaagcc      120
ccggctaact acgtgccagc agccgcggta atacgtaggg ggcgagcgtt atccggattc      180
attgggcgta aagcgcgcgc aggcggttgc tcaagcggaa cctctaatct cggggcttaa      240
cctcgagccg gttccgaact ggacgactc gagtgcggta gaggcagatg gaattcccgg       300
tgtagcggtg gaatgcgcag atatcgggaa gaacaccaac ggcgaaggca gtctgctggg      360
ccgtcactga cgctgaggcg cgaaagctgg ggagcgaac aggattagat accctggtag       420
tcccagccgt aaacgatgag cgctgggtgt gggagattac atcttccgtg ccgaagctaa      480
cgcattaagc gctccgcctg gggagtacgg ccgcaaggct aaaactcaaa ggaattgacg      540
ggggcccgca caagcagcgg agcatgtggc ttaattcgaa gcaacgcgaa gaaccttacc     600
agggcttgac atgtaggtga agcggcggaa acgtcgtggc cgaaaggagc ctacacaggt     660
ggtgcatggc tgtcgtcagc tcgtgtcgtg agatgttggg ttaagtcccg caacgagcgc     720
aacccctgcc ccgtgttacc agcatttagt tgggactcg cggggactg ccggcgtcaa       780
```

```
gccggaggaa ggcggggatg acgtcaagtc atcatgcccc ttatgccctg ggccgcacac      840
gtgctacaat ggccggcaca gcgggctgca acctagcgat aggaagcgaa tcccgtaaag      900
ccggtcccag ttcggattgg aggctgaaac ccgcctccat gaagccggag ttgctagtaa      960
tcgcggatca gcacgccgcg gtgaatgcgt tcccgggcct                           1000
```

<210> SEQ ID NO 5
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (13)..(45)
<223> OTHER INFORMATION: Immobilized probe-binding region: Tail

<400> SEQUENCE: 5

```
ucuguuaguu cctttaaaaa aaaaaaaaaa aaaaaaaaaa aaaaa                      45
```

<210> SEQ ID NO 6
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 6

```
cggatgggtg agtaac                                                     16
```

<210> SEQ ID NO 7
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 7

```
aatttaatac gactcactat agggagataa gcccttacct tacca                     45
```

<210> SEQ ID NO 8
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 8

```
aatttaatac gactcactat agggagataa gccgttacct tacca                     45
```

<210> SEQ ID NO 9
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 9

```
gucugggaua ccacuuggaa acagac                                          26
```

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 10
cacucacgca ugucuagagu g                                         21

<210> SEQ ID NO 11
<211> LENGTH: 50
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (18)..(50)
<223> OTHER INFORMATION: Immobilized probe-binding region: Tail

<400> SEQUENCE: 11
caugcuccgc cgcuuguttt aaaaaaaaaa aaaaaaaaa aaaaaaaaaa            50

<210> SEQ ID NO 12
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 12
cttacctggg cttgacatgt gcctg                                     25

<210> SEQ ID NO 13
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 13
aatttaatac gactcactat agggagacac cacctgtgaa cctgc               45

<210> SEQ ID NO 14
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 14
ccugcagaga ugugguuucg cagg                                      24

<210> SEQ ID NO 15
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (22)..(54)
<223> OTHER INFORMATION: Immobilized probe-binding region: Tail

<400> SEQUENCE: 15
guaccgucga ugucuuccccu gtttaaaaaa aaaaaaaaaa aaaaaaaaaa aaaa    54

<210> SEQ ID NO 16
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 16
agcgttatcc ggattc    16

<210> SEQ ID NO 17
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 17
aatttaatac gactcactat agggagattc ggaacccggc tcgaggttaa g    51

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 18
ccgcucaggc gguugcucaa gcgg    24

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 19
ggattcattg ggcgtaaagc    20

<210> SEQ ID NO 20
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 20
gcgttatccg gattcat    17

<210> SEQ ID NO 21
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 21

```
aatttaatac gactcactat agggagataa gcctttacct tacca              45
```

<210> SEQ ID NO 22
<211> LENGTH: 46
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 22

```
aatttaatac gactcactat agggagaata cgacagctta cgccgc             46
```

<210> SEQ ID NO 23
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 23

```
aatttaatac gactcactat agggagatat ctgcgcattt caccgctaca c       51
```

<210> SEQ ID NO 24
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 24

```
aatttaatac gactcactat agggagacga ccatgcacca cctgt              45
```

<210> SEQ ID NO 25
<211> LENGTH: 57
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (25)..(57)
<223> OTHER INFORMATION: Immobilized probe-binding region: Tail

<400> SEQUENCE: 25

```
ggacuaccag gguaucuaau ccugtttaaa aaaaaaaaa aaaaaaaaa aaaaaaa    57
```

<210> SEQ ID NO 26
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (20)..(52)
<223> OTHER INFORMATION: Immobilized probe-binding region: Tail

<400> SEQUENCE: 26

```
guaggaguuu gggccgugut ttaaaaaaaa aaaaaaaaa aaaaaaaaa aa         52
```

```
<210> SEQ ID NO 27
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (21)..(53)
<223> OTHER INFORMATION: Immobilized probe-binding region: Tail

<400> SEQUENCE: 27
cuuugaguuu uagccuugcg tttaaaaaaa aaaaaaaaaa aaaaaaaaaa aaa            53

<210> SEQ ID NO 28
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (22)..(54)
<223> OTHER INFORMATION: Immobilized probe-binding region: Tail

<400> SEQUENCE: 28
gcaucgaauu aauccgcaug ctttaaaaaa aaaaaaaaaa aaaaaaaaaa aaaa           54

<210> SEQ ID NO 29
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (22)..(54)
<223> OTHER INFORMATION: Immobilized probe-binding region: Tail

<400> SEQUENCE: 29
guaguuagcc ggggcuucuu ctttaaaaaa aaaaaaaaaa aaaaaaaaaa aaaa           54

<210> SEQ ID NO 30
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (19)..(51)
<223> OTHER INFORMATION: Immobilized probe-binding region: Tail

<400> SEQUENCE: 30
uacguauuac cgcggcugtt taaaaaaaaa aaaaaaaaaa aaaaaaaaaa a              51

<210> SEQ ID NO 31
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (21)..(53)
<223> OTHER INFORMATION: Immobilized probe-binding region: Tail

<400> SEQUENCE: 31
cgugucucag ucccaaugug tttaaaaaaa aaaaaaaaaa aaaaaaaaaa aaa            53
```

```
<210> SEQ ID NO 32
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (19)..(51)
<223> OTHER INFORMATION: Immobilized probe-binding region: Tail

<400> SEQUENCE: 32
caauguggcc gaucaguctt taaaaaaaaa aaaaaaaaa aaaaaaaaaa a          51

<210> SEQ ID NO 33
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (22)..(54)
<223> OTHER INFORMATION: Immobilized probe-binding region: Tail

<400> SEQUENCE: 33
ccauugugga agauucccua ctttaaaaaa aaaaaaaaa aaaaaaaaaa aaaa       54

<210> SEQ ID NO 34
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (20)..(52)
<223> OTHER INFORMATION: Immobilized probe-binding region: Tail

<400> SEQUENCE: 34
cucgcucgac uugcauguat ttaaaaaaaa aaaaaaaaa aaaaaaaaaa aa         52

<210> SEQ ID NO 35
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (20)..(52)
<223> OTHER INFORMATION: Immobilized probe-binding region: Tail

<400> SEQUENCE: 35
cuugcaugua uuaggcacgt ttaaaaaaaa aaaaaaaaa aaaaaaaaaa aa         52

<210> SEQ ID NO 36
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (21)..(53)
<223> OTHER INFORMATION: Immobilized probe-binding region: Tail

<400> SEQUENCE: 36
```
cuuguaucua uguccauucc tttaaaaaaa aaaaaaaaaa aaaaaaaaaa aaa            53

<210> SEQ ID NO 37
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (20)..(52)
<223> OTHER INFORMATION: Immobilized probe-binding region: Tail

<400> SEQUENCE: 37
uggugcaagc accaaauuct ttaaaaaaaa aaaaaaaaaa aaaaaaaaaa aa             52

<210> SEQ ID NO 38
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (17)..(49)
<223> OTHER INFORMATION: Immobilized probe-binding region: Tail

<400> SEQUENCE: 38
aauucaucua ggcaagttta aaaaaaaaaa aaaaaaaaaa aaaaaaaaa                 49

<210> SEQ ID NO 39
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (17)..(49)
<223> OTHER INFORMATION: Immobilized probe-binding region: Tail

<400> SEQUENCE: 39
uccuaacguc auuaccttta aaaaaaaaaa aaaaaaaaaa aaaaaaaaa                 49

<210> SEQ ID NO 40
<211> LENGTH: 47
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (15)..(47)
<223> OTHER INFORMATION: Immobilized probe-binding region: Tail

<400> SEQUENCE: 40
uccauuccga agaatttaaa aaaaaaaaaa aaaaaaaaaa aaaaaaa                   47

<210> SEQ ID NO 41
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (20)..(52)
<223> OTHER INFORMATION: Immobilized probe-binding region: Tail

<400> SEQUENCE: 41
uugcugcguc agggguuuccu uaaaaaaaa aaaaaaaaaa aaaaaaaaaa aa        52

<210> SEQ ID NO 42
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (21)..(53)
<223> OTHER INFORMATION: Immobilized probe-binding region: Tail

<400> SEQUENCE: 42
gaaagcgguu uacaacccga tttaaaaaaa aaaaaaaaaa aaaaaaaaaa aaa       53

<210> SEQ ID NO 43
<211> LENGTH: 50
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (18)..(50)
<223> OTHER INFORMATION: Immobilized probe-binding region: Tail

<400> SEQUENCE: 43
aaggccuuca ucccgcattt aaaaaaaaaa aaaaaaaaaa aaaaaaaaaa           50

<210> SEQ ID NO 44
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (19)..(51)
<223> OTHER INFORMATION: Immobilized probe-binding region: Tail

<400> SEQUENCE: 44
ucgccguugg uguucuuctt taaaaaaaaa aaaaaaaaaa aaaaaaaaaa a         51

<210> SEQ ID NO 45
<211> LENGTH: 50
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (18)..(50)
<223> OTHER INFORMATION: Immobilized probe-binding region: Tail

<400> SEQUENCE: 45
ugacggccca gcagacuttt aaaaaaaaaa aaaaaaaaaa aaaaaaaaaa           50

<210> SEQ ID NO 46
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (21)..(53)
<223> OTHER INFORMATION: Immobilized probe-binding region: Tail

<400> SEQUENCE: 46
uccuguucgc uccccagcu tttaaaaaa aaaaaaaaaa aaaaaaaaaa aaa        53

<210> SEQ ID NO 47
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (17)..(49)
<223> OTHER INFORMATION: Immobilized probe-binding region: Tail

<400> SEQUENCE: 47
tcctaacgtc attaccttta aaaaaaaaaa aaaaaaaaa aaaaaaaaa        49

<210> SEQ ID NO 48
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (22)..(54)
<223> OTHER INFORMATION: Immobilized probe-binding region: Tail

<400> SEQUENCE: 48
gtaccgtcga tgtcttccct gtttaaaaaa aaaaaaaaaa aaaaaaaaaa aaaa        54

<210> SEQ ID NO 49
<211> LENGTH: 47
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (15)..(47)
<223> OTHER INFORMATION: Immobilized probe-binding region: Tail

<400> SEQUENCE: 49
cagcgcucau cguutttaaa aaaaaaaaaa aaaaaaaaa aaaaaaa        47

<210> SEQ ID NO 50
<211> LENGTH: 50
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (18)..(50)
<223> OTHER INFORMATION: Immobilized probe-binding region: Tail

<400> SEQUENCE: 50
acggaagaug uaaucucttt aaaaaaaaaa aaaaaaaaa aaaaaaaaaa        50

<210> SEQ ID NO 51
<211> LENGTH: 48
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (16)..(48)
<223> OTHER INFORMATION: Immobilized probe-binding region: Tail

<400> SEQUENCE: 51
gauguaaucu cccactttaa aaaaaaaaaa aaaaaaaaaa aaaaaaaa                48

<210> SEQ ID NO 52
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (13)..(45)
<223> OTHER INFORMATION: Immobilized probe-binding region: Tail

<400> SEQUENCE: 52
ccauuccgaa gatttaaaaa aaaaaaaaaa aaaaaaaaaa aaaaa                   45

<210> SEQ ID NO 53
<211> LENGTH: 44
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (12)..(44)
<223> OTHER INFORMATION: Immobilized probe-binding region: Tail

<400> SEQUENCE: 53
aguuucaucu gtttaaaaaa aaaaaaaaaa aaaaaaaaaa aaaa                    44

<210> SEQ ID NO 54
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (13)..(45)
<223> OTHER INFORMATION: Immobilized probe-binding region: Tail

<400> SEQUENCE: 54
ccgaagaauu uctttaaaaa aaaaaaaaaa aaaaaaaaaa aaaaa                   45

<210> SEQ ID NO 55
<211> LENGTH: 43
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (11)..(43)
<223> OTHER INFORMATION: Immobilized probe-binding region: Tail

<400> SEQUENCE: 55
uucaauaggc tttaaaaaaa aaaaaaaaaa aaaaaaaaaa aaa                     43

<210> SEQ ID NO 56
<211> LENGTH: 43
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (11)..(43)

```
<223> OTHER INFORMATION: Immobilized probe-binding region: Tail

<400> SEQUENCE: 56
cgucauuacc tttaaaaaaa aaaaaaaaaa aaaaaaaaaa aaa                         43

<210> SEQ ID NO 57
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (13)..(45)
<223> OTHER INFORMATION: Immobilized probe-binding region: Tail

<400> SEQUENCE: 57
ccaaauucau cutttaaaaa aaaaaaaaaa aaaaaaaaaa aaaaa                       45

<210> SEQ ID NO 58
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (13)..(45)
<223> OTHER INFORMATION: Immobilized probe-binding region: Tail

<400> SEQUENCE: 58
aacgucauua cctttaaaaa aaaaaaaaaa aaaaaaaaaa aaaaa                       45

<210> SEQ ID NO 59
<211> LENGTH: 45
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (13)..(45)
<223> OTHER INFORMATION: Immobilized probe-binding region: Tail

<400> SEQUENCE: 59
uuuccuaacg uctttaaaaa aaaaaaaaaa aaaaaaaaaa aaaaa                       45

<210> SEQ ID NO 60
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 60
ccugcagaga ugugguuucg cagg                                              24

<210> SEQ ID NO 61
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 61
cugggauacc acuuggaaac acccag                                            26
```

```
<210> SEQ ID NO 62
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 62
ucugggauac cacuuccaga                                              20

<210> SEQ ID NO 63
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 63
ccugcagaga ugugguuucg cagg                                         24

<210> SEQ ID NO 64
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 64
gguucugcua ucacucuugg aacc                                         24

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 65
acgcaugucu agaguugcgu                                              20

<210> SEQ ID NO 66
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 66
agacgcaugu cuagagcguc u                                            21

<210> SEQ ID NO 67
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 67
gaugcuaaua ccggauaaca acgcauc                                      27

<210> SEQ ID NO 68
<211> LENGTH: 28
<212> TYPE: DNA
<213> ORGANISM: Artificial Sequence
<220> FEATURE:
<223> OTHER INFORMATION: Synthetic Oligomer
```

<400> SEQUENCE: 68
uaccggauaa caacacuaga cgccggua                                          28

<210> SEQ ID NO 69
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 69
gucugggaua ccauuuggaa acagac                                            26

<210> SEQ ID NO 70
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 70
gucugggaua ccacuuggaa acagac                                            26

<210> SEQ ID NO 71
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 71
gucugggaua ccacuuggaa acagac                                            26

<210> SEQ ID NO 72
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 72
gguucugcua ucacucuugg aacc                                              24

<210> SEQ ID NO 73
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 73
gguucugcua ucacucuugg aacc                                              24

<210> SEQ ID NO 74
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 74
cgcaugucua gaguugcg                                                     18

<210> SEQ ID NO 75
<211> LENGTH: 19

```
<212> TYPE: DNA
<213> ORGANISM: Artificial Sequence
<220> FEATURE:
<223> OTHER INFORMATION: Synthetic Oligomer

<400> SEQUENCE: 75
acucacgcau gucuagagu                                                    19

<210> SEQ ID NO 76
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 76
gagacgcaug ucuagaguug ucuc                                              24

<210> SEQ ID NO 77
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 77
guugcucaag cggaaccucg caac                                              24

<210> SEQ ID NO 78
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 78
uugcucaagc ggaaccucua gcaa                                              24

<210> SEQ ID NO 79
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 79
gcucaagcgg aaccucugag c                                                 21

<210> SEQ ID NO 80
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 80
agcggaaccu cuaaucucgu cgcu                                              24

<210> SEQ ID NO 81
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 81
```
ccgcucaggc gguugcucaa gcgg                                              24

<210> SEQ ID NO 82
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 82
ccgcucaggc gguugcucaa gcgg                                              24

<210> SEQ ID NO 83
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 83
ccgcucaggc gguugcucaa gcgg                                              24

<210> SEQ ID NO 84
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 84
ccgcucaggc gguugcucaa gcgg                                              24

<210> SEQ ID NO 85
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 85
ccgcucaggc gguugcucaa gcgg                                              24

<210> SEQ ID NO 86
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 86
ccgcucaggc gguugcucaa gcgg                                              24

<210> SEQ ID NO 87
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 87
ccgcucaggc gguugcucaa gcgg                                              24

<210> SEQ ID NO 88
<211> LENGTH: 1496
<212> TYPE: DNA
<213> ORGANISM: Lactobacillus jensenii -continued

```
<300> PUBLICATION INFORMATION:
<308> DATABASE ACCESSION NUMBER: GenBank/NR_025087.1  GI:219857499
<309> DATABASE ENTRY DATE: 2009-01-09
<313> RELEVANT RESIDUES IN SEQ ID NO: (1)..(1496)

<400> SEQUENCE: 88
tgcctaatac atgcaagtcg agcgagcttg cctatagaag ttcttcggaa tggaaataga      60
tacaagctag cggcggatgg gtgagtaacg cgtgggtaac ctgcccttaa gtctgggata     120
ccatttggaa acagatgcta ataccggata aaagctactt tcgcatgaaa gaagtttaaa     180
aggcggcgta agctgtcgta aaggatggac ttgcgatgca ttagctagtt ggtaaggtaa     240
cggcttacca aggctgatga tgcatagccg agttgagaga ctgatcggcc acattgggac     300
tgagacacgg cccaaactcc tacgggaggc agcagtaggg aatcttccac aatggacgaa     360
agtctgatgg agcaacgccg cgtgagtgaa gaaggttttc ggatcgtaaa gctctgttgt     420
tggtgaagaa ggatagaggt agtaactggc ctttatttga cggtaatcaa ccagaaagtc     480
acggctaact acgtgccagc agccgcggta atacgtaggt ggcaagcgtt gtccggattt     540
attgggcgta aagcgagcgc aggcggattg ataagtctga tgtgaaagcc ttcggctcaa     600
ccgaagaact gcatcagaaa ctgtcaatct tgagtgcaga agaggagagt ggaactccat     660
gtgtagcggt ggaatgcgta gatatatgga agaacaccag tggcgaaggc ggctctctgg     720
tctgtaactg acgctgaggc tcgaaagcat gggtagcgaa caggattaga tacctggta      780 gtccatgccg taaacgatga gtgctaagtg ttgggaggtt tccgcctctc agtgctgcag     840
ctaacgcatt aagcactccg cctggggagt acgaccgcaa ggttgaaact caaaggaatt     900 gacggggcc cgcacaagcg gtggagcatg tggtttaatt cgaagcaacg cgaagaacct      960
taccaggtct tgacatcctt tgaccaccta agagattagg ttttcccttc gggacaaag     1020 agacaggtgg tgcatggctg tcgtcagctc gtgtcgtgag atgttgggtt aagtcccgca    1080
acgagcgcaa cccttgttaa tagttgccag cattaagttg ggcactctat tgagactgcc    1140
ggtgacaaac cggaggaagg tggggatgac gtcaagtcat catgcccctt atgacctggg    1200
ctacacacgt gctacaatgg gcagtacaac gagaagcgaa cctgtgaagg caagcggatc    1260
tcttaaagct gttctcagtt cggactgtag gctgcaactc gcctacacga agctggaatc    1320
gctagtaatc gcggatcagc acgccgcggt gaatacgttc ccgggccttg tacacaccgc    1380
ccgtcacacc atgagagttt gtaacaccca aagtcggtga ggtaacccttt ggagccagcc   1440 gcctaaggtg gacagatga ttagggtgaa gtcgtaacaa ggtagccgta ggagaa         1496
```